(12) United States Patent
Khan et al.

(10) Patent No.: US 11,504,000 B2
(45) Date of Patent: Nov. 22, 2022

(54) OPHTHALMOLOGIC TESTING SYSTEMS AND METHODS

(71) Applicant: XENON-VR, INC., Belleville, NJ (US)

(72) Inventors: Zeshan Ali Khan, Belleville, NJ (US); Steve Susanibar, North Arlington, NJ (US)

(73) Assignee: XENON-VR, INC., Belleville, NJ (US)

( * ) Notice: Subject to any disclaimer, the term of this patent is extended or adjusted under 35 U.S.C. 154(b) by 0 days.

(21) Appl. No.: 17/584,855

(22) Filed: Jan. 26, 2022

(65) Prior Publication Data
US 2022/0151489 A1    May 19, 2022

Related U.S. Application Data

(63) Continuation of application No. PCT/US2020/044230, filed on Jul. 30, 2020.

(60) Provisional application No. 62/881,120, filed on Jul. 31, 2019.

(51) Int. Cl.
*A61B 3/00* (2006.01)
*A61B 3/10* (2006.01)
*A61B 3/12* (2006.01)
*A61B 3/14* (2006.01)

(52) U.S. Cl.
CPC ............. *A61B 3/12* (2013.01); *A61B 3/0008* (2013.01); *A61B 3/102* (2013.01); *A61B 3/14* (2013.01)

(58) Field of Classification Search
CPC ....... A61B 3/12; A61B 3/0008; A61B 3/0041; A61B 3/0058; A61B 3/1208; A61B 3/1225; A61B 3/102; A61B 3/14; G02C 27/017; G02C 27/0172; G02C 27/0176; G02C 2027/0178; G02B 27/017; G02B 27/0172; G02B 27/0176; G02B 2027/0178
See application file for complete search history.

(56) References Cited

U.S. PATENT DOCUMENTS

| | | | |
|---|---|---|---|
| 5,543,816 | A | 8/1996 | Hancock |
| 5,993,001 | A | 11/1999 | Bursell et al. |
| D918,903 | S | 5/2021 | Jackson et al. |
| D918,904 | S | 5/2021 | Jackson et al. |
| 11,089,954 | B2 | 8/2021 | Jackson et al. |

(Continued)

OTHER PUBLICATIONS

International Search Report, U.S. Patent and Trademark Office, Application No. PCT/US20/44230, dated Jan. 5, 2021.

(Continued)

*Primary Examiner* — Jordan M Schwartz
(74) *Attorney, Agent, or Firm* — Gottlieb Rackman & Reisman PC

(57) ABSTRACT

A modular, headset for performing ophthalmic tests on a patient comprises a removable optical module that can be replaced based on ophthalmic testing need. A miniaturized fundus camera is provided and can be movably mounted within the headset, including to the optical module. The fundus camera position can be automatically adjusted to align the camera with a headset wearer's eye. Software controls image capture and captured images are combined assembled and combined to provide a wide field retinal image. The optical module can have replaceable sub-components allowing configuration for different ophthalmic tests, such as visual field testing and optical coherence tomography.

28 Claims, 38 Drawing Sheets

(56) References Cited

U.S. PATENT DOCUMENTS

| | | |
|---|---|---|
| D934,242 S | 10/2021 | Jackson et al. |
| D934,243 S | 10/2021 | Jackson et al. |
| 11,344,194 B2 | 5/2022 | Jackson et al. |
| 2012/0062839 A1 | 3/2012 | Su et al. |
| 2014/0267208 A1 | 9/2014 | Yajima et al. |
| 2016/0262608 A1 | 9/2016 | Krueger |
| 2016/0306173 A1* | 10/2016 | Tsukahara .......... G02B 27/0172 |
| 2017/0153672 A1 | 6/2017 | Shin et al. |
| 2017/0325675 A1 | 11/2017 | Liu et al. |
| 2018/0088890 A1 | 3/2018 | Pohl |
| 2018/0206720 A1* | 7/2018 | Wang ................... A61B 3/0083 |
| 2019/0171023 A1 | 6/2019 | Carlvik et al. |
| 2019/0246900 A1* | 8/2019 | Krumholz ................ A61B 3/12 |
| 2019/0313903 A1* | 10/2019 | McKinnon ............... A61B 3/12 |

OTHER PUBLICATIONS

Written Opinion, U.S. Patent and Trademark Office, Application No. PCT/US20/44230, dated Jan. 5, 2021.

\* cited by examiner

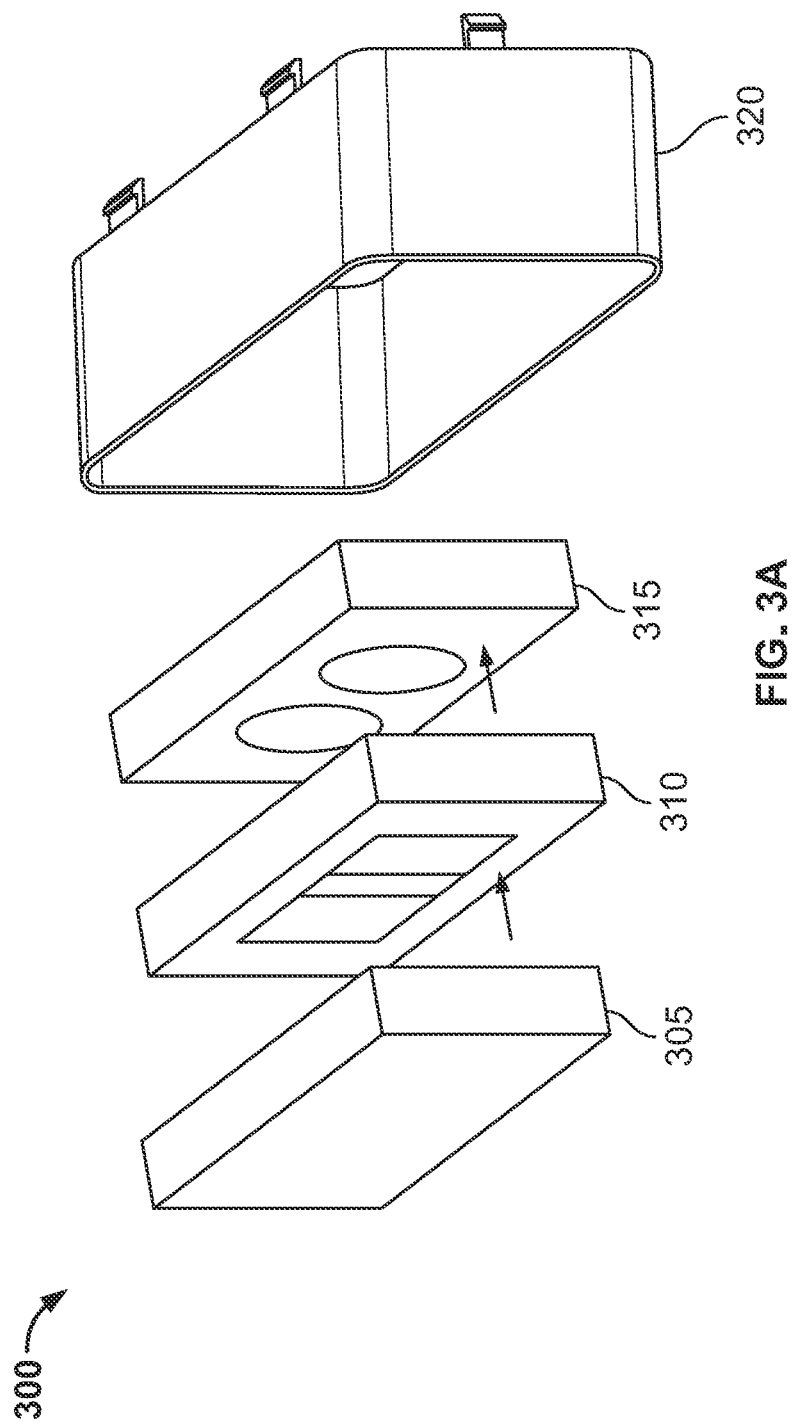

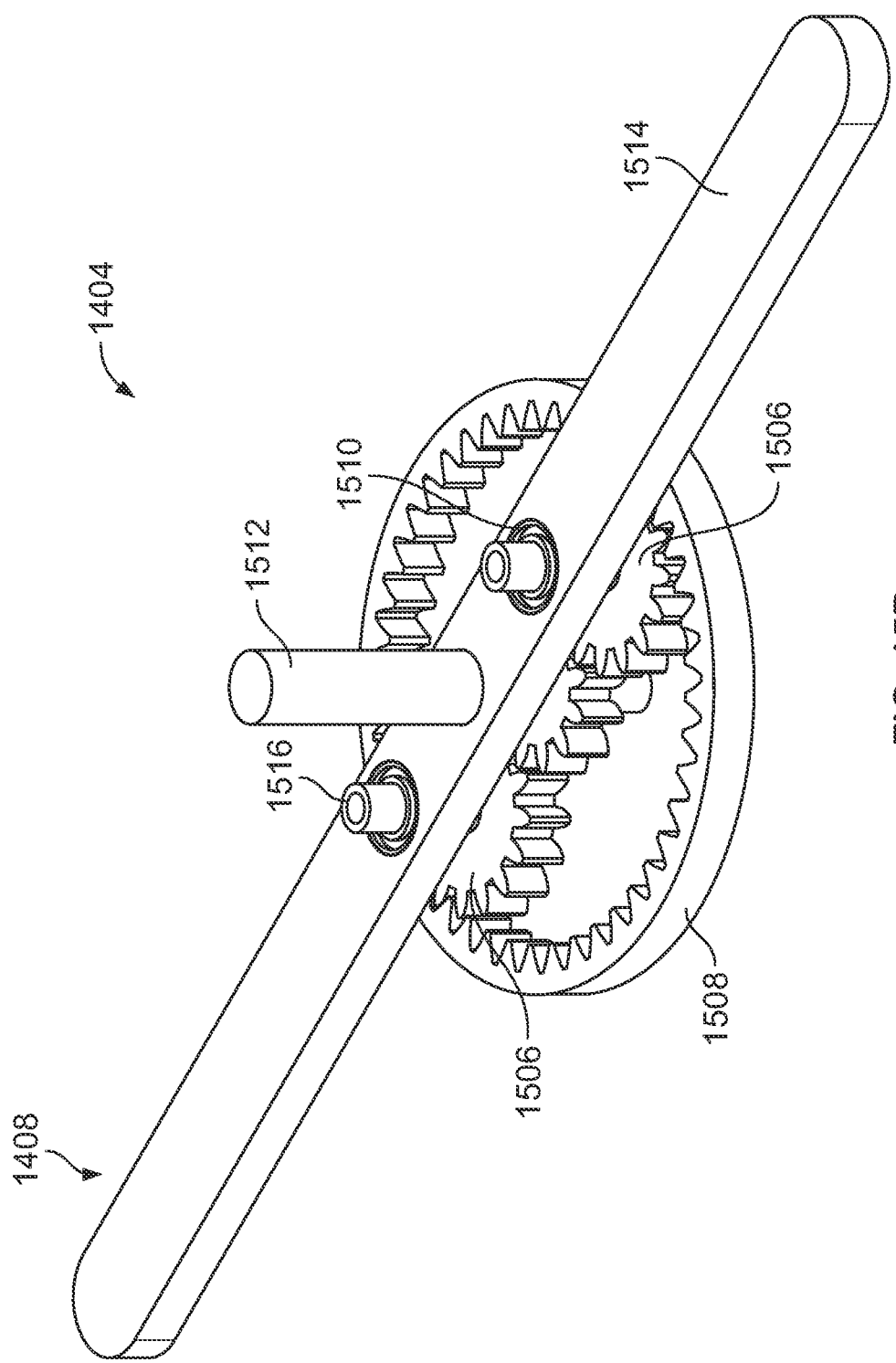

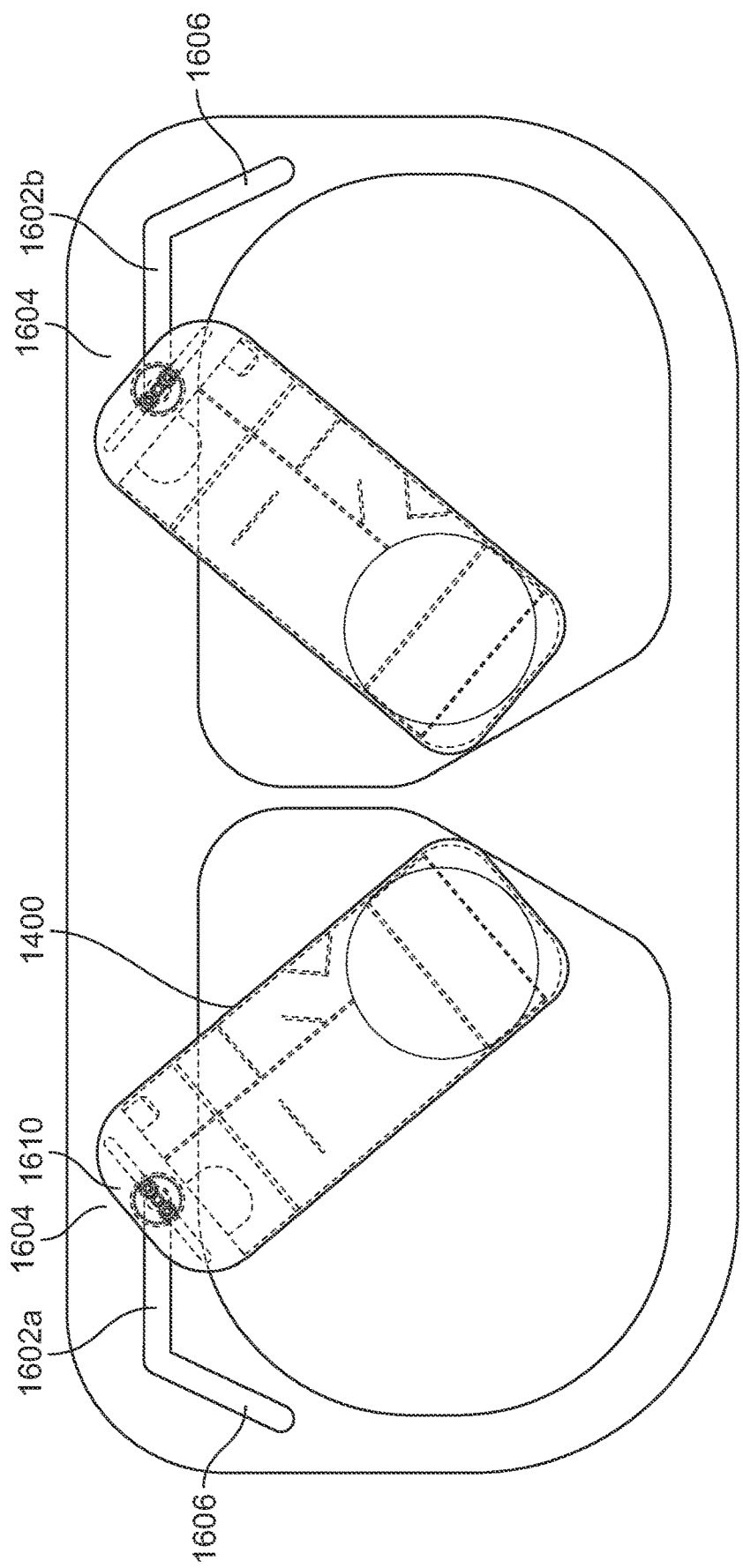

OPHTHALMOLOGIC TESTING SYSTEMS AND METHODS

CROSS-REFERENCE TO RELATED APPLICATIONS

This application is a continuation of PCT application US2020/044230, filed Jul. 30, 2020 and which claims priority to U.S. Provisional Patent Application Ser. No. 62/881,120, filed Jul. 31, 2019, the entire contents of which is expressly incorporated by reference.

FIELD OF THE INVENTION

The present invention is related to improvements in systems for visual testing and ophthalmological imaging, including improved head-mounted hardware that contains ophthalmic devices and systems that use such devices.

BACKGROUND

Eye care is an important part of overall health and many specialized systems have been developed to allow ophthalmologists to examine a person's eyes. Many of these devices are expensive, limiting their availability. They are also bulky, often requiring a dedicated table or mounting a special stand. The size, weight, and general ungainliness of these devices also can require dedicated space in a doctor's office to be reserved for that equipment.

To use these devices to examine a patient the patient is generally required to place their head in a specific location and hold it there while an eye is examined. Patients who have mobility limitations might not be physically able to position themselves as required for examination using a particular optical tool. This can limit the ability to provide comprehensive eye examinations to these patients. Likewise, due to bulk and expense, it may be difficult or impossible to bring a variety of these specialized eye examination systems to a patient who is not able to travel to the doctor's office.

A common tool for eye examination is a fundus camera used to capture images of the retina. A fundus camera is a specialized low power microscope with a camera attached. A conventional fundus camera system has a housing roughly one to two feet in each dimension with an objective lens at one side and a camera display on the other. In use, the patient is seated before a table holding the fundus camera system, rests their chin on a chin rest attached to the system, and presses their forehead against a forehead bar. The chin rest position is adjusted so that the patient's eye is opposite the objective lens of the camera system. The camera is then focused and one or more pictures are taken. During this process, the patient may reposition their forehead for comfort or because of natural tendencies to move their neck, e.g., due to stiffness. Such motion may take the eye out of alignment with the camera and also require that the doctor refocus the camera.

Similarly, conventional equipment used to perform perimetry or visual field are sensitive to motion of the patient's head and eye during use, require the patient to place their head in a chin rest, and are also bulky and expensive, limiting portability and availability outside of a dedicated setting. For visual field testing, the user looks at the center of a bowl-shaped 'perimeter' instrument. Lights or other objects are shown within the instrument and the patient indicates when those are seen. Mapping what is and is not seen by the patient shows their visual field. Motion of the patient's head relative to the optical field of the perimetry test can shift their field of view and degrade the accuracy of the test results. Results can also be degraded if the patient shifts their gaze from the center target even if their head remains still.

OCT is a non-invasive imaging technique relying on low coherence interferometry to generate in vivo, cross-sectional imagery of ocular tissues. OCT is used to detect disease and provides a quantitative and repeatable method to evaluate surgical and pharmacological interventions. Over the past ten years OCT systems have become more common in community optometric practice and over the last ten years and has continued to evolve in capability, with higher scan density, faster acquisition and processing speed of data and computerized image analysis.

Conventional equipment for coherence tomography (OCT) scanning has similar deficiencies to conventional fundus cameras and perimetry testing systems. A patient must sit at the OCT machine and keep their head motionless for 5 to 10 minutes as the system scans the eye. Motion of the patient's head can lead to misalignment issues. To prevent motion by the patient an assistant is often required to be physically present to throughout the entirety of the exam to monitor the patient's head orientation and correct the position as needed. OCT scanning equipment can also be bulky and expensive.

There is a need for a portable and inexpensive system for performing eye examinations in a variety of environments and that can easily be used without requiring a patient's head be seated in a chin and forehead rest. It would also be advantageous if such a system were available for performing fundus imaging, perimetry testing, and for use in OCT imaging. It would be a further advantage if such a system can be easily configured and reconfigured to allow use for different types of eye examinations, such as fundus imaging, OCT imaging, and perimetry testing, instead of requiring dedicated testing systems for each.

SUMMARY

These and other issues and deficiencies are addressed by headset system that can be worn by a patient and that comprises an optical module that can be configured to support a variety of optical tests. The optical module can be removable from the headset allowing a module configured for one test to be replaced by a module configured for a different test. The optical modular can be made of removable sub-modules allowing a single module to be customized for use in applying different optical tests. A miniaturized fundus camera can be movably mounted within the headset to allow the camera position to be adjusted relative to a patient's eye. Multiple images captured by the fundus camera can be combined to generate a very wide-angle view of the retina. Optical displays and other illuminated elements can be used for perimetry testing.

In an embodiment, a fundus camera comprises a housing with first and second ends, a front side, a back side, a major axis running from the first and second ends, and an aperture opening in the first side. A camera assembly is mounted in an interior of the housing. The camera has a field of view extending from the aperture. The fundus camera comprises an illumination source configured to produce an illumination light beam, an electronic image capture camera, an objective lens, and an exit mirror. The illumination light beam follows an illumination light beam path from the illumination source to the exit mirror. The exit mirror redirects the illumination light beam path through the objective lens, which can be a spherical lens, and into the field of view. It also redirects light from the illumination light beam reflected by an object in the field of view and returning through the objective lens along a returning light path extending back to the imaging camera. The paths in the camera of the outgoing light to illuminate the field of view and incoming light from an illuminated object can be substantially parallel.

A mirror, such as the exit mirror can be rotatable or pivotable to change the direction of the illumination light beam path in the field of view and thereby illuminate different portions of a patient's retina. The direction of the camera field of view is also changed. An attenuating element, such as a beam splitter, can be used to reduce the intensity of the illumination light. Internal fold mirrors operate to increase the optical path while keeping dimensions of the camera small. Glare reduction elements can also be included.

The fundus camera can further comprise a rotatable mounting assembly configured to allow the camera within an elongated housing to be rotatably mounted within a headset or other system. The rotatable mounting assembly can be on the back of the housing adjacent a first end of the housing and the imaging aperture on the front of the housing adjacent the second end. In an embodiment the mounting assembly comprises a gearing system that includes a fixed gear attached to the housing and a rotating gear that is coupled to the fixed gear and mounted to a shaft such that rotation of the shaft causes the camera to pivot.

In an embodiment, a headset system is provided for use in optical examination of a user. The headset comprises a body configured to be worn on the face of a user. The face side of the headset has a forward edge configured to rest on the user's face when the headset is worn. A fundus camera, such as described above, is rotatably mounted within the headset and positioned so that it can be moved in front of a user's eye when the headset is being worn. Rotating the fundus camera allows the camera objective to be moved relative to the user's eye when the headset is worn so that the camera can be repositioned as needed to image the retina. A motor can be provided to selectively rotate the fundus camera, such as under the control of a computer program. A single fundus camera can be mounted a point substantially midway between the left and right sides of the body and rotatable from a first position left position to image a left eye of a user wearing the headset to a second right position to image a right eye of the user wearing the headset. Alternatively, separate left and right rotatably mounted fundus cameras can be provided and positioned to image the left and right eye, respectively. The fundus camera mount can slidably engage the headset and be movable, such as in a track, between a first and second position. Changing the position of the mount within the track moves the fundus camera and allows the position of the camera relative to a patient's eye to be changed. In an embodiment the fundus cameras are both rotationally and slidably mounted to provide multiple degrees of freedom of position adjustment.

Eye tracking cameras can be included within the head set that are operative to capture images of the user's eyes, which images are processed to determine the position and/or direction of gaze of the eye. Multiple images can be capture by the fundus camera and combined to generate a very wide field image of the retina. Eye tracking data captured along with the fundus camera images can be used to determine which portion of the retina has been imaged in any given image captured by fundus camera and this data used to map captured images into a combined image of the retina.

One or more visual displays can be provided in the headset and situated behind the fundus camera. The displays can be used to present images to a person wearing the headset. The fundus cameras can be movable between an imaging position where the fundus camera obscures a portion of the visual display and a storage position where substantially none of the visual display is obscured by the fundus camera. The fundus camera could also be removably mounted within the headset body so that the headset can be used with or without the fundus cameras.

According to an aspect of the invention, a computer controlled method for fundus imaging of a retina of a patient's eye is presented. A headset is placed on the head of a patient. The headset comprises a body and a rotatably mounted fundus camera, such as above that can be moved to different positions in front of the patient's eye. An image of a user's eye is captured by the fundus camera. The position of the fundus camera is adjusted based on the first image to improve the alignment of the camera objective with a pupil the eye. Adjustment can be automatic or manual. Once adjusted, a plurality of retinal images are captured with the fundus camera.

During image capture, the user can be instructed to change the direction of their gaze so that the camera can image different portions of the retina. These instructions can be audible. In an embodiment the headset further comprises a plurality of visible light sources arranged around an internal periphery and that are visible to the user. The method includes illuminating at least one of the plurality of visible light sources to indicate the desired gaze direction.

The plurality of captured retinal images are mapped to a respective position in a retinal image map and then stitched together to form a combined wide field view of the retina. The position of a respective retinal image in the retinal image map is on the portion of the retina imaged in the respective retinal image. This can be determined with reference to data indicating the position and aim of the fundus camera relative to the eye and the direction of gaze of the eye, e.g., as determined by means of eye tracking cameras. Eye tracking data capture during fundus imaging can be stored in conjunction with the fundus images for use in image mapping after the fundus image capture session is complete.

The fundus image capture can be automatically terminated after a determination that a sufficient portion of the retina has been imaged to allow a complete mapping of the desired portions of the retina. If a determination is made that a portion of the retina has not been successfully imaged, the computer can automatically instruct the patient to alter the gaze direction so as to bring the portion of the retina that has not been successfully imaged into the field of view of the fundus camera.

According to a further aspect of the invention a wearable optical headset system is provided that comprises a generally tubular outer frame having an interior extending between open front and back portions of the outer frame, where the front portion is configured to be pressed against a user's face and surround the eyes of the user. At least one headstrap attached to the outer frame is configured to hold the outer frame against the user's face when the headset is worn. An optics module housing having a front and a back and side surfaces, the optics module configured to be removably slidably engaged within the interior of the outer frame with the front of the optics module visible through the front portion of the outer frame. The optics module housing encloses computer circuitry including a computer processor, a digital memory connected to the processor and configured to store computer software executable by the processor, and an optical component comprising at least one of an image display system and an image capture system. The optical component is electrically connected to the processor and controllable by the processor in accordance with stored computer software. The optics module can be secured to the headset housing with elastic clips arranged along an outer periphery of the optics housing that engage a corresponding plurality of apertures in the outer frame.

A first electronic display can be mounted on a back surface of the optics module and configured to output visual data in response to signals from the processor. A second electronic display can be mounted on an outer side of the outer frame and configured to output visual data. An electrical interface between the headset housing and the optics module can be provided to allow the system within the optics module to control the display mounted on the outer frame. Various user input devices can be provided on the optics module and/or the outer frame.

The removable optics module can comprise a rotatable fundus camera and eye tracking cameras configured to image the eye of the user wearing the headset. Visible light LEDs can be positioned along a periphery of the optics module where they are visible by a user wearing the headset.

According to a further aspect, the optics module is itself modular and comprises a plurality of subcomponents. Each subcomponent has a respective housing with a front surface and a back surface, wherein the subcomponents can be stacked from the back of the optics module to the front of the optics module, and where each subcomponent is removably connected to an adjacent subcomponent. In an embodiment, a first subcomponent comprises a circuit board having the computer circuitry therein and a second subcomponent comprises a visual display to be viewed by a wearer of the headset. Electrical and mechanical interfaces are provided on adjoining surfaces of the subcomponents. When connected, the visual display in the second subcomponent is controllable by the processor in the first subcomponent. A third subcomponent comprising functional components for use in administrating eye examinations can be provided and mounted in the optics module in front of the second subcomponent. In an embodiment, the third subcomponent comprises a fundus camera which can be rotatably mounted to the third subcomponent.

In an embodiment the optics module comprises a generally planar circuit board having a front and back and having computer circuitry thereon. The optical component comprises first and second visual displays, which can be micromirror displays. Each visual display is electrically connected to the circuit board. First and second lens assemblies, positioned respectively in front of the first and second displays are operative to form virtual images of images presented on the corresponding displays. The virtual images appear to a user wearing the headset to be at a first distance from the user that is greater than-an actual distance between the user's eyes and the visual display. The lens assemblies can comprise liquid lenses having an electrically controllable focus responsive to signals from the computer circuitry. The apparent distance of the virtual images can be changed by adjusting the liquid lens focus.

The display in the optical system can be a retinal image display comprising a light emitter configured to emit a beam of light. An integrator rod is positioned to receive the beam of light when being emitted and to output an integrated beam of light. At least one lens is configured to receive the light beam from the integrator rod and focus the light beam. A beam splitter in the path of the focused light beam directs a portion of the focused light beam to intersect a face of a digital micromirror device (DMD). Light reflected from the DMD reenters the beam splitter and a portion is passed through to a projection lens that focusing the reflected light for viewing by a user wearing the headset of an image generated by the DMD.

A fundus camera can also be rotatably mounted to a front frame in the optics module and configured to image eye structures of a person wearing the headset system.

DESCRIPTION OF THE DRAWINGS

Further features and advantages of the invention, as well as structure and operation of various implementations of the invention, are disclosed in detail below with references to the accompanying drawings in which:

FIGS. 3A and 3B are illustrate an optical module comprising several sub-components;

FIGS. 15A and 15B show a top and bottom view of the geared mounting assembly of FIG. 14B;

FIGS. 16A-16E illustrate a slidably mounted fundus camera;

FIGS. 18A-18C illustrate a top and perspective exploded views of a miniaturized fundus camera design; and.

DETAILED DESCRIPTION

Figure 1:
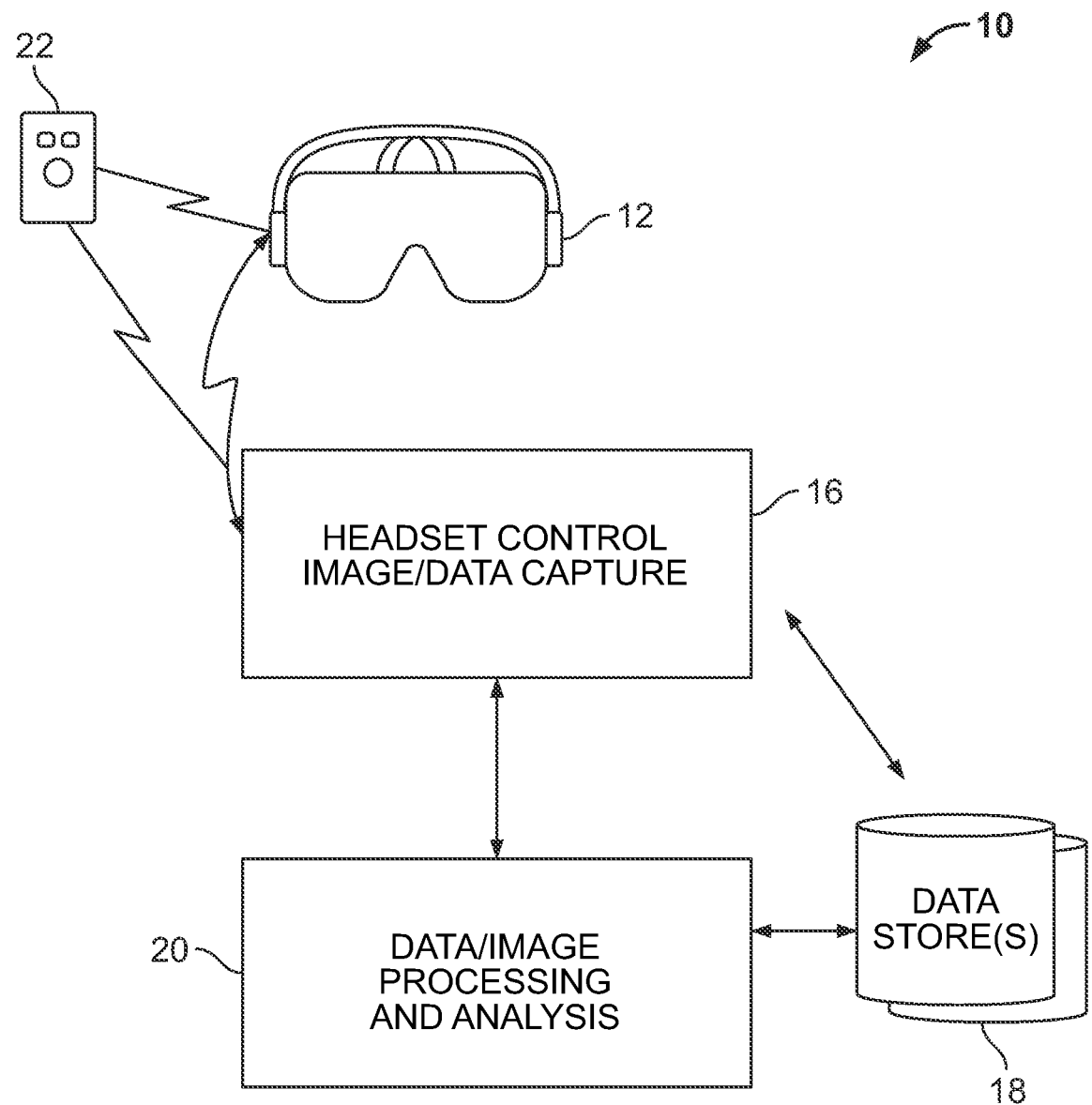
FIG. 1 is a simplified high-level block diagram of a general ophthalmologic testing system.

FIG. 1 is a simplified high level block diagram of a general ophthalmologic testing system 10 in which optical tests and data capture, such as fundus imaging, visual field testing, and OCT scans, are performed using equipment mounted in a portable headset 12 that can be worn by a patient. The headset 12 includes internal equipment 14 (not shown) that is used to capture the images or data from one or both eyes of a patient wearing the headset 12. As addressed further below, this equipment 14 can include lenses, cameras, optical emitters, visual displays, mechanical structures, electronics, and computing hardware and software for administrating one or more optical tests, such as fundus imaging, visual field testing, OCT, and autorefraction. A given headset 12 can be dedicated for use in a single type of test. The headset equipment components 14 can be modular and some or all can be removed from the headset housing and replaced with different components to allow the same headset 12 to be used for a wide variety of different types of eye tests.

While certain computing hardware and software can be integrated within the headset 12, a separate control system 16 for headset control and image/data capture can be connected to the headset 12 and comprise computing hardware and software that is used to control the headset components 14 during the testing process. For example, the control system 16 may be used to configure the headset 12 with test parameters, initiate the testing process, and receive the captured test data from the headset.

Captured test data can be stored in one or more electronic data stores 18. Data store 18 may be internal to or external from the control system 16 and connected directly or through a network. Any suitable data store 18 can be provided, such as an internal or external hard drive or networked/cloud-based data storage. A separate system 20 can also be provided with data and image processing and analysis functionality to augment that available in the control system 16. System 20 can be local to control system 16 or connected remotely through a network. In one configuration, control system 16 is a local computer, such as a tablet, laptop or desktop computer with internal memory serving as data store 18, and the system 20 is a remote server with its own data store and through which a specialist can connect to access the test data, e.g., a doctor viewing the eye test data for remote diagnosis.

During optical testing when a patient is wearing the headset 12, there may be a need for the patient to provide input, such as indicating when they see a particular feature on the display. A hand controller, keyboard, fob, or other input device 22 can be provided for this purpose. The input device 22 can be connected to systems within the headset 12 or to the control system 16 using a wired or wireless link, such as a plug-in USB cable or Bluetooth connection.

In accordance with various aspects of the invention, use of a headset system as disclosed herein for eye testing provides a variety of advantages. When properly worn the headset will move with the user's head and so proper optical alignment of imaging and other equipment in the headset can be maintained with the user's eyes even as the user's head moves around. This can be especially useful for small children who cannot keep still during eye exams and are more prone to fidget and for older individuals who have ADHD tendencies or motion disorders including general paralysis, Parkinson's disease, Lou Gehrig's Disease ALS, Tourette Syndrome, tremors, ataxia, dystonia, multiple system atrophy, Rett Syndrome or myoclonus.

The system allows for easier examination of patients with mobility issues. For example, if a person needs to lie in bed due to bodily injuries that would otherwise not allow him or her to sit on a chair to perform the standard tabletop exam, the headset 12 can be placed on their head and the standard eye exams performed while the patient is lying in bed.

A headset system with integrated optical testing equipment can eliminate the need to have a second person present during an eye test and who properly places a camera barrel in front of the patient's eye (a process that may also make the user uncomfortable). Instead, the headset can be put on by the patient directly.

The headset 12 can be configured to display a 3D virtual reality environment for eye examinations. Eye-tracking functionality can be provided within the headset and used to monitor the position of a user's eyes and direction of their gaze during a virtual examination in configurations where the user is presented with an image to see or in other testing configurations that might not use a target image. The system 10 is particularly useful to detect early signs of dyslexia in children in the age group of five and younger—the age range when most development of the eye is occurring.

Liquid lens technology can be incorporated into a lens system between the user's eyes and the internal displays. The optical properties of the liquid lens can be controlled to adjust the apparent distance of a virtual image formed by the images on the displays. This can be useful for testing for or simulating near or far sightedness. The use of liquid lenses also permits the headset system to be configured as a head-mounted phoropter. The power of the liquid lenses can be automatically adjusted to avoid the conventional need to have another person mechanically change the optical power of the lenses a user looks through during the testing process.

The headset can be configured to provide room for wearing glasses while performing eye examinations. For patients, whose eye vision needs large refractive correction, the device can allow for optimal fitting of glasses while using the ophthalmic instrument while not limiting the field of view of the screen. Enhanced immersion in eye exams is also possible which may improve the reliability of test results, especially for clinical purposes.

Figure 2A:
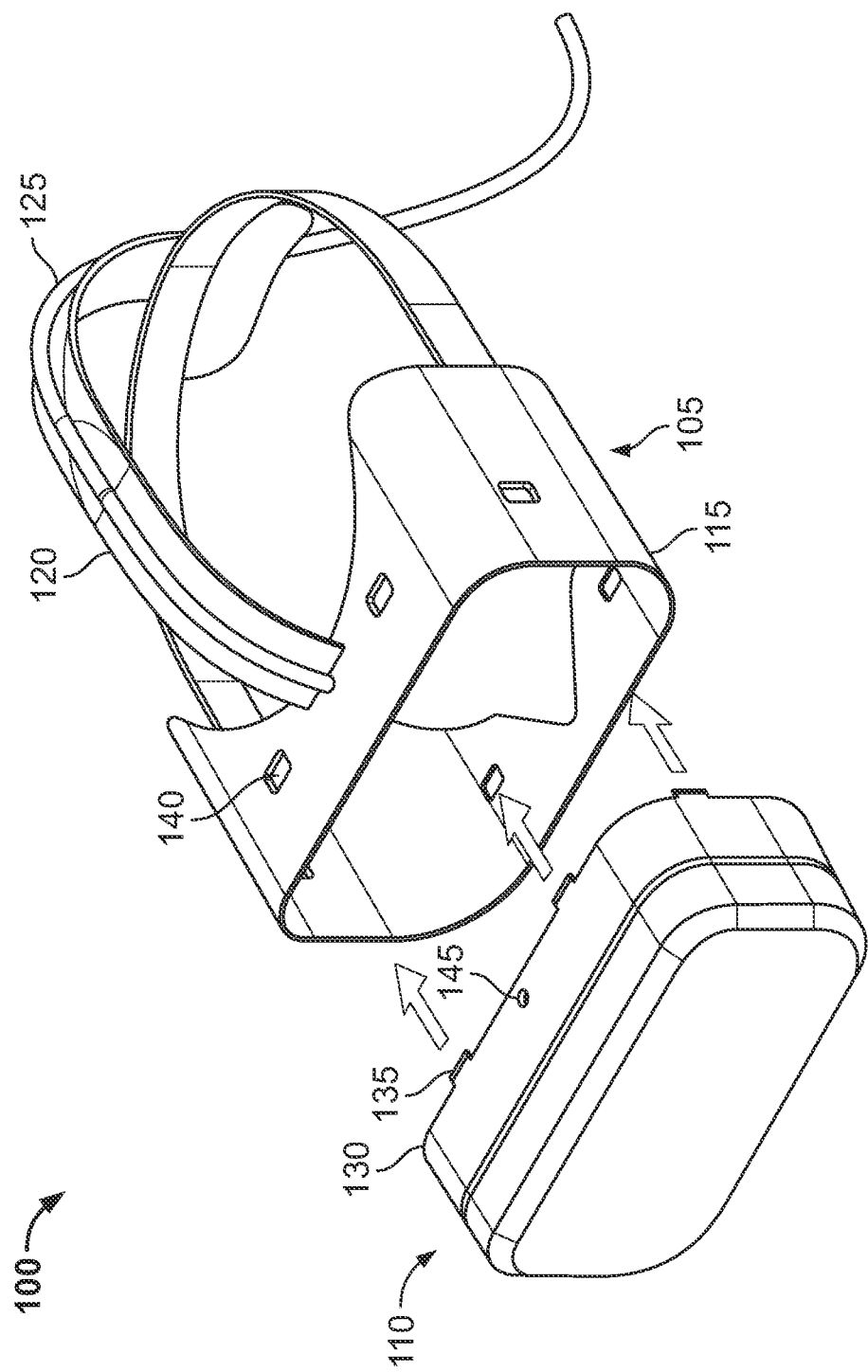
FIGS. 2A and 2B illustrate a modular headset system according to an aspect of the invention.
Figure 2B:
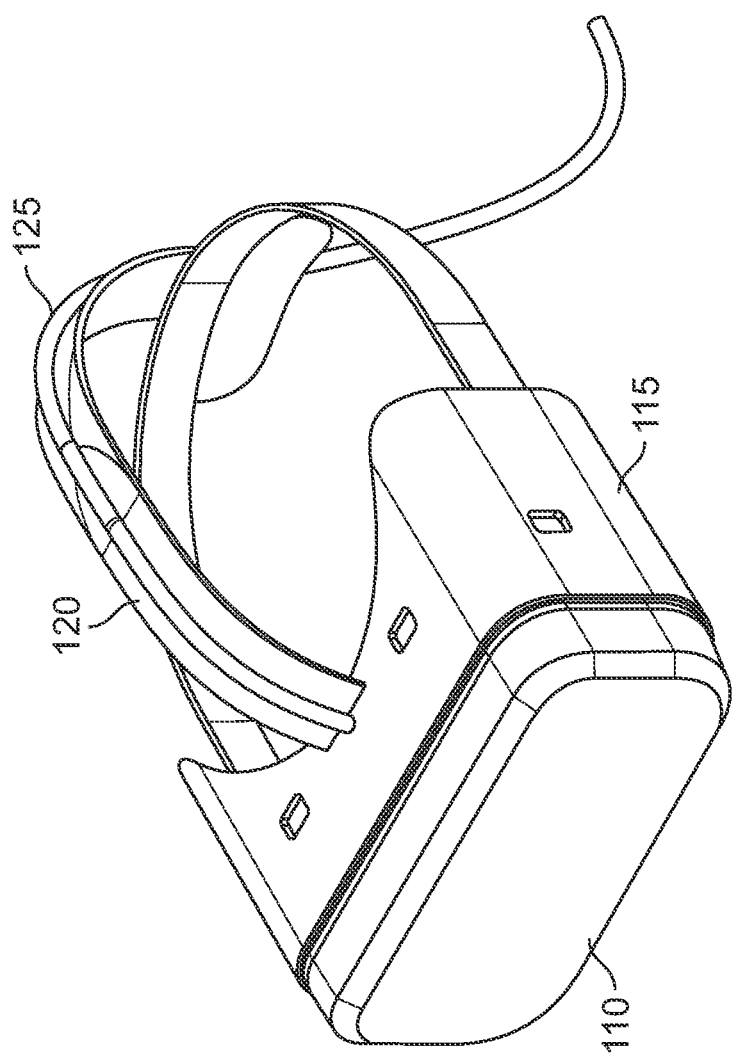

Turning to FIGS. 2A and 2B there is shown the physical structure of a modular headset system 100 that can be used as headset 12 in the system of FIG. 1 and for other purposes. The headset system 100 comprises head mount hardware 105 including an outer frame 115, one or more head straps 120, and an electrical cable 125 that can be used to carry power, control signals, and data as needed in a given implementation.

The head straps 120 can be fixed or adjustable and can be configured in a variety of conventional ways to secure the headset 100 on a user's face. The head straps 120 should operate to allow the system 100 to be fixed on a person's face while spreading the majority of the weight of system 100 on the periphery of the user's head. The portion of system 100 that makes contact with the user's face can contain a face pad, such as a cushion made of breathable cloth, and which can be designed to further distribute the weight of the ophthalmic headset across the face and maintain a center of gravity as close as possible to the neck for comfort and to minimize slipping. In a configuration, there is a circle shaped strap fits into the patient's head and a second strap that patients head. The straps can be adjusted according to patient's head-size, for example by using a gear mechanism which can tighten or loosen the straps automatically or manually.

The headset system 100 further comprises an optics module 110 that can be removably mounted within the outer frame 115 and the housing 130. Optics module 110 contains the various headset equipment components, such lenses, cameras, optical emitters, visual displays, mechanical structures, electronics, and computing hardware and software. These components are contained within a housing 130. Housing 130 is configured in an embodiment to fit securely within the outer frame 115 of the headset and yet be easily removable by a user. Various mechanisms can be used for the removable mounting of the optics module 110 to the headset system 100. In the illustrated embodiment, optics module 110 is secured within the outer frame 115 by a plurality of clips 135 on the optics module housing 130 that engage corresponding apertures 140 in the outer frame 115. Other mounting mechanisms known to those of skill in the art can also be used to removably secure the optics module 110 within the outer frame 115, including screws, spring loaded detents or catches, and other structures.

A port or other interface 145 can be provided in the housing 130 of the optics module 110 to allow for an electrical connection to be made between the optics module 110 and the head mount 105 or other external equipment. The connection can be used to provide power to the optics module 110 and/or to provide a data and control connection. In one embodiment, port 145 contains electrical contacts that engage corresponding contacts on the inside of the outer frame 115 when the optics module 110 is installed. Although one port 145 is shown, multiple separate ports can be provided. In addition, or alternatively, a plug-in cable can be used to connect the port 145 on the optics module 110 to electronics in head mount 105. If a connection to the outer frame 115 is not required, port 145 can be positioned so that is accessible when optics module 110 is seated in the outer frame. A hole in the outer frame 115 can be formed to provide external access to the port 145.

An internal battery can be provided within the optics module 110 in embodiments where power is not supplied through the head mount cable 125. Depending on the configuration and functionality of the optics module 110, the cable 125 may not be needed. For example, the optics module 110 can be powered by an internal battery and communication with external computing systems, such as control system 16, can be provided by a Wi-Fi, Bluetooth, or other wireless connection.

A plurality of optics modules 110 with different functionality can be provided in a preassembled form and respective optics modules can be swapped in and out to provide different functionality for the headset. Various different optics modules 110 are presented herein. Each module 110 can include a built-in computing system with firmware that controls how the module operates and also to support communication with the head-mounted device as appropriate for delivering the relevant imaging or ophthalmic task. The firmware can include functionality for displaying images, controlling electrical, mechanical, and optical components, capturing images, performing image processing routines, and other functionality to support the overall testing system. Offloading various image processing and control functions to the computing system in the module 110 can reduce the data that needs to be exchanged with an external computer system.

Because optics module 110 is removable, the same optics module 110 can be used with different head mount hardware 105 so that, for example, optics module 110 can be switched between head mount hardware 105 sized for an adult and head mount hardware 105 sized for a child. Different types of ophthalmic tests can require different functionality. The system 100 allows a first optics module 110 configured for a first type of test to be removed and replaced with a second optics module 110' configured for a second type of test while using the same head mount hardware 105. As discussed further below, optics module 110 can itself be modular to allow some of the internal equipment, such as lens assemblies and related mechanical structure, be removed and replaced to provide different functionality, e.g., to support different types of eye tests, while allowing reuse of other internal equipment such as the electronics, and computing hardware.

Figure 6:
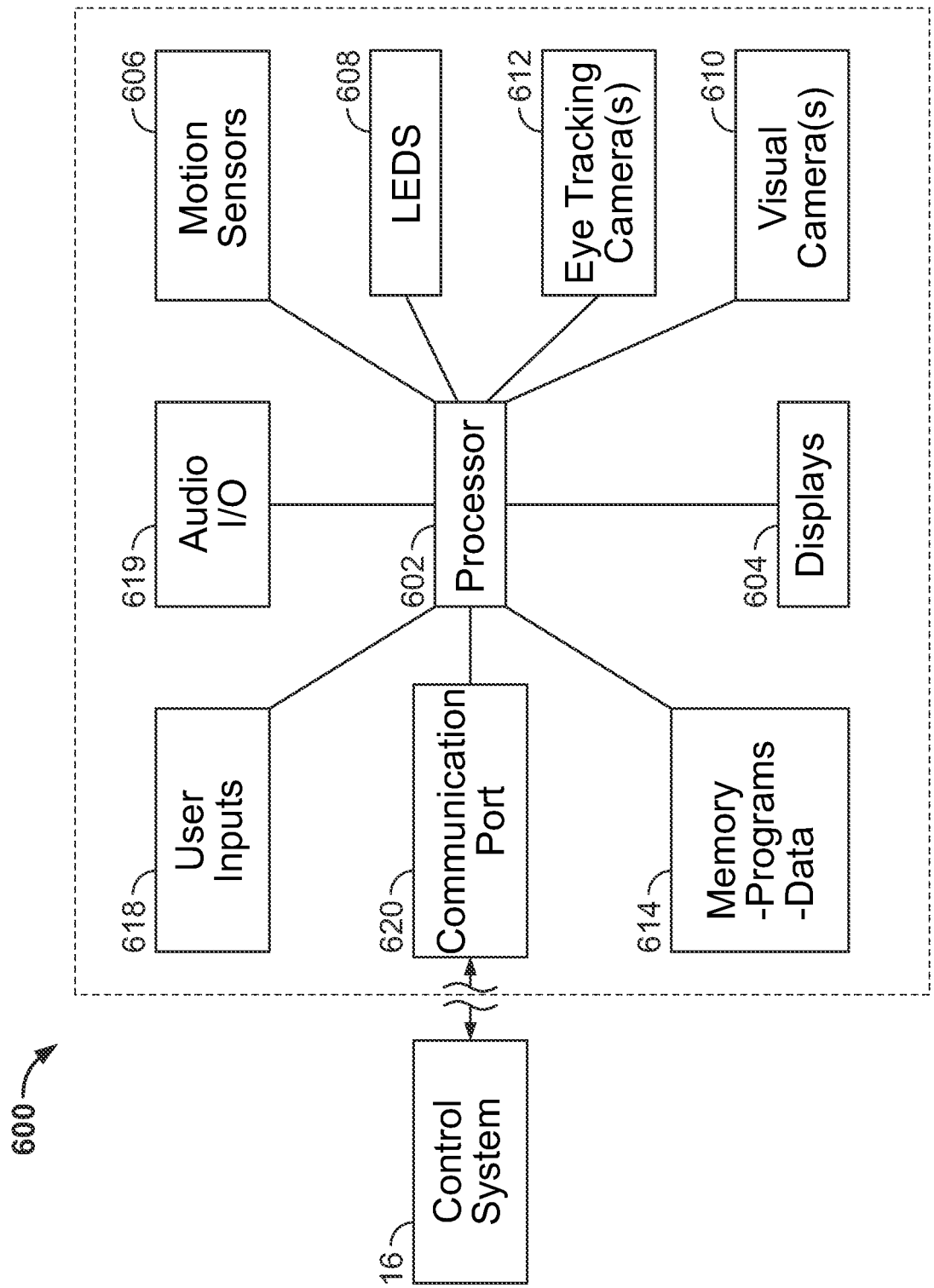
FIG. 6 is a high-level block diagram of the major electronic components 600 that can be provided within an optics module.

Turning to FIG. 6, there is shown a high-level block diagram of the major electronic components 600 that can be provided within an optics module 110 and which can work in conjunction with various additional optical, mechanical, and other components that may also be within the module 110. In an embodiment, the optics module 110 can contain a computer processor 602 and one or more internal visual displays 604, such as OLED or LCD display screens, or micromirror projection display, with one for each eye, and for use in displaying a virtual reality environment as part of an eye examination. The displays can be high resolution displays having 4 k resolution each i.e. 3840×2160 pixels or 4096×2160 pixels. A particular improved design for a digital micromirror display device suitable for mounting in a headset is addressed further below.

Module system 600 can include both a conventional imaging camera 610 as well as one or more eye-tracking cameras 612 (typically four for each eye although fewer or greater numbers could be used). Motion sensors 606 provide measurements allowing motion of the headset to be detected. LED or other light sources 608 can be provided. Infrared LEDs can be used to illuminate a person's eyes for eye tracking purposes. Visible LEDs can be used to signal the person wearing the headset and to illuminate the person's eyes for use in visual light camera imaging.

A digital memory 614 stores computer software executed by the processor 602, such as an operating system and software for administering optical tests as well as storing data used and generated during operation of the system. Various user input devices 618 can be provided, including one or more of a press button, touch screen, toggle switch, dial, or other input mechanism along with audio components 619 to support audio input and output such as a microphone and headphones (or a headphone connection that will link to attached headphones).

One or more communications ports 620 are provided to allow wired or wireless connection to an external device, such as control system 16. The VR module 600 can be configured so that its functionality can be accessed using conventional VR headset interfaces.

Different modules 110 can be specially configured for use in different types of optical exams, such as OCT, autorefractor, and retinal imaging using a miniature Fundus camera. The module 110 can be configured to provide VR environment test simulations or to measure eye color deficits, perimetry of the field of view of the user and perform auto-refraction functions. Each configuration may require different optical, mechanical, and other components. Additional modules 110 can be provided with alternative functionality. While the system is discussed herein in the context of medical testing, different modules can be used for any purpose.

Appropriate internal software or firmware is stored in the memory 614 to allow the processor 602 interact and control the various internal components and communicate with other system components, such as components on the head mount hardware 105 and an external control system 16 or other external computer, and to support in part or full the ophthalmic imaging or other testing functions and return the captured image or other test data. The control and testing software required for the control system 16 or other external device can be preinstalled in an optics module 110. When the external computer is connected to the optics module 110, such as by a cable, the software needed to be run on that computer can be downloaded from the optics module 110. Likewise, an externally connected computer can be used to update the software on the optics module 110.

For a module system 600 that include cameras for imaging the external or internal features of the eye, images can be captured by the module and processed and analyzed to identify potential issues. Captured images can be processed using software such as stitching algorithms, image processing, machine learning, and pattern recognition to generate detailed images of the eye and identify potential issues. Some image capture and initial processing may be done by the processor 602. For example, software in the stored in the memory 614 can be provided to capture the images, perform some initial image processing, and determine when a sufficient number of images has been captured for the particular imaging process at issue. More complex processing, such as stitching and analysis can be done on a separate computer, such as control system 16 or system 20. In an alternative embodiment, the external system 16 or 20 can control the entire imaging sequence with only low-level support provided from the computer components in the module system 600.

The visual displays 604 used to present image tests to a patient wearing the system 100 can have a large color spectrum, such as an OLED or LCD screen or micromirror projection display and have a high resolution. The displays 604 can be used to present multiple images with varying degrees of color to test for color acuity and severity of color blindness. Providing a higher resolution image in pixels per inch can provide enhanced results for visual tests such as the Ishihara test. The displays 604 can also be used to provide perimetry, visual acuity, and Amsler grid testing. Aspects of this are discussed below. The software can be configured to allow one or more of these tests to be run. Test selection can be on-demand and some or all of the tests can be enabled, e.g., by an optometrist, to be run in sequence for a given patient depending on that patient's screening needs.

In an embodiment, the removable optics module 110 comprises separate modular sub-components that can be combined by an end-user (such as a doctor or technician). Each sub-component can provide different functionality. By replacing one or more sub-components the overall module 110 can be configured to support different eye tests that may require separate and incompatible optics.

Figure 3B:
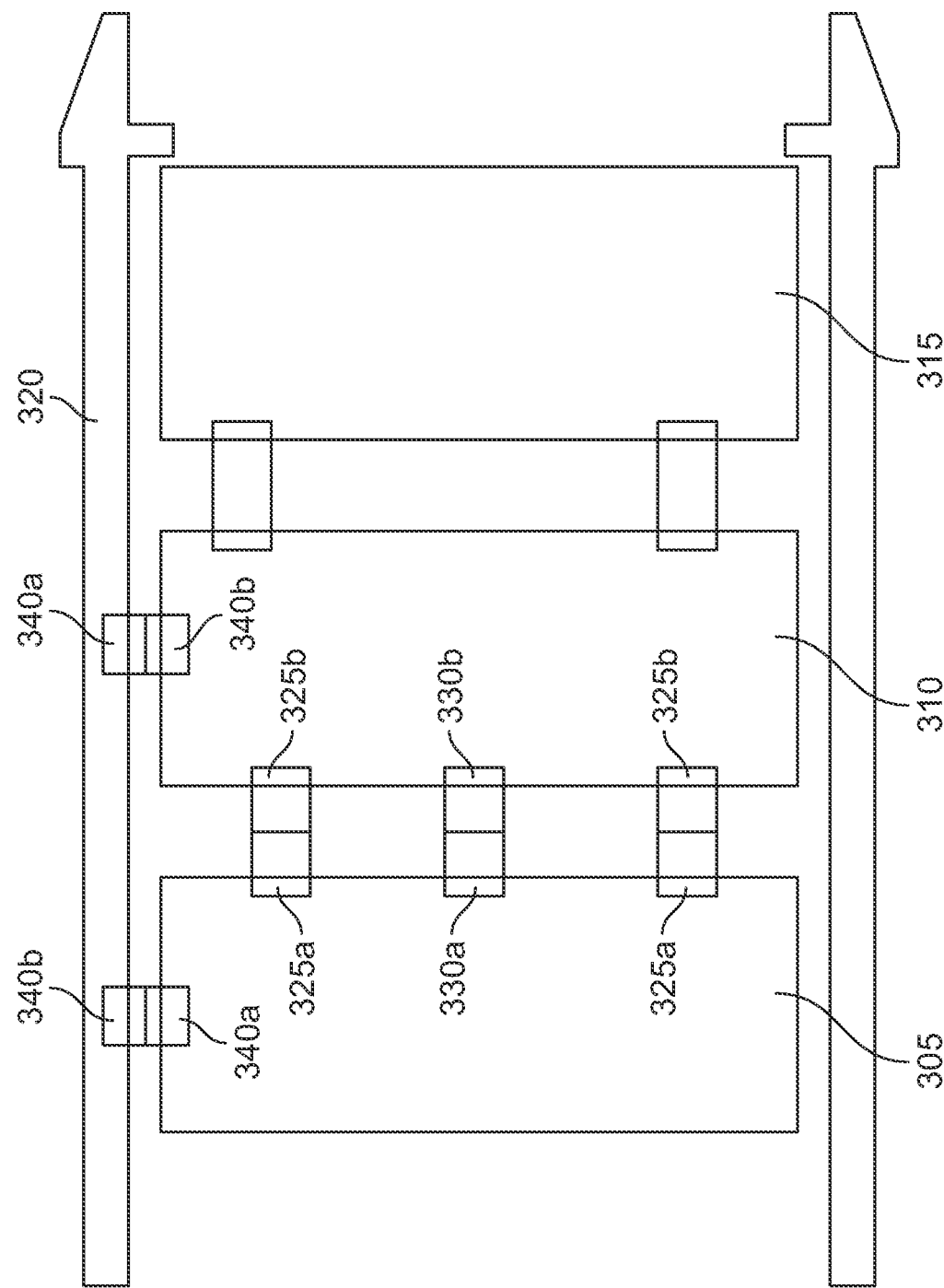

FIGS. 3A and 3B show exploded and an assembled cross-section view of an optical module 300 in an exemplary embodiment having three sub-components 305, 310, 315 mounted in an outer shell or housing 320 configured to mate with the outer frame 115 of the head mount 105. The of sub-components and the functionality of each can vary.

In an embodiment, the rear component 305 comprises the main computer system components, such as the processor 602, program and data memory 614, and wireless and wired communication modules 620. Sub-component 310 comprises video displays 604, such as OLED or LED displays, and can include other optical components like IR emitters 608 and eye-tracking cameras 612. Associated optics, such as lenses for the cameras and displays can also be included.

Sub-component 315 comprises additional mechanical, optical, and/or electrical elements, such as filters, additional lenses, cameras, etc., that are suitable for the particular eye test or other use for which the optics module 110 is to be used.

Mechanical alignment and connection structures can be provided to allow adjacent sub-components to be properly aligned and directly and removably coupled together. Electrical interfaces can also be provided on the sub-components to allow direct power and data communication between adjacent sub-components, for example to allow the computing circuitry in the sub-module 305 to drive video displays in sub-module 310. Suitable mechanical and electrical interfaces for these purposes will be known to those of skill in the art.

In one configuration opposing mechanical structures 325*a* and 325*b* are provided on mating surfaces of adjacent sub-components, such as on the adjacent forward face 305*a* of sub-component 305 and on the rear face 310*a* sub-component 310. The mechanical structures 325*a*, 325*b* can be configured to mate for alignment purposes, such as in a tab/slot configuration. They can be further configured to mechanically engage each other, such as via a spring-biased snap-in member, to help hold adjacent sub-components together.

Mating electrical interfaces 330*a*, 330*b*, such as electrically conductive pads and spring-loaded pins, can be provided on opposed mating surfaces of adjacent sub-components to provide direct data and power communication between the adjoining sub-components. Other data connections, such as optical data emitter/detectors interfaces may also be suitable for data communication. Alternatively, or in addition, connections between sub-components in a module 300 can be indirect through the housing 320. Connection circuitry 340*a* can be provided on one or more sides of a sub-module that will electrically connect with corresponding connection circuitry 340*b* on the interior of the housing 320. Connection circuitry 340*b* in the housing 320 can be provided at fixed positions or provided an extended interface, such as a data and/or power bus, to support a connection from a sub-component located at a variety of positions within the length of the housing 320.

Different sub-component configurations are possible. For example, the computer system components and display components can be combined in a single sub-component. In some configurations, a sub-component may be usable by itself and also have additional functionality added via further sub-modules. For example, a dual-display system with a liquid lens optics train and eye tracking can be provided for use in some types of testing, such as a visual field test. An add-on sub-module can be fitted in place to provide additional functionality to allow different testing to be done. In one configuration, a miniaturized fundus camera, such as disclosed separately below, can be added for use in retinal imaging.

The housing 320 can have internal stops or other structures that allow mounted sub-modules to be placed at a known position along the length of the housing 320 and by extension in a predetermined position relative to the head mount hardware 105, and thereby a user's face, when the overall module 300 is mounted therein. Spacers can be added between or in front of sub-components as needed to position them correctly within the housing 320.

Each sub-component can have an assigned function code identifying its purposes and that can be read by the computer sub-component 305 or other systems, such as in the housing 320 or control system 16 to allow software to know which sub-components are installed and thereby what testing functionality is available. The system can automatically detect modules that are installed and signal the appropriate software to be activated, e.g., software for performing fundus camera imaging, visual field testing, OCT, etc.

Figure 4:
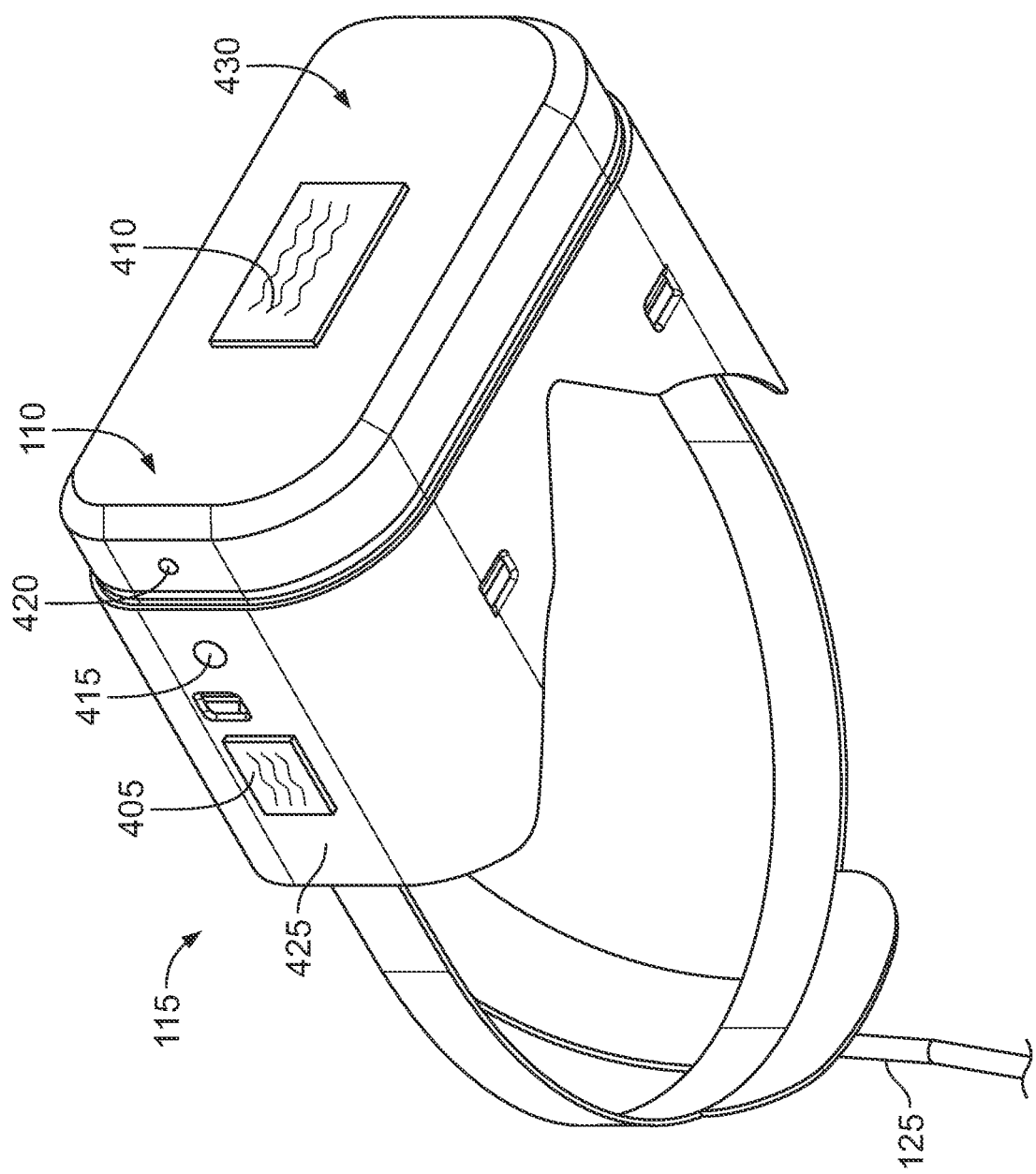
FIG. 4 illustrates a headset system with various external user inputs and outputs mounted thereon.
Figure 5:
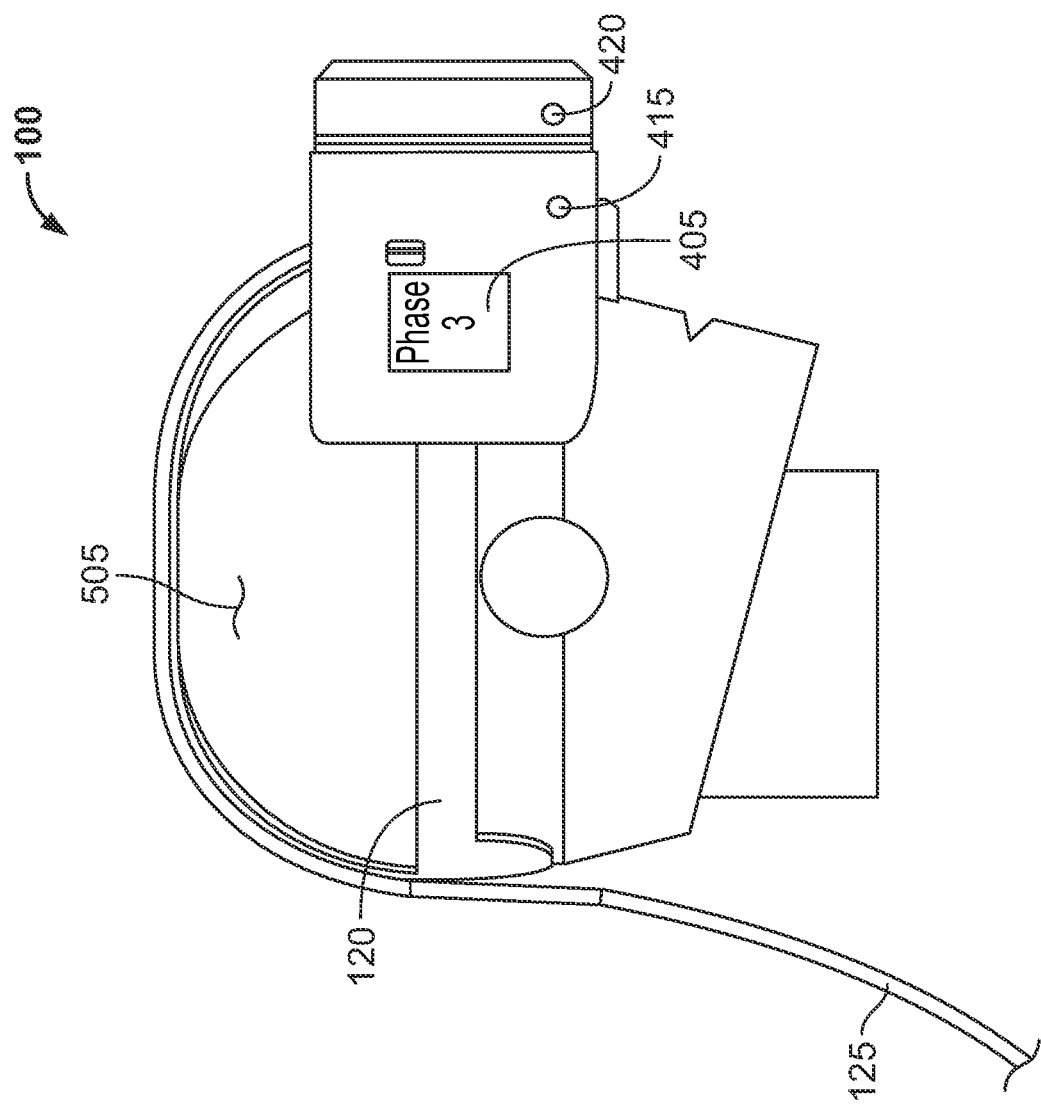
FIG. 5 shows the headset of FIG. 4 being worn by a user.

In addition to or alternatively to separate user input systems (such as input 22 of FIG. 1), user input and outputs can be provided on the exterior of the headset system 100. FIG. 4 shows a headset system with various external user inputs and outputs mounted thereon. FIG. 5 shows the headset of FIG. 4 being worn by a user. With reference to FIGS. 4 and 5, one or more input buttons 415 can be provided on the outer frame 115. The signals from the buttons 415 can be coupled to the computer system within optical module 110 (including in the form of module 300) through port 145 or other connection or coupled to an external computer working in conjunction with the system 100. In addition, or alternatively, one or more input buttons 420 can be provided on the outside of the optics module 110 and the signal from those buttons 420 processed by circuitry within the optics module 110. Buttons 415, 420 can be mechanical push-button switches, touch sensitive devices such as capacitive or pressure-sensitive areas, or other forms of input.

According to a further feature, a small video display 405 can be formed on an outer surface 425 of the outer frame 115 of head mount 105. While the screen of display 405 is shown on a side surface, it could also be positioned on a different surface of the outer frame 115, such as a top surface. In addition or alternatively, a separate display 410 can be positioned with its screen on the outward-facing surface 430 of the optics module 110. The display screens 405, 410 can be touch-screen devices and, in this configuration, may be used instead of or in addition to separate buttons 415, 420.

Displays 405, 410 can be driven by computer system within optical module 110 by a connection made through port 145 or other connection or coupled to and driven by an external computer working in conjunction with the system 100, such as through cable 125.

The displays 405, 410 can be used to output informational messages for system diagnostics, e.g., for the optical module 110. In one configuration, when a new optical module 110 is inserted, one or both of the display screens 405, 410 can provide an output indicating that each component in the optical module 110 is functioning properly and has established the required a power and data connections, such as to the components in the head mount 105.

The displays 405, 410 can also be used to output informational messages related to a visual test sequence in progress. In an embodiment, testing software is configured to indicate the test being administered and the stage of the test. Other information, such as a visual representation of the display being shown the patient, can be mirrored on the same or separate display. This allows a doctor or other person to easily monitor the testing progress of a patient without having to access a separate computer connected to the headset.

The displays can also be used to output information related to the configuration of the current module. One display, such as the front, can be used to output instructions on how to operate the display optics assembled inside of the removeable module while the second display, such as the side, can output operational data, such as power and battery level, volume adjustment, and title of test the unit is configured to execute.

The displays can also be used as touchscreen control devices allowing a doctor to alter various configurational features, such as the test being run or the position of adjustable optical features within the headset. For example, controls to adjust the interpupillary distance of lens elements can be provided. Images from a camera within the headset can also be displayed on the screen so a doctor can see the patient's eye during the course of an exam.

FIGS. 7A-7D show a particular embodiment of an optical module 700 suitable for use in displaying a VR or other visual environment as part of an eye exam and that can be fitted into head mount hardware 105 or otherwise incorporated into a head mounted VR display. With reference to the figures, module 700 has a rear frame or housing 702. Set into the rear frame is a motherboard 704 that contains the computer circuitry used to control the various components in the optical module 700 and provides communication with external devices. Left and right images are provided by a pair of visual displays 706a, 706b. In a particular configuration the displays 706a, 706b have edge connectors 707a, 707b that connect to a corresponding interfaces 705 positioned on an edge, such as the bottom edge, of motherboard 704 Interfaces 705 can comprise connection slots 705a that are parallel or perpendicular to the surface of the motherboard and that are configured to receive the corresponding directed edge connectors 707a, 707b on the display to the displays 706a, 706b to be easily connected and mounted very close to and parallel with the motherboard 704. Instead of a rigid form factor the male edge connector can be comprised of a flex a cable.

A pair of lens assemblies 708a, 708b are mounted in a frame assembly 710 and are configured to form virtual images viewable by a person wearing the headset of the images on the corresponding displays 706a, 706b, which images appear to the person to be further away than the actual displays and larger than the images shown on the displays. Various types of lens assemblies for each lens assembly 708a, 708b, can be used including a single lens, a compound lens structure, and a regular or hybrid Fresnel lens. An interpupillary eyepiece can be placed in front of a respective Fresnel lens and which will focus the display for a user. In place of a display, a micromirror display can also be utilized. While two displays 706a, 706b and corresponding lens assemblies 708a, 708b are shown, some embodiments may only include a single display and/or a single lens assembly. The lens assemblies 708a, 708b can be fitted into a frame assembly 710 comprising respective display lens frames 712a, 712b which mount on a front frame 714. The various components 704, 706, 708, 710, 712, 714 are mounted to and/or within an outer frame 716 that can be removably mounted in an outer frame 115 of a head mount 105.

Various other components can also be included in the optical module 700 including LEDs and eye-tracking cameras. These components can be mounted on the circuit board 704 or to other elements. For example, eye tracking cameras could be mounted inside the rear frame 702. The eye-tracking system can be provided to collect data from a user's eyes and generate an image of each eye from cameras in the tracking system. LEDs can be mounted on portions of the frame assembly 710. Electrical connections between these components and driving circuitry can be provided in a manner known to those of skill in the art.

The displays 706a, b can be independently controlled. Certain exams will require both displays to be on. Other exams focus on only a single eye and require one display to be on while the other is off. The eye-tracking features and other functionality for the off eye could remain on or be disabled as well depending on the testing being done.

In a particular embodiment each lens assembly 708*a*, 708*b* comprises a liquid lens component that has a focus which can be electronically adjusted. An electrical connection is provided to lens driving circuitry 709 (not shown), which can be provided be on the motherboard 704 or elsewhere. Lens driving circuitry 709 provides the control signals used to adjust the focus of the lenses 708*a*, 708*b*.

Figure 7A:
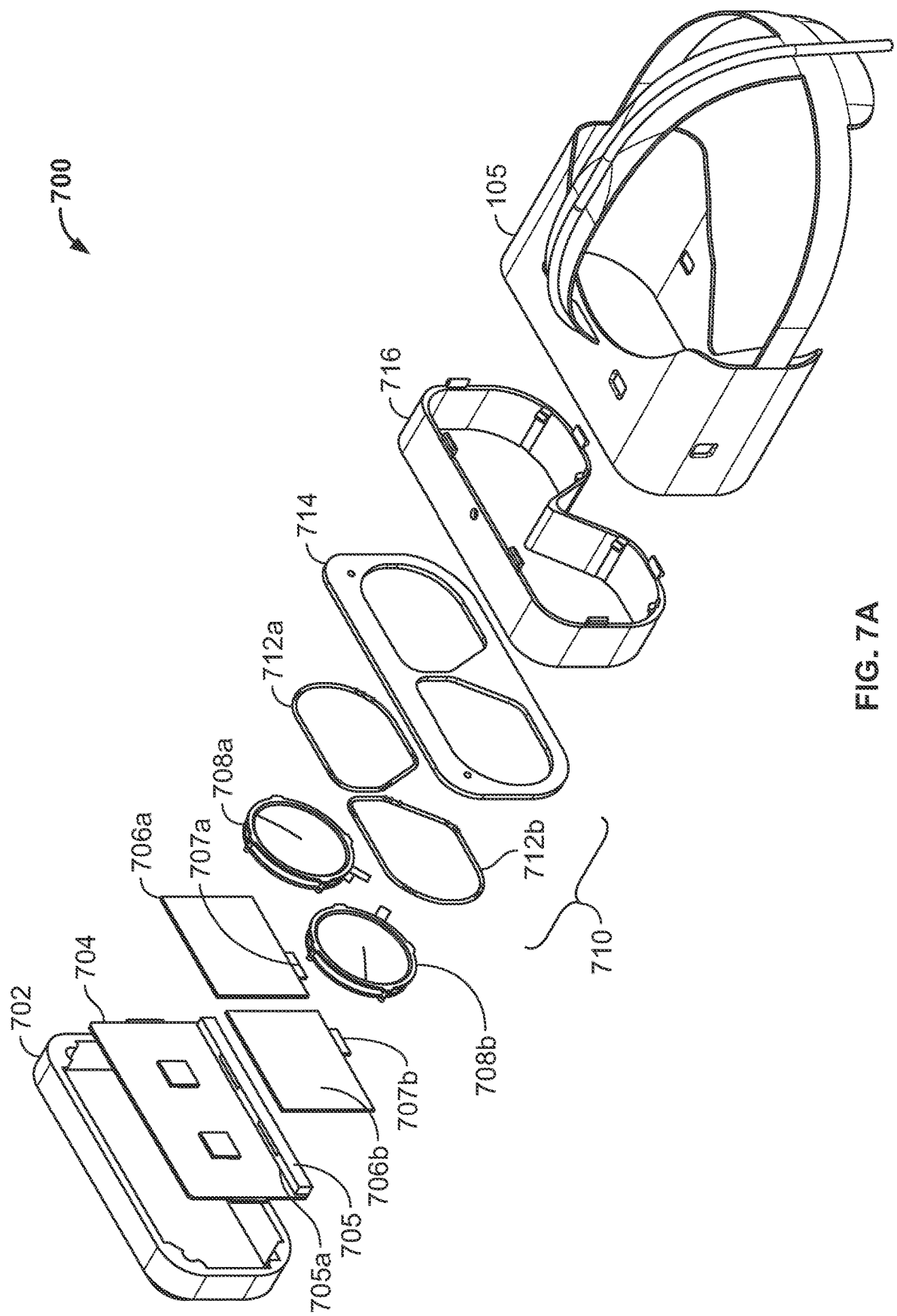
FIGS. 7A-7D show a particular embodiment of an optical module suitable for use in displaying a VR environment as part of an eye exam.
Figure 7B:
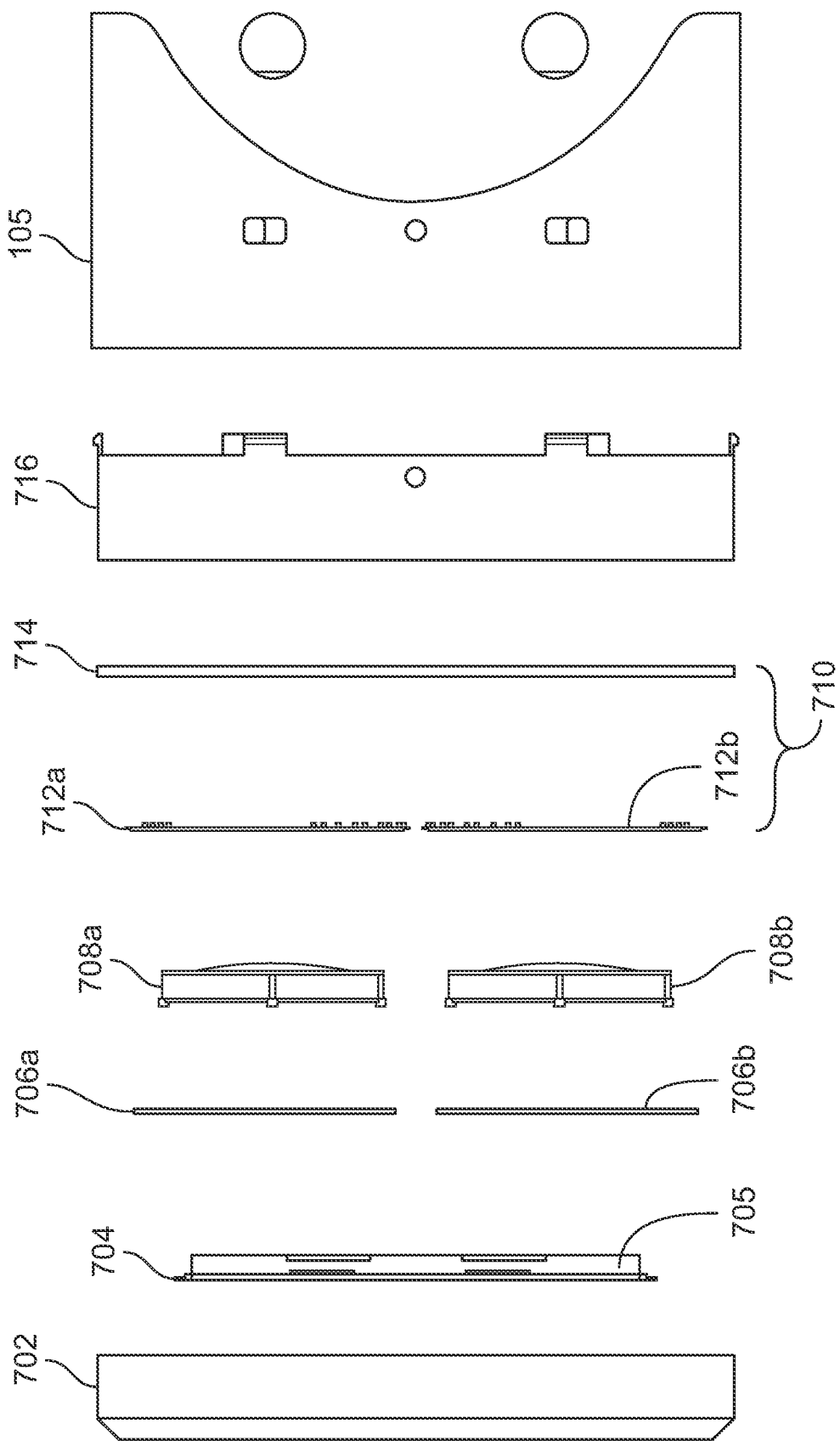
Figure 7C:
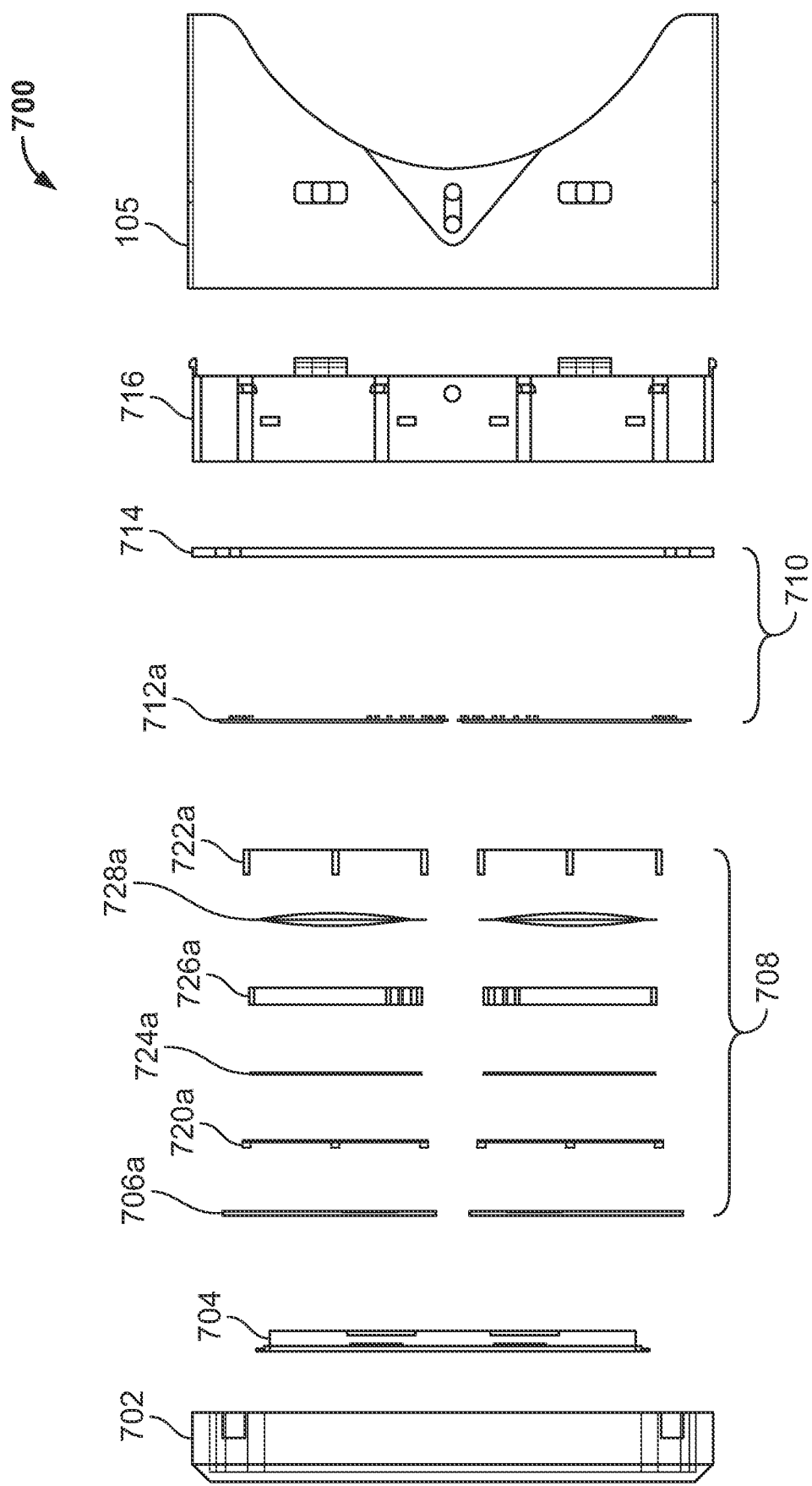
Figure 7D:
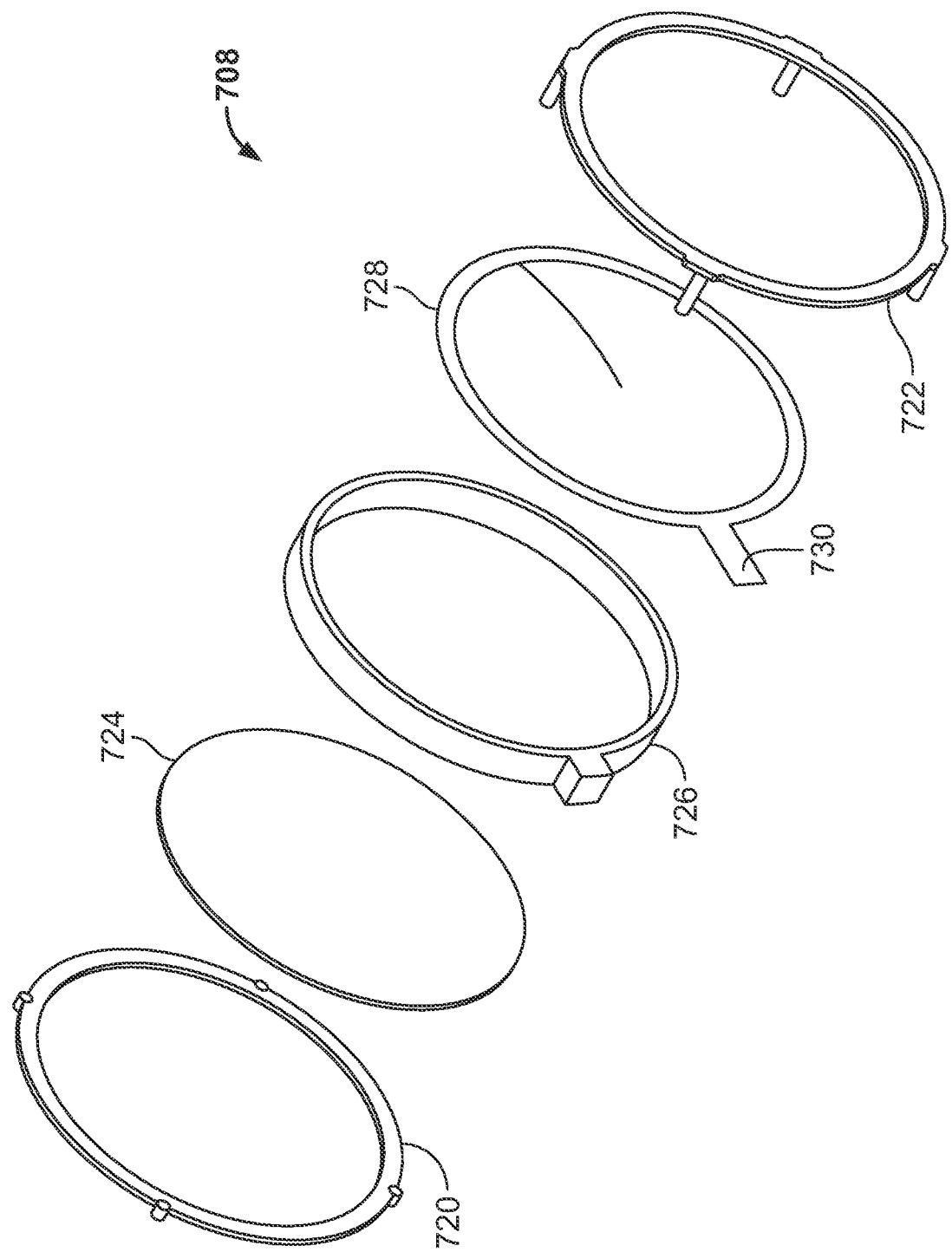

A liquid lens assembly comprising left and right lens assemblies 708*a* and 708*b* is shown in FIGS. 7C and 7D. The liquid lens assembly includes mounting rings 720, 722, a static lens 724 which can be a Fresnel lens, a spacer 726, and a variable focus liquid lens 728 with a ribbon cable or other wire set 730 for carrying electrical signals to control the liquid lens 728. Other lens configurations can be used as well.

By varying the focus of the liquid lens, various static and interactive optical vision tests can be performed. Adjusting the liquid lens can also allow the VR system to be used without requiring a user that has poor eyesight to wear glasses or contact lenses. By adjusting the focus of the liquid lens 708*a, b* the apparent distance of an image shown on a corresponding display 706*a, b* can also be changed. This change in apparent distance is sensed differently than distance perception due to image parallax between two images of a 3D display. By providing two separate visual cues to virtual image distance, the immersion aspect of a VR display can be enhanced. By way of example, a 3D VR image can be generated and displayed on the dual displays 706*a, b* with the position of 3D elements in the left and right image selected to provide a desired apparent distance based on parallax. Eye tracking cameras in the headset can be used to can determine what 3D element the user is looking at. The virtual distance along the Z axis from the user to that 3D element can be determined and the focus of the liquid lens 708*a,b* dynamically adjusted so that the 3D element being looked at appears to the user to be at that virtual distance based on eye focus as well as parallax.

Figure 8:
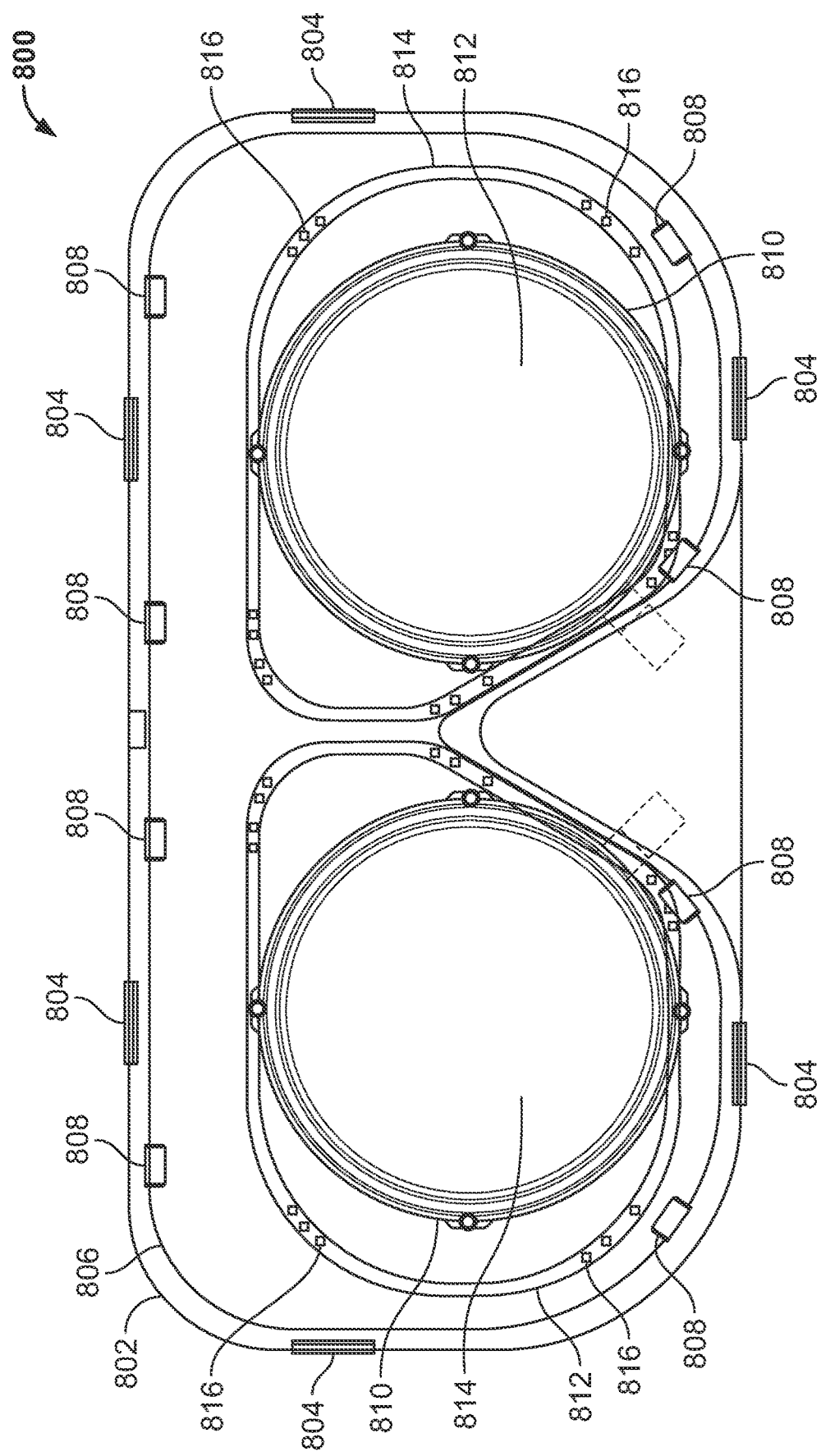
FIG. 8 shows a configuration of an optical module viewed from the user-facing side and that can be inserted into a headset mount.

Turning to FIG. 8, there is shown a particular configuration of an optical module 800 viewed from the user-facing side and that can be inserted into a head mount, such as head mount 105 shown in FIG. 1 and which could be an embodiment of the assembly shown in FIGS. 7A-7D, a modular optical module 300, or other configuration. Optical module 800 has an outer housing 802 with clips 804 for connection with a head mount 105. Inner housing 806 is fitted into the outer housing 802 and has a plurality of eye-tracking cameras 808. In the embodiment shown, there are four cameras 808 for each eye. Each camera is positioned so it can image a respective quadrant of the user's eye. A lens assembly 810, is mounted in a frame assembly that can include left and right lenses 812 and a front frame 814. Lenses 812 can comprise a compound liquid lens assembly such as discussed above with respect to FIGS. 7A-D.

A plurality of user-facing LEDs 816 are mounted in the module 800 and can be used to illuminate a user's eyes for eye tracking purposes and for other reasons. Clusters of LEDs can be arranged along the periphery of the frame assembly. For example, OLED and infrared LEDs, white light LEDs, and blue light LEDs. In one embodiment, the LEDs are controlled as a group. In a different embodiment, each cluster of LEDs and/or each LED in a cluster can be independently controlled.

Figure 9A:
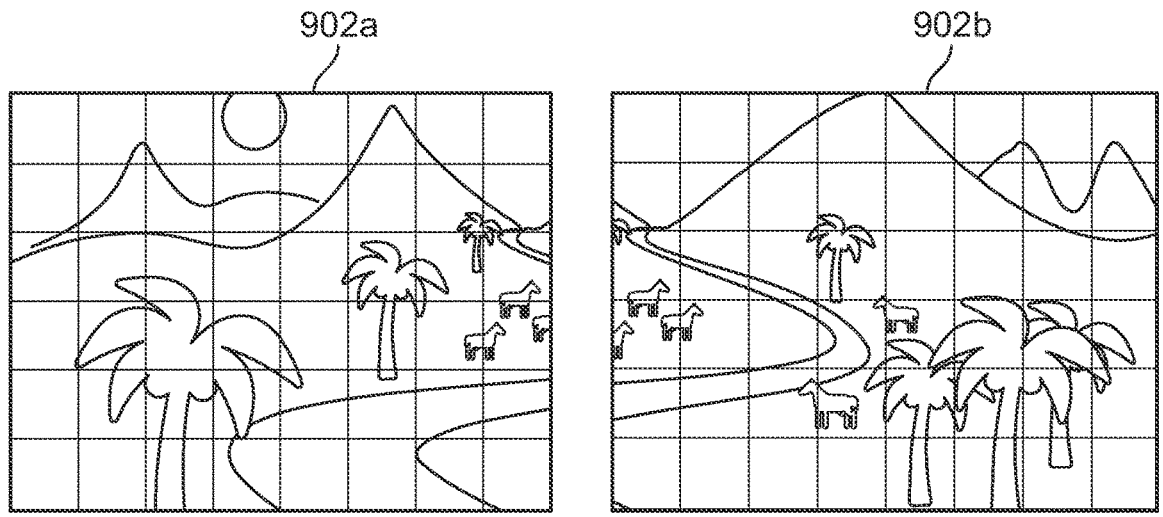
FIGS. 9A and 9B illustrate sample images presented on headset displays as part of a foveated rendering process.
Figure 9B:
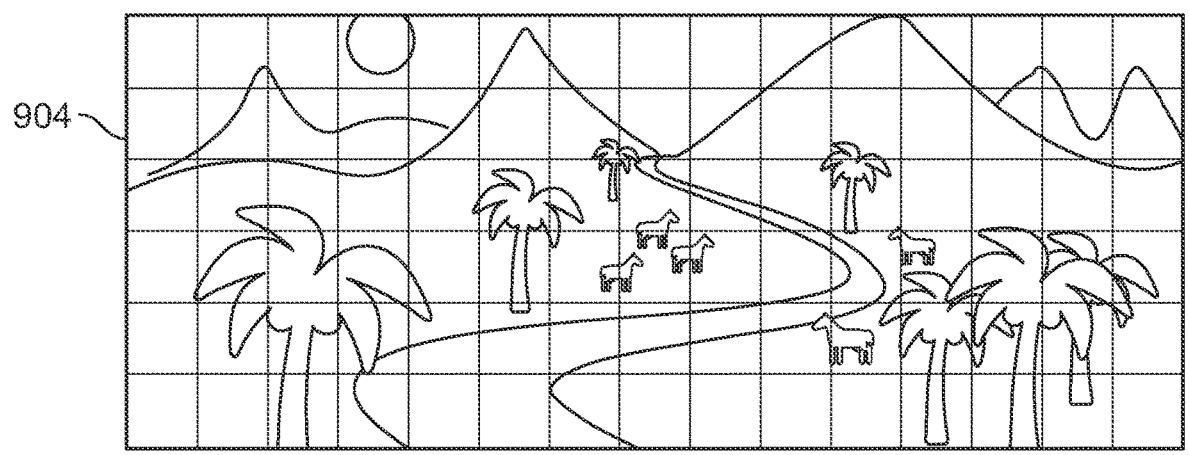

FIGS. 9A and 9B illustrate, respectively, sample separate and combined images on displays 902*a*, 902*b* each with an image shown on it and where each image is intended to be viewed by the user's corresponding left or right eye when they are wearing the headset. The combined image 904 in FIG. 9B represents how the separate images in FIG. 9A could be seen by a normal user as fused together into a single VR environment scene. The images can be 3D or can reflect a flat scene at a set apparent distance from the viewer.

Software controlling a VR headset, such as the headset system 700 shown in FIG. 7A, can be used to present images like those of FIGS. 9A and 9B for color vision testing in a virtual reality environment. Isolating a specific eye can be done by turning off one of the display screens allowing for a series of eye tests to be applied to one eye while the other eye only sees a darkened screen. An internal opaque baffle running vertically between the left and right image and optical assemblies can be provided on the user side of the headset to isolate the left and right images screens so that each eye of a person wearing the headset is only able to see images presented by the corresponding display. The baffle can be removable and mounted using hook-and-loop or other fasteners or sized for a friction fit and used when the headset is used for tests that requires eye image isolation. In one configuration the baffle can be built into a removable forward cushion mounted to the user facing side of the headset. When a series of optical tests are being run, the software can be configured to prompt the user to insert the baffle before eye tests that require eye isolation are executed and to remove the baffle on completion of those tests before additional eye testing is done. Data from cameras within the headset, such as eye tracking cameras 612, visual cameras 610, or other sensors can be used to determine or signal whether or not the baffle is present. The testing software can then use the state of this value to determine whether a given test can be properly run.

In the example image of FIGS. 9A and 9B the images represent a flat scene. The system could display the images with a particular overlap. The amount of overlap between the images 902*a*, 902*b* can be a function of the apparent distance the virtual image seen by the user is to have. In one testing scenario, and as discussed above, the liquid lens focus can be adjusted so that in addition to providing a 3D depth cue based on parallax or degree of overlap between the images, the apparent distance of the virtual image based on eye focus can be adjusted as well. The overlap between the displayed images could also be adjusted to test the ability of a user to fuse two images into one.

In an embodiment suitable for use in VR headsets, a foveated rendering process is applied by the software and/or firmware that generates the images shown on each display in the headset. Images from one or more eye-tracking cameras 612 mounted in the headset are processed using conventional techniques to determine where in each image the user's gaze is directed. The area of each image where the user's pupils are directed are rendered at a high resolution, such as at or near the maximum resolution of the display screen. The peripheral parts of the image where the pupils are not directed are rendered at lower image resolutions in comparison to the center of gaze.

The foveated rendering can shift with the location of the pupils or where the user's gaze is directed at on the screen. The system can be configured to receive input from the eye-tracking cameras 612 at a predefined rate and the image refreshed at that same rate with foveated rendering. The images can be displayed repeatedly, such as at 60 to 90 Hz, which rates may equal or be greater than the predefined rate. The decrease in image resolution based on distance in the image from the point of user gaze outward can be varied in a number of ways, such as via a smoothly varying or stepwise function. Resolution can be decreased in a circular pattern, a rectangular pattern, or otherwise as appropriate and desired.

The foveated rendering allows for a more efficient display system because system resources are not required to generate the entire image at a high or the highest resolution level. Resources needed to generate and display a high-resolution image are used for the areas in the image that a user is looking directly at and which will be seen in high resolution. Images along the periphery of the user's view are rendered at a lower resolution and require fewer system resources to generate. The resources needed to display the complete image are therefore reduced. This can allow the system, e.g., to be implemented using a slower processor and/or implemented to provide images at an increased frame rate than would be possible if the entire image were rendered at full resolution. Foveated rendering can be used for various visual testing scenarios. It can also be used in other VR environments in which complex visual displays, such as interactive 3D environments, are rendered on a continual basis.

Figure 19A:
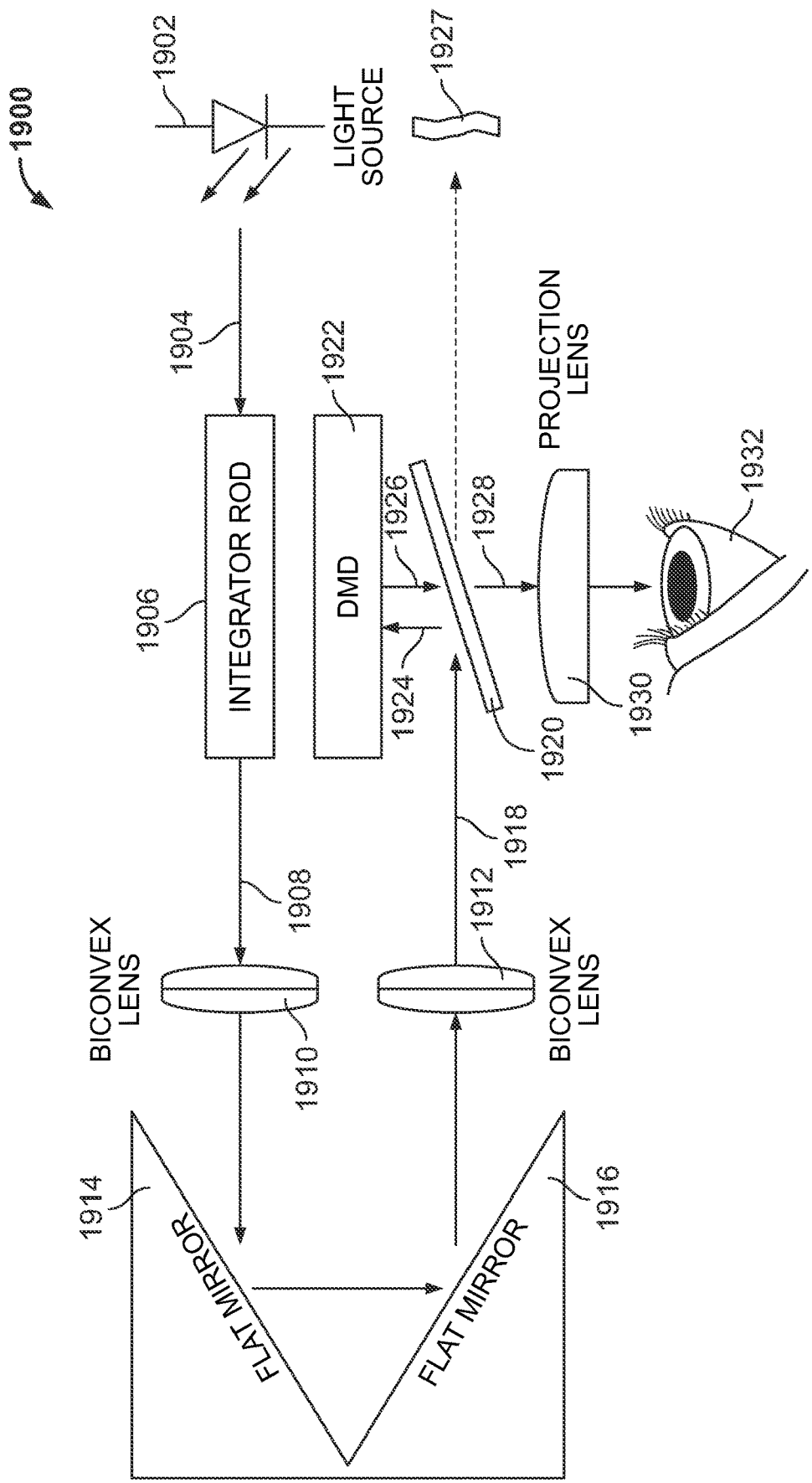
FIGS. 19A-19C illustrate embodiments of a retinal image display incorporating a digital micromirror device and that can be used in a headset assembly as disclosed herein.
Figure 19B:
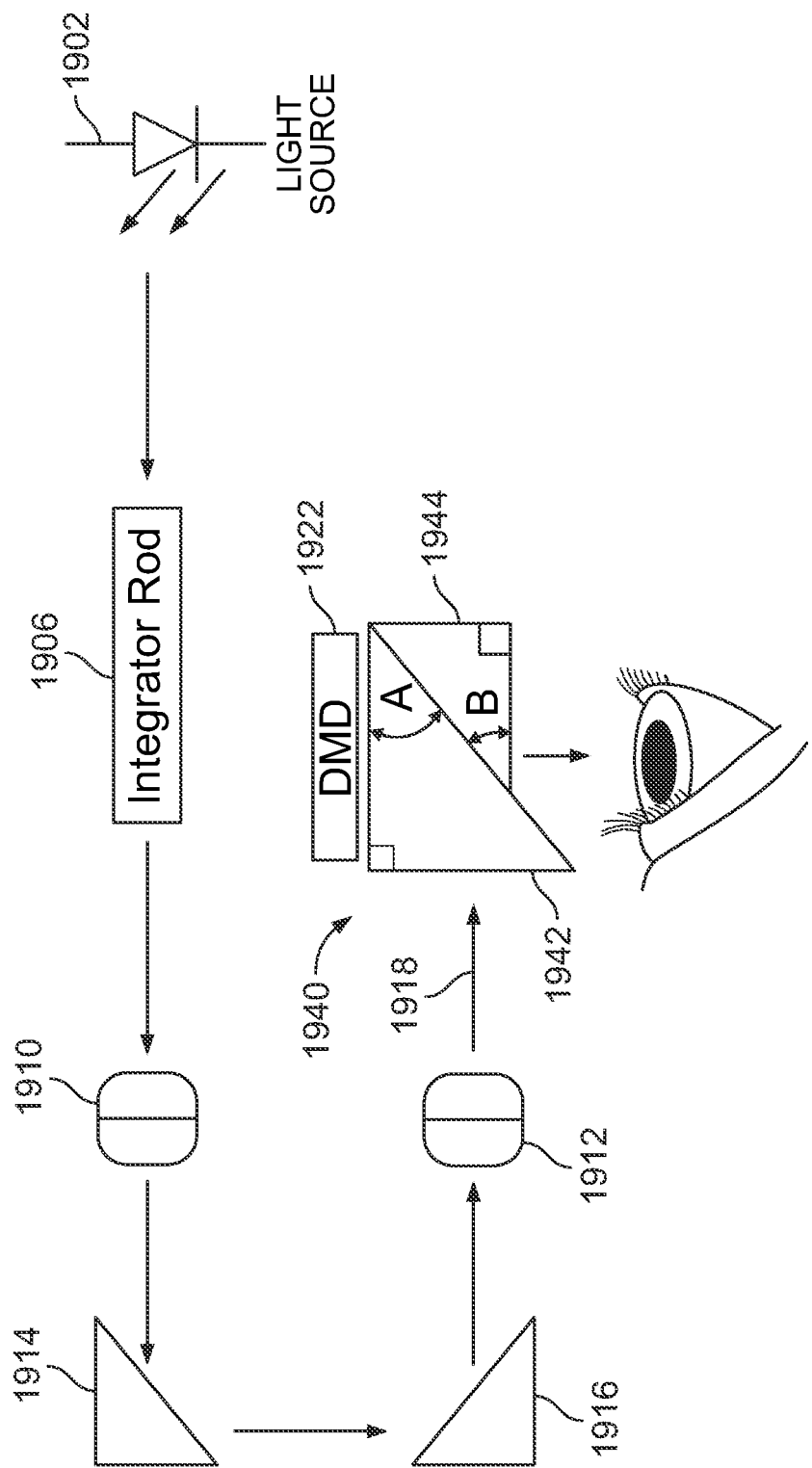

Turning to FIGS. 19A and 19B there are shown improved designs for a retinal image display (RID) incorporating a digital micromirror device (DMD) and which can produce a virtual image having a high pixel density and large field of view. The RID can be made small enough to be incorporated in a VR style headset for use in eye testing as specifically addressed herein.

FIG. 19A shows a first embodiment of a RID 1900. A light source 1902 produces light in a variety of colors and can be controlled by an external control circuit (not shown). Light source 1902 can comprise a plurality of LEDS including one or more of red, green, blue, and white light emitters. Other light sources could be used instead. Light 1904 produced by light source 1902 is directed into an integrator rod 1906 which operates to homogenize the incoming light 1904 and produce a rectangular beam of light 1908 having a predefined aspect ratio. A conventional integrator rod can be used. In a particular embodiment, the integrator rod is between ½ and 1 inch long, such as ⅝ inch, and has a height and width of between ⅛ and ⅜ inch, such as height and width of ¼ inch each to output light with a square cross section. The dimensions of integrator rod 1906 can be selected to provide exit light having an aspect ratio compatible with the micromirror device being used.

The light beam 1908 exiting integrator rod 1906 is focused using one or more lenses, such as biconvex lenses 1910, 1912 to produce focused light beam 1918. To reduce the overall length of the RID 1900, a pair of opposed fold mirrors 1914, 1916 can be used to redirect light exiting the first lens 1908 to the second lens 1910. The lenses 1910, 1912 can be oriented so that their respective optical axes are parallel to each other. The fold mirrors 1914, 1916 can be mirrors. Alternatively, mirrors 1914, 1916 can be replaced with a triangular prism with its flat face oriented perpendicular to the entering light.

Focused light beam 1918 is directed at a beam splitter 1920, such as a partially reflective mirror, that redirects a portion 1924 of the light beam to the reflective active face of a DMD 1922. The portion of the light 1918 that is not directed to the DMD exits the beam splitter 1920 in a different direction. A light absorbing baffle 1927 can be provided to absorb this extra light to prevent internal reflections from impacting the image as viewed. The beam splitter 1920 can be a plate with a thickness of 0.5 to 0.55 millimeters and be positioned such that incoming incident light makes approximately 30 to 40 degree angle with reflected light that reflects from a DMD device.

Figure 19C:
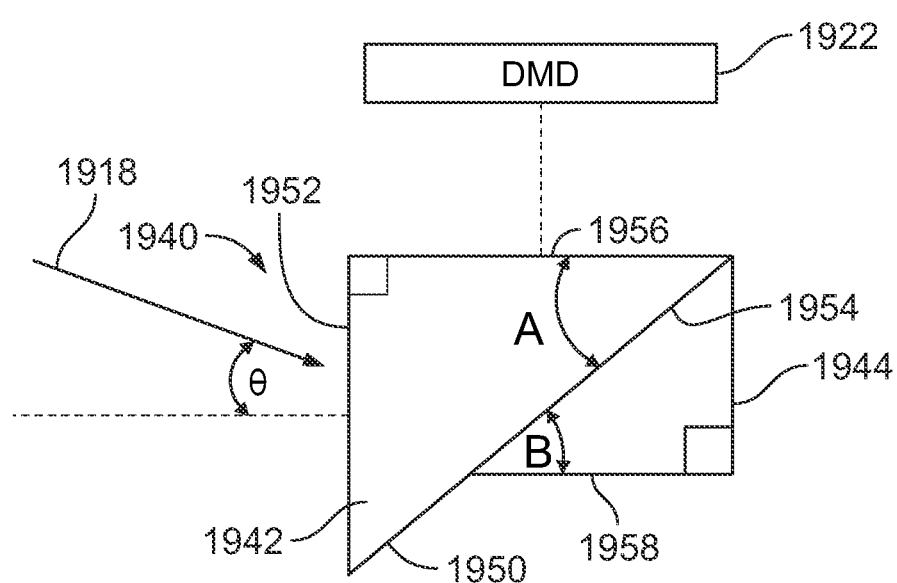

DMD control circuitry (not shown) is used to control the micromirrors of the DMD to modulate the incoming light to produce the desired image. Conventional DMD modules are commercially available and can be used, such as a DMD chip with a 0.66-inch diagonal micromirror array having 5.4-Micro Micromirror pitch and producing an image in 4K UDH resolution (840×2160 pixels). The DMD modulated light is reflected back towards beam splitter 1920 and a portion 1928 passes through and enters a projection lens 1930 which focuses the light as appropriate for projection into the eye 1932 of a viewer. Advantageously, system 1900 can produce immersive near eye display of a virtual image with a large field of view having a range of 40 degrees to 200 degrees FIG. 19B shows an alternative RID module embodiment in which the beam splitter 1920 comprises a total internal reflection (TIR) prism assembly 1940. A further view of prism assembly 1940 is shown in FIG. 19C. Prism assembly 1940 comprises a pair of right-angle prisms 1942, 1944. Prism 1942 has a prism angle A. The hypotenuse 1950 of the first prism 1942 is adjacent the hypotenuse 1954 of the second prism 1944. The prisms 1942, 1944 are comprised of different optical materials having different angles of diffraction. Prism 1942 has an index of refraction Na and prism 1944 has an index of refraction Nb.

Prism assembly 1940 is positioned so that the incoming light 1918 strikes the base side 1952 of prism 1942 at an incident angle θ in relative to a line perpendicular to base 1952 Light exits the side 1956 of prism 1944 at an angle θDMD relative to a line perpendicular to the active mirror surface of DMD 1922.

A TIR prism assembly 1940 prism (1940) directs incoming or incident light that strikes the surface (1942) at an angle relative to an axis that is perpendicular to the surface. Following entry, the incident light strikes the reflective-transmissive surface 1950 of prism 1942 (1950) which then is transmitted transmits out of the prism 1942 TIR prism (1940) onto the DMD 1922 (1922). Light rays are then reflected from the DMD (1922) back towards the TIR prism assembly 1942 and through surface 1956 (1940), transmitted through the surface (1952) and into the TIR prism (1940). The reflected light is then transmitted through the interface between hypotenuse side 1950 of prism 1942 and hypotenuse side 1954 of prism 1944. s 1950 and 1954. The transmitted light passes through prism 1944 and exits through enters 1956 and is then transmitted through the surface 1958 to exit the TIR prism assembly 1940 where it can be directed towards the eye.

Corners of the TIR prism are to be right angles (90 degrees) while angles "A" and "B" are to be complementary angles summing to 90 degrees and can vary depending on the orientation of the incident and the physical positioning of the DMD 1922. Appropriate configurations of the TIR beam splitter 1940 will be known to those of ordinary skill in the art. (1922).

The RID module, such as comprising a design as shown in FIGS. 19A and 19B, can be an integrated part of the overall VR headset or provided within a removable optical module 110 such as shown in FIG. 2A. Within the optical module 110, the RID can be packaged as a removable submodule, such as submodule 310 of FIG. 3A.

The brightness of an LED-illuminated projection system can be easily adjusted by modulating the LED current intensity. A pair of RID display units can be provided in the headset, one for each eye, and where a user will see just one image.

Mechanisms can be provided to adjust the relative position of the two RID units as viewed by a user in accordance with interpupillary distance (IPD) between the center of the pupils of the two eyes. Adjustment can be manually, such as via rotary knobs located on or adjacent to the headset or electrically controlled by means of a small servo motor located within the virtual reality headset. Cameras in the headset, such as eye tracking cameras at known locations in the headset, can be used to capture data from which the IPD can be calculated. The position of the RID display units can then be automatically adjusted in response. Physical servo motors, linear actuators, or similar devices can be used to adjust position of the RID display units until software monitoring the location of the RID units relative to the position of a user's eyes (such as seen in the eye tracking cameras) indicates that the RID display are in proper alignment with eyes. The positions of the RID units can then be stored and used to reposition the RID displays for that same user during a later session. Optical encoders can be used to position the RID displays at predefined locations for a known IPD. The encoders can provide an absolute or relative position. Instead of encoders, the known displacement of an RID unit for a given 'tick' of a servo motor can be used to determine when the RID is displaced an appropriate amount for a known IPD./

A headset system, such as described above having a wide-angle RID display or other wide-angle display system can be used to perform visual field tests quickly and efficiently on a patient. A visual field test is used to determine the entire area (field of the vision) that can be seen by the users' eyes while the user's gaze is focused on a single point, including to where a patient's peripheral vision begins and ends and how well they can see objects in their peripheral vision. The normal field of view of a person's eyes spans about 120 degrees of arc. A wide-angle display headset system as disclosed herein is particularly suited for administering an automated perimetry exam.

Test patterns can be presented in various locations within the field of view and the patient feedback indicating when the pattern becomes visible is detected and recorded. Administering the test using the VR headset allows the user to move their head while keeping the position of the test field relative to the patient's eyes unchanged. This can reduce patient stress during the testing process.

There are various conventional test patterns used for testing. Patterns include:

*10-2: measures 10 degrees temporally and nasally and tests 68 points (conventionally used to test for macula, retinal and neuro-ophthalmic conditions, and advanced glaucoma)

*24-2: measure 24 degrees temporally and 30 degrees nasally and test 54 points;

*24-2C: measure 24 degree plus 10 degree temporally and nasally and testing 64 points; and

*30-2: measure 30 degrees temporally nasally and test 76 point.

These test patterns cover the central visual field and respect the vertical and horizontal meridians. The test point locations are equidistant from each other and are separated by a fixed set of degrees; for example, there is a separation of six degrees apart for 30-2 and 24-2. The 24-2 pattern is based on the 30-2 pattern, but the most peripheral ring of test locations is removed, except for the two nasal points.

According to an aspect of the invention, the VR headset system is programmed with plurality of different test patterns. A doctor can manually select a given test pattern to be used or a sequence of set patterns from those programmed in the system. The software will present the visual stimuli to the patient in accordance with the selected test pattern and record the results. Alternatively, the system can be programmed to sequence through a series of selected tests automatically. According to a particular feature, when multiple different tests are to be executed automatically, the system can randomly select data points from the complete set of data points available for each test so that the various tests are essentially merged together and run in parallel. When the test results are completed, the testing data can be output to a remote computer storage area, such as control system 16 or system 20. The data can also be stored in a local or remote data store 18 for later reference.

Eye tracking camera systems in the headset can be used to determine when the patient's gaze is directed a target, such as a point or small image in the center of the field of view. At the initiation of a test, the system can monitor eye gaze to determine when the patient is looking steadily at the center target. Tests can be initiated after this condition is met.

Eye tracking data can also be used during the testing process to determine when the patient's gaze has shifted away the center target. In one embodiment, when software detects a gaze shift the test can be paused and the patient automatically instructed to the return their gaze to the target. Testing can be resumed when this condition is met, e.g., by analysis of the eye tracking data. Alternatively, eye tracking data can be used to determine the angular offset of the user's relative to the center target. This offset can be used to generate a correction factor to be applied to the offset of the test data point being displayed. For example, if the data point for a given test is offset 30 degrees from center but when the patient indicates that they have seen the data point their gaze is shifted 10 degrees towards that data point, the detection can be treated as applying to a data point with only a 20 degree offset. The software would not consider the 30-degree offset data point as having been tested and so this point could be retried another time. Likewise, if a gaze offset is detected before a data point is displayed, the angular position of the data point can be adjusted by that offset so that the relative offset of the data point when shown is as intended. In the example above, where a 10 degree gaze offset is detected, a 30 degree offset data point in the direction of the offset could be displayed at the 40 degree position so that the actual offset for the patient is the proper 30 degrees.

A common and important eye examination involves taking pictures of the retina using a fundus camera. The fundus optical equipment in conventional designs are bulky and expensive, particularly in systems where the camera is designed to provide a wide field of view within the eye so as to image as much of the retina at one time as possible. According to an aspect of the invention, a miniaturized fundus camera is provided. The fundus camera can be mounted inside of a VR-style headset, such as headset 12 in a dedicated configuration or as part of a removable optics module 110, 300, and used to provide narrow and wide field retinal imaging capabilities. Data can be collected from a live video of the eye while the Fundus camera is taking a set of images. Eye-tracking and image processing can be used to combine images captured by the camera to generate an image that covers most or all of the retina.

The fundus camera component can be movably mounted within the headset to allow the camera aperture to be positioned at various locations in front of a user's eye. In one configuration, the fundus camera i mounted in a pivotable arm inside of a VR-style headset. Pivoting the arm allows the camera aperture to be moved in front of the eye of a person wearing the headset so that retinal images can be captured. The camera can then be moved away and at least partially out of the field of view, for example, to allow viewing of video displays that may also be included in the headset. In a further configuration, the fundus camera is mounted on a rotatable pivot that rides in a track along a part of the periphery of the headset providing an additional degree of freedom for camera positioning.

Mechanical linkages can be provided to allow direct manual adjustment of the position of the fundus camera within the headset. Where the fundus camera is movable, servo motors, linear actuators, or other mechanisms can be provided to allow the cameras to be moved by remote control. Software can be used to properly position the fundus camera directly in front of a user's eye. The software can process images from eye-tracking cameras. Images from a camera in the fundus camera could also be used. Live displays of eye-tracking and/or fundus camera images can be shown on a remote PC (or an external screen display on the VR headset such as shown in FIG. 4) and the person administering the test can control the position of the camera manually using a computer input or other input to align it with the user's eye. The software could also be configured to analyze the eye tracking camera and/or fundus camera images and use that data to automatically position the fundus camera in the correct location in front of the user's eye.

As discussed further below, during a fundus imaging system, the Fundus camera will capture in-vivo images of the eye interior during normal eye saccades or while performing an eye motor movement. Simultaneously, eye tracking cameras can be used to keep track of the orientation of the patient's eye. Eye position can be recorded in terms of spherical, cartesian or another coordinate system and the position data is stored in a manner that allows the eye position at a given time to be linked to an image captured by the fundus camera at the same time. Eye coordinate information is used to determine the portion of the retina captured in a corresponding fundus image and thereby which fundus images belong adjacent to each other. The in-vivo images are segmented, and a collage is created to fit edges of segmented images together using coordinate information collected from eye tracking camera. An image processing algorithm then combines the segmented images to create a wide field view visualizing the fundus of the eye. By combining eye tracking data with images of the eyes, the eye images can be stitched together to create a full image of the data collected; and with extended field of view on each eye, such as from up to 120° of horizontal field of view and 135° of vertical field of view.

Figures 10A, 10B:
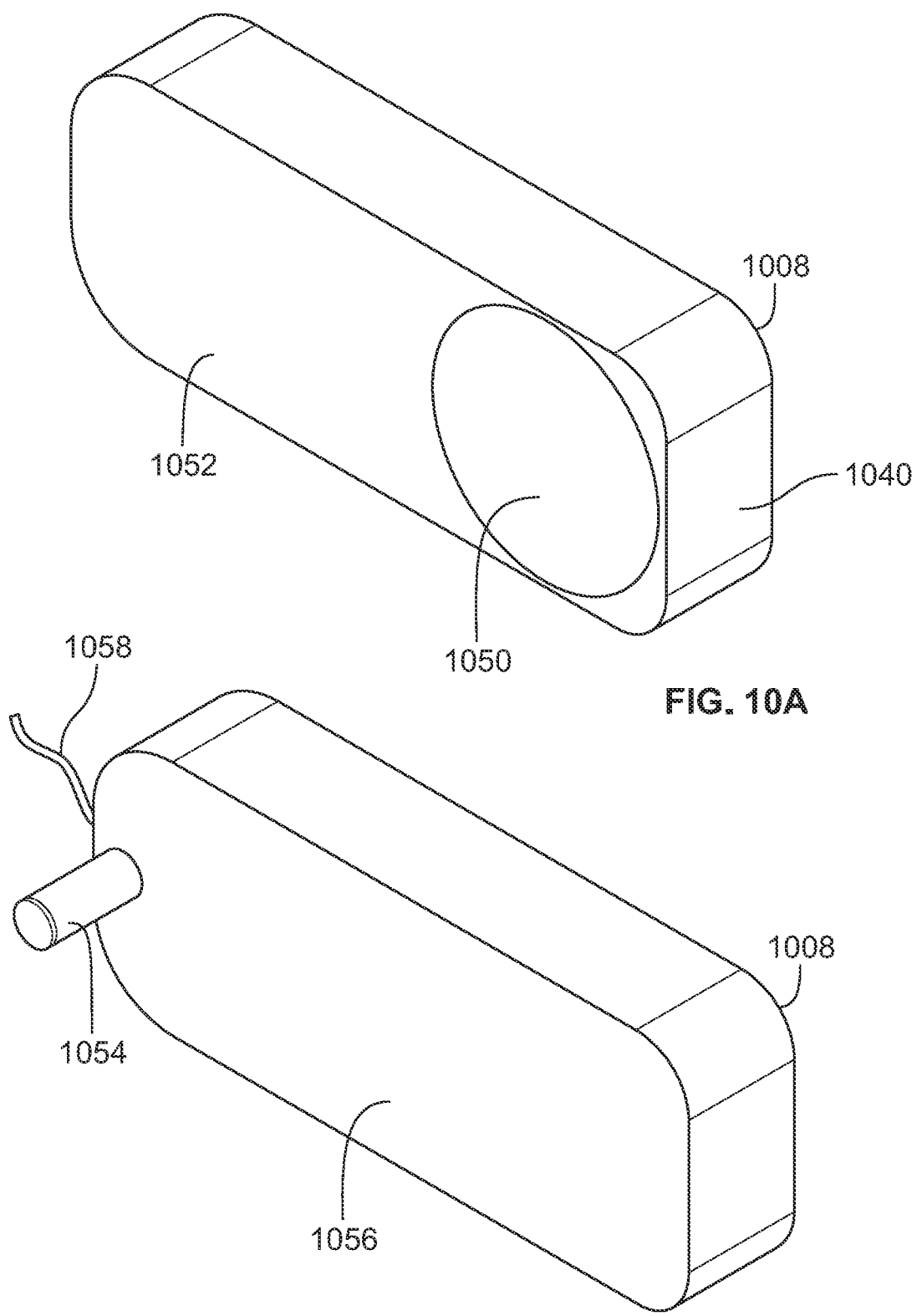
FIGS. 10A and 10B show views of a miniaturized fundus camera module mounted in a housing.

FIGS. 10A and 10B show front and rear views, respectively of a fundus camera module 1008 suitable for mounting in a headset. The camera module 1008 has an elongated housing 1040. A camera objective 1050 is located the front side 1052 of the housing and through which a camera internal to the housing 1040 can capture images of object in a field of view in front of the objective 1050. The housing 1040 can be made small enough to allow the camera module 1008 to be mounted within a VR style headset 12. For example, the housing 1040 can have a length of between 43 mm and 58 mm, a height of between 11 mm and 22 mm, and a depth of between 22 mm and 33 mm. A particular configuration for the fundus camera internal components is addressed separately below. Alternatively, instead of providing the camera 1008 in its own dedicated housing 1040, some or all of the fundus camera components can be integrated within other components of the headset.

The position of the eyes on the face can vary between different individuals. To address this, the camera module can be movably mounted within the headset 12. Various mounting techniques can be used. In one embodiment, a mounting shaft 1054 extends rearward from the back surface 1056 of the housing 1045. Shaft 1054 can mate with a cylindrical hole within the headset structure to couple the camera module 1008 rotationally to the headset so it can be repositioned as needed to match a patient's eye position. The electronic power and data connections to camera components within the camera module 1008 can be made through one or more electrical and data cables 1058 extending from the housing 1040, integrated within the mounting shaft 1054, or by other means. Alternative structures known to those of skill in the art could also be used to mount the camera 1008 to the headset. For example, the camera housing 1040 can have an aperture that receives a mounting shaft extending from a portion of the headset.

The fundus camera modules 1008 can be fixed or removably mounted to the interior of the headset. One or more camera modules 1008 can be installed for fundus imaging and then removed so that the headset can be used for other purposes. The fundus cameras may also be configured and rotatably mounted in a position within the headset to allow the camera 1008 to be moved partially or fully out of the user's line of sight allowing the headset to be used for other purposes while the fundus cameras are still mounted.

Figure 10C:
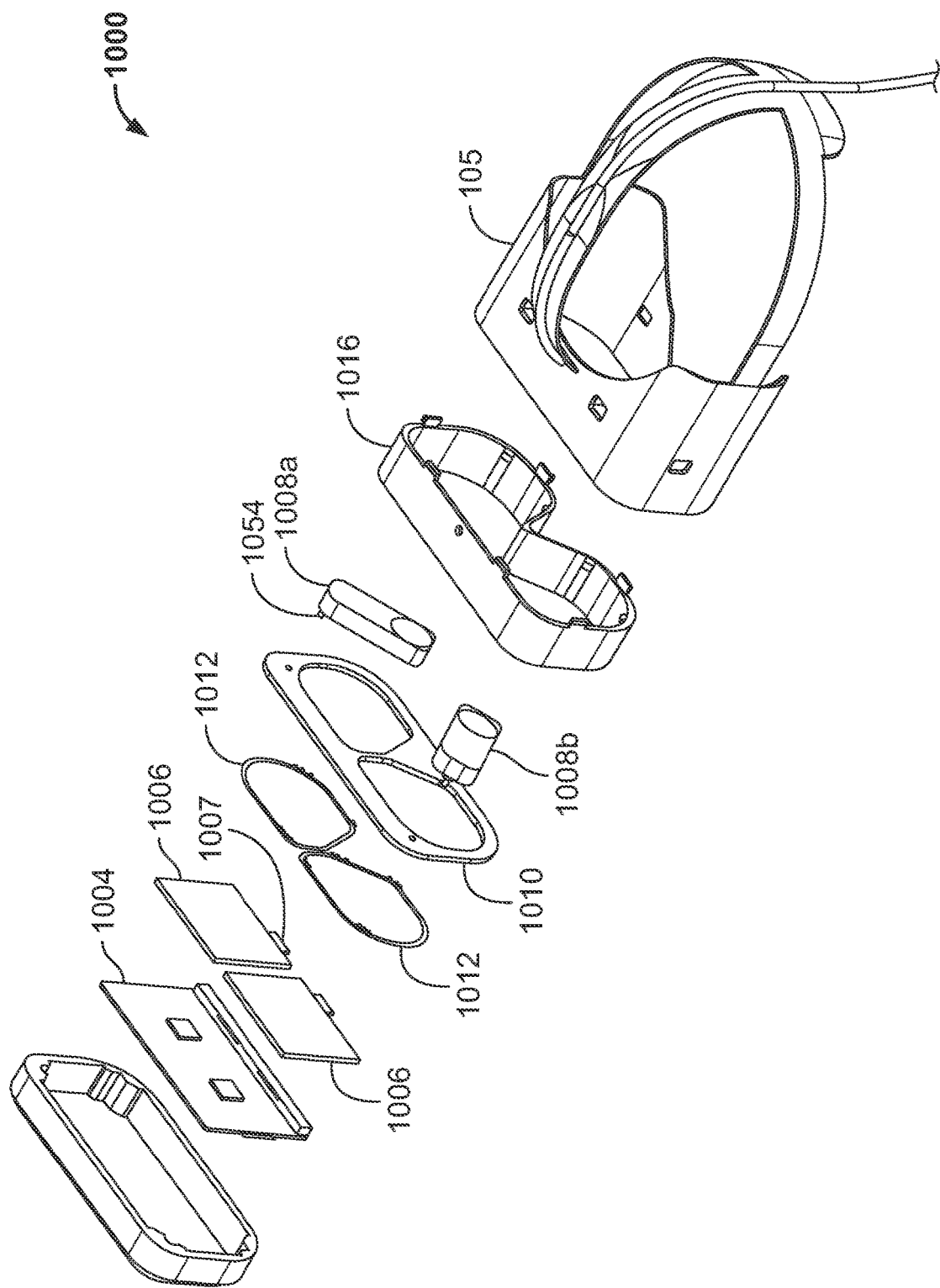
FIG. 10C an exploded view of an optical module that can be mounted in the outer frame of a headset system and that includes rotatably mounted fundus cameras.

FIG. 10C shows an exploded view of an optical module 1000 that can be mounted in the outer frame 115 of headset system and that includes pair of fundus camera modules 1008a, 1008b that are rotatably mounted to a frame assembly 1010. The illustrated configuration of optical module 1000 is similar to the optical module shown in FIG. 7A and can include a motherboard 1004 comprising the computer circuitry used to control the various components in the fundus cameras 1008a,b and other system components and communicate with external devices.

In some configuration, it may be useful to provide image display capabilities as well as fundus camera systems. Left and right images can be provided by a pair of visual displays 1006a, 1006b mounted behind the fundus cameras 1008. During actual fundus imaging, no visual image should be shown on the displays since a dark interior is desired to allow the user's pupil to be fully dilated. However, eye tracking systems that use IR illumination can still be used where the fundus imaging camera is not sensitive to IR illumination, such as by means of an IR blocking filter. A lens module assembly 1012 may also be included if displays 1006a, 1006b are provided. While two fundus cameras are shown, some embodiments may only include a camera. For example, a fundus camera could be mounted on the frame assembly 1010 between the left and right eye areas and mounted so it can be swung back and forth to be positioned in front of either eye. This is addressed further below.

Various other components can also be included in the optical module including LEDs and eye-tracking cameras which can be mounted on the circuit board 1004 or other components. For example, eye tracking cameras could be mounted inside the rear frame 1002 and LEDs mounted on portions 1012a, 1012b of the frame assembly 1010. Electrical connections between these components and driving circuitry can be provided using techniques known to those of skill in the art.

Various other headset configurations with an integrated fundus camera can be provided and various mechanisms for mounting the fundus camera (either fixed or movable) within the headset can be used. In addition to being rotatably mounted, the fundus cameras can also or alternatively be slidably mounted to allow the camera position to be adjusted. To allow the fundus cameras to be moved entirely out of the way of display screens 1004, modifications to the standard VR headset form factor may be needed. For example, the top, bottom, or sides of housing elements 1016, 115 may need to be extended upwards or in other directions to provide a space to receive the fundus cameras when they are not in use.

Figure 11A:
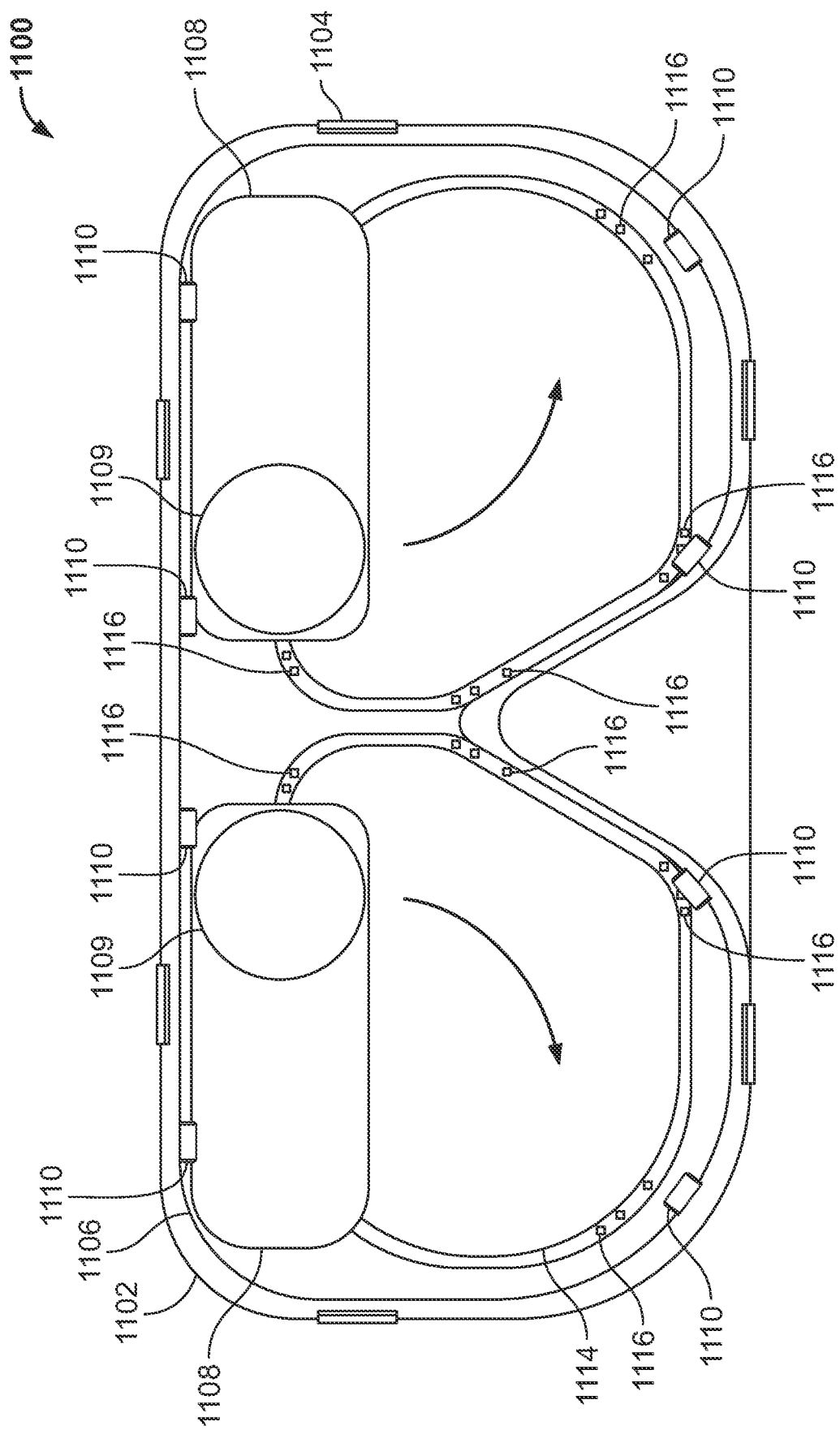
FIGS. 11A and 11B show a headset system with fundus cameras mounted within the headset as viewed from the user-facing side.
Figure 11B:
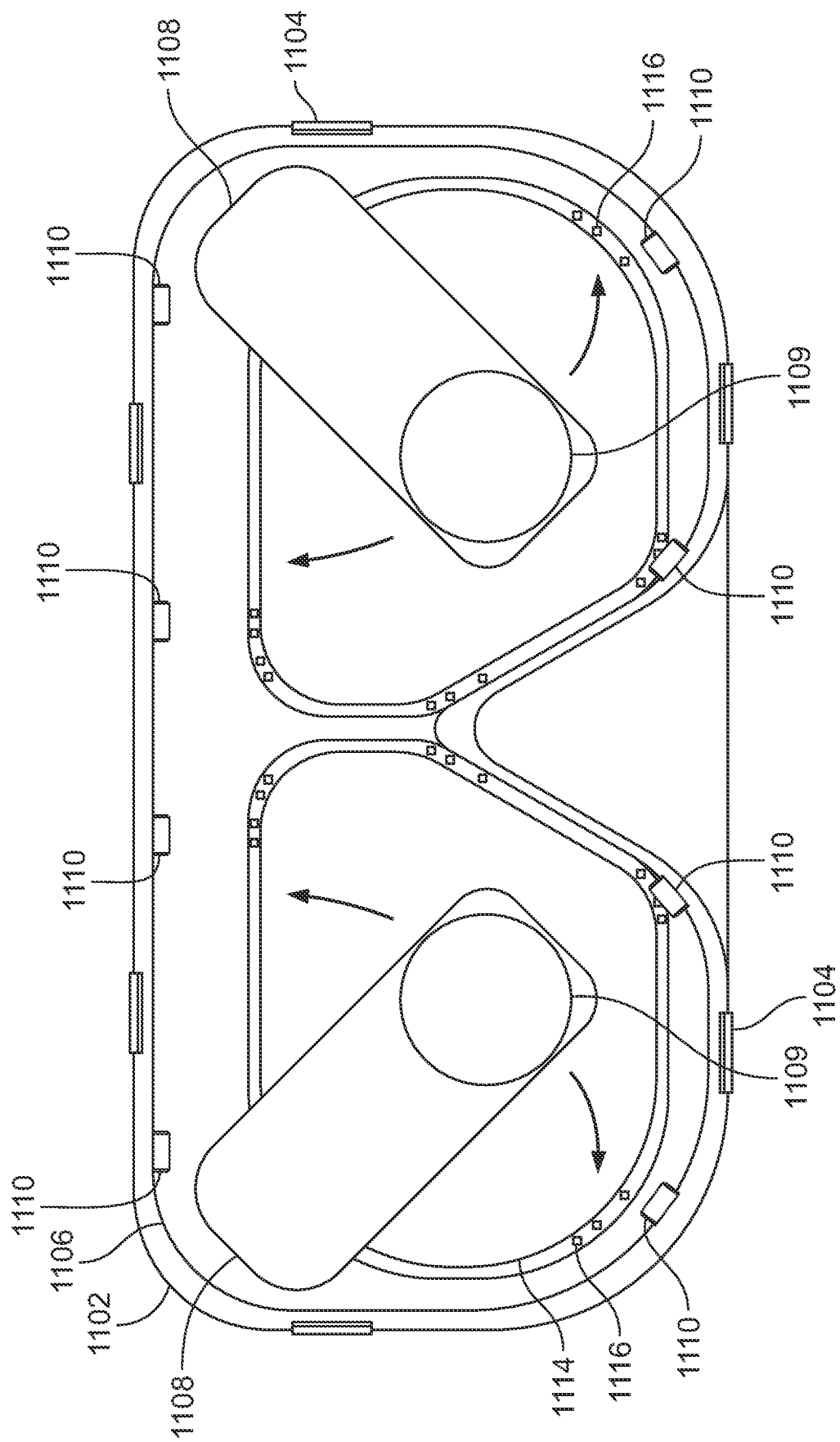

FIGS. 11A and 11B show a headset system 1100 viewed from the user-facing side and that comprises and right fundus cameras 1108 mounted within the headset and corresponding to an assembled version of the configuration of FIG. 10C. FIG. 11A shows the left and right fundus cameras 1108 in a stowed position while FIG. 11B shows the fundus cameras 1108 in a deployed position where the objective aperture 1109 of each camera is moved into a position suitable for retinal imaging. Fundus cameras 1108 as illustrated have the same form factor as cameras 1008 shown in FIGS. 10A and 10B. Alternative form factors can be used for the cameras 1108 and the overall headset design. The camera 1108 is configured in the headset so that it can be positioned to sit closely centered in front of the pupil, such as at a centimeter distance. In a particular embodiment, the fundus cameras 1108 can be rotated to anywhere from 35 to 65 degrees from the retracted or stowed position.

The headset 1100 has a plurality of eye-tracking cameras 1110 which can be IR cameras. The frame rate of cameras 1110 can be fixed or adjustable, such as at a range between 50 Hz to 100 Hz. In the illustrated embodiment, there are four eye tracking cameras 1110 for each eye. Each eye tracking camera 1110 is positioned to allow imaging of a respective quadrant of the user's eye. The eye tracking cameras 1110 are positioned so that when the fundus camera 1108 is engaged one or more IR eye-tracking cameras per eye can view and record the pupil motion for that eye.

Headset 1100 can include includes plurality of user-facing LEDs 1116 which can be used to illuminate a user's eyes for eye tracking purposes and for other reasons. The LEDs 1116 can be arranged in clusters the periphery of a frame assembly 1114 within the headset. A given cluster may comprise different types of LEDs, for example OLED and infrared LEDs, white light LEDs, and blue light LEDs. The clusters of LEDs may be configured to be controlled as a group or each cluster of LEDs 1116 and/or each LED 1116 in a cluster can be independently controlled. Infrared LEDs can also be provided to serve as illumination for the eye tracking cameras 1110.

During a fundus imaging session, the eye-tracking and fundus camera retinal image capture routines can be run simultaneously while the user's eyes are allowed to roam freely. The pupils trace out a path generally similar to a path being traversed on a semi hemisphere. The eye tracking cameras 1110 capture the position of the pupil on a periodic basis and images can be processed to determine the location of the pupil and when the position of the pupil changes. The infrared reflections off the pupil are greater than the reflections off the iris and sclera, thus allowing the camera to distinguish the pupil more readily on the surface of the eye. Images captured with eye tracking cameras 1110 can be processed using conventional eye-tracking algorithms, including Corneal Reflection, Binocular, and Dark pupil Tracking. Parallax compensation can also be implemented.

The fundus camera 1108 will often only be able to image a portion of the user's retina. During the image capture process, the user may be instructed to change the direction of their gaze to thereby change the area of the retina imaged by the camera. The instructions can be audible and/or visible. For example, audio cues can be issued to a user telling them to, e.g., look up, left, right, down, or forward as may be appropriate. One or more visual LEDs 1116 may also be turned on or blinked to indicate a direction for the user to look. These LEDS can be dimly lit so that they are visible but do not emit enough light to cause a user's pupil to contract.

Multiple overlapping retina pictures taken with the fundus camera 1108 can be combined using conventional image stitching algorithm(s) and image recognition software to provide a single image of a large portion of a retina. Using systems as disclosed herein, images can be captured and combined to generate a retina image from up to 120° of the horizontal field of view and 135° of vertical field of view of the back of the eye.

The portion of the retina being imaged can be determined by information about the eye gaze direction and relative location of the fundus camera. Image stitching speed and accuracy can be improved by using this data to determine how multiple images should be positioned relative to each other in advance of stitching. The fundus camera position and eye-tracking information can be stored by in a separate data stream with appropriate time stamp information to allow it to be matched with fundus camera images. The information could alternatively be added as metadata within each image frame captured by the fundus camera so a recording of the fundus camera image stream will also carry this additional data. The metadata can be added to the fundus images by software executed within the headset or the by software in an external system.

The system can be programmed to determine when sufficient images of the retina of sufficient quality have been captured so that all areas of the retina of interest appear in at least one image of acceptable quality. Under normal circumstances an average of 500-720 fundus images frames (at 24 frames per second, 30-second video length) captured by the fundus camera 1108 while the user moves their eye around can provide sufficient imaging. Additional audio and/or visual cues requesting the patient change their direction of gaze can be triggered after a sequence of fundus images are captured if the processing software determines that there are areas of the retina that have not been fully imaged.

Figure 12:
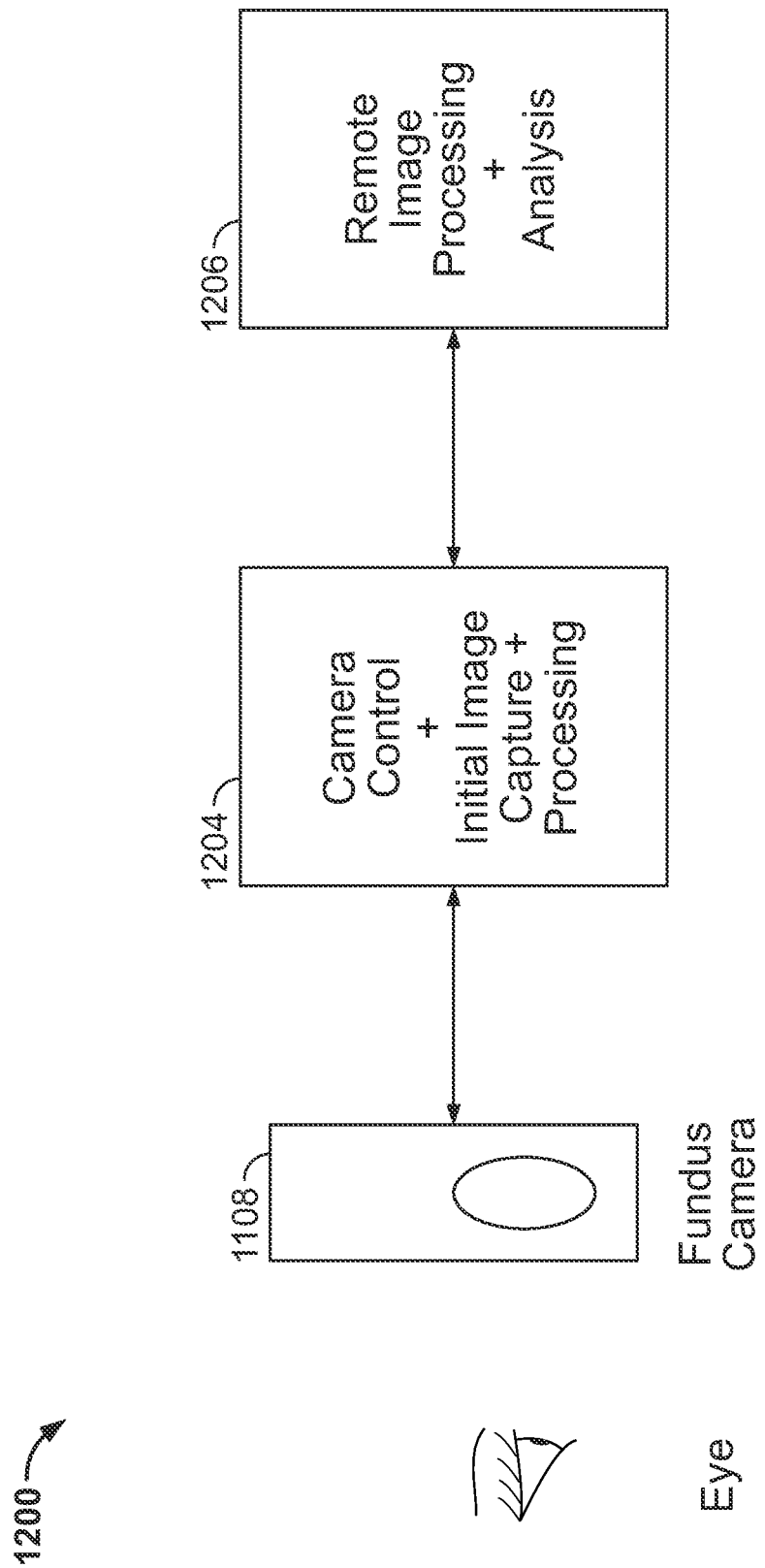
FIG. 12 is a high-level block diagram of an eye-tracking system incorporating a fundus camera.

FIG. 12 is a high-level block diagram of an eye-tracking system 1200 incorporating a fundus camera, such as addressed above. The system includes a head mounted fundus camera, such as a camera 1108 above. Control system 1204 that contains hardware and software to control the fundus camera 1108 for initial image capture and processing and can be a processor board with appropriate hardware and software integrated within a headset and connected to the camera 1208, as discussed above. A remote image processing and analysis system 1206 can be connected to control system 1204 to provide additional functionality. Control system 1204 and analysis system 1206 are analogous to control system 16 and analysis system 20, respectively of FIG. 1

Figure 13:
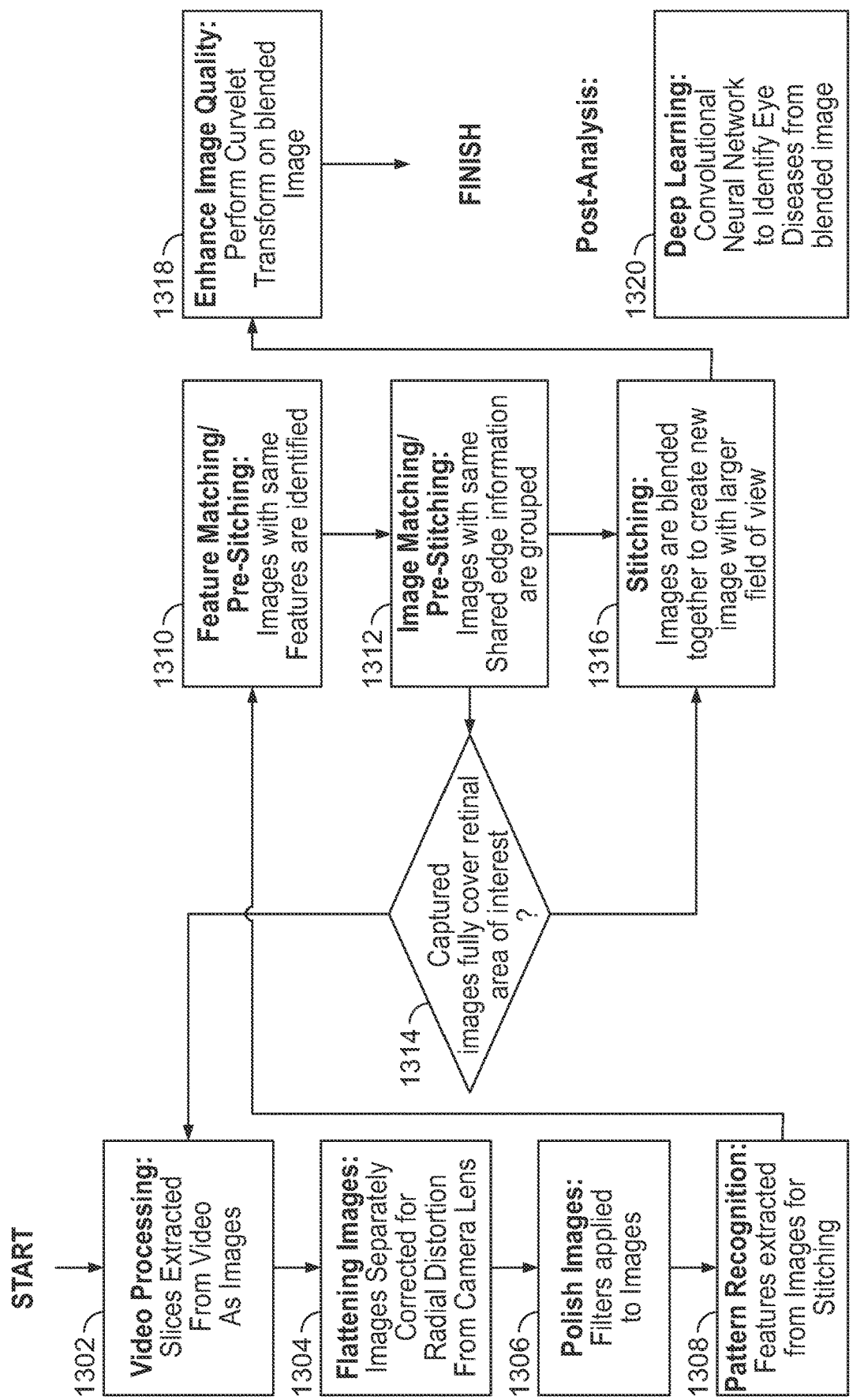
FIG. 13 is a high-level flow chart of a method for retinal imaging using a fundus scanning system.

FIG. 13 is a high-level flow chart of a method for retinal imaging using a fundus scanning system as disclosed herein to generate a completed retinal image. In an initial step, digital images from the fundus camera are received and captured. (Step 1302). In addition to capturing the images, the system can also capture information about the position of the user's eye as determined by analysis of eye tracking imagery and the position of the fundus camera at the time particular images are taken. These data points can be sent to the image processing system linked to the captured images as discussed above. Image capture continues as a user shifts their direction of gaze, e.g., in response to instructions. The captured fundus images are synchronized with the eye and camera position data. Instead of processing the eye tracking images in real time, the eye processing images can be stored along with the captured fundus images and the processing continued at a later time. Image time stamps stored with captured eye and fundus camera images can be used to synchronize the images.

Initial low-level image processing of the captured images is performed. This processing can include flattening to correct for radial distortion (step 1304) and general polishing/cleaning up of the images using conventional image processing filters known to those of skill in the art (step 1306). An initial pattern recognition is performed to extract details from the captured images for subsequent use during image stitching. (Step 1308). Image matching is then performed to determine the approximate best match for descriptors between frames and frames with similar features can be grouped together. While image arrangement can be done solely based on pattern matching, accuracy of this placement can be increased by using the fundus camera and eye position associated with the images as an initial placement followed by smaller scale position adjustment based on feature matching. The placement can be refined using conventional pattern recognition software, such as by grouping and adjusting the position of images based on feature matching. Other techniques for grouping and positioning images known to those of ordinary skill in the art can also be used. (Steps 1310, 1312). The placement can be relative to a concave spherical surface with image position and orientation related to the area of the retina that the image represents. Prior to placement, image quality can also be assessed and pictures that have a quality value below a given threshold can be discarded. For example, pictures determined to be blurred due to eye movement can be discarded.

The image capture process continues until the system determines that the area of the retina to be imaged is adequately captured in one or more images. (Step 1314). For example, the system can continue to capture images until the unstitched but positioned images are arranged on top of each other with no gaps. In an embodiment, the camera will be moved and/or user instructed to move their eye in a sequence designed to provide image capture of the entire area of the retina of interest. After a preset image capture sequence, the system may detect imaging gaps. In such a case an appropriate signal can be generated to move the camera and/or instruct the user to move their eye to a position that will allow the area of the gap to be imaged. Various other methods of determining that enough pictures have been taken of the correct areas may be used and one or more of the flattening, polishing, pattern recognition, pre-stitching, and image matching steps (1304, 1306, 1308, 1310, 1312) can be performed before or after this determination.

The selected and arranged images are then stitched together to create a combined image of the retina (Step 1316). During the stitching process, a bundle adjustment can be performed if more than two frames need to be stitched and blending performed to ensure there are no visible seams and undesirable black areas when frames match to multiple other frames. In areas where two or more frames are overlapping, the combined image can include a composite of the overlapping areas.

Various conventional image enhancements can be applied to improve overall image quality and enhancement details of interest. (Step 1318). The final image can then be stored and analyzed to determine if there are any areas of interest. Appropriately trained machine learning and AI software can also be used to process the image and identify potential issues, diseases, or other areas that may be of interest. (Step 1320).

Figure 14A:
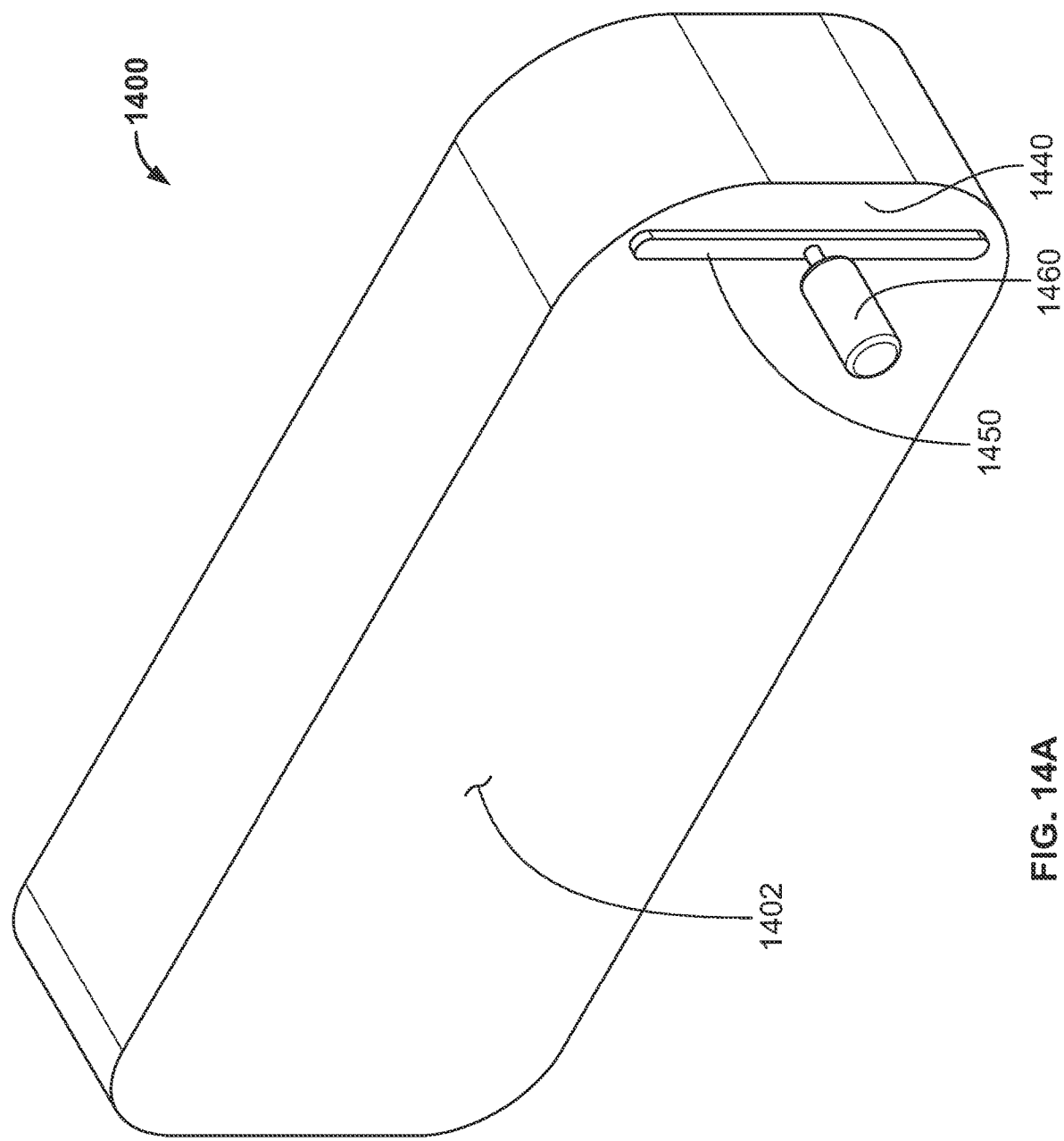
FIG. 14A show a fundus camera with a rotatable mounting assembly.

According to a further aspect of the invention, and with reference to FIG. 14A, a fundus camera 1400 can be rotatably mounted in a headset by means of a rotatable mounting assembly 1440. Mounting assembly 1440 can be driven by a motor and the motor can be used to control the position of the fundus camera in order to place the objective in front of the eye and align it with the pupil. The rotatable mounting assembly 1440 comprises a first portion 1450 that is attached to the fundus camera housing, such as at a rear wall 1402, and a second portion 1460 that can be used to drive the rotation of the first portion and which is attached to the headset. Various motor driven configurations can be used. For example, a motor can be mounted to the second portion 1460 and the first portion 1450 mounted directly on the motor shaft or connected indirectly, such as with gears or belts driven by the motor or by a linear actuator or other device.

Alternatively, the mounting apparatus can be reversed with the motor or other device used to cause rotation mounted to the fundus camera at portion 1450 and shaft around which the camera rotates directly or indirectly connected to the headset via second portion 1460. While the mounting assembly 1440 is shown as being mounted on the rear wall 1404, the rotational mounting assembly 1440 could be mounted elsewhere on the housing, such as a side of the housing or even the front of the housing.

A rotational encoder can also be integrated in or otherwise coupled to the rotation motor or other elements and used to produce a signal that provides an indication of the fundus camera's position. Alternatively, position indicia can be printed on the housing of the fundus camera and an optical sensor used to detect the indicia in order to determine the amount of rotation of the camera. Other ways of sensing the position and/or motion of the fundus camera could also be used. In a two-camera system, both cameras can be moved synchronously or asynchronously.

Figure 14B:
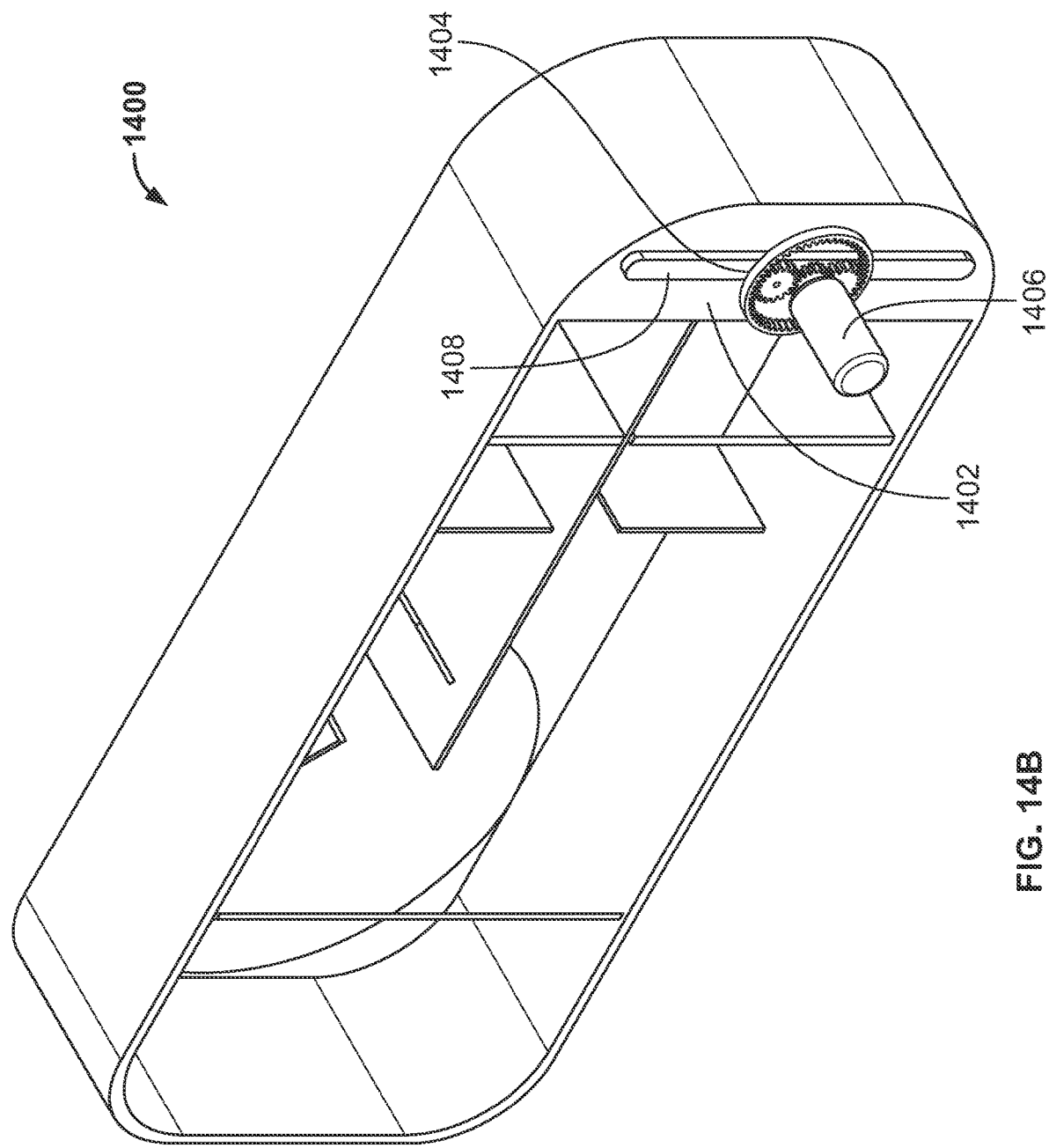
FIGS. 14B-14D show the fundus camera of FIG. 14A with a geared mounting assembly
Figure 14C:
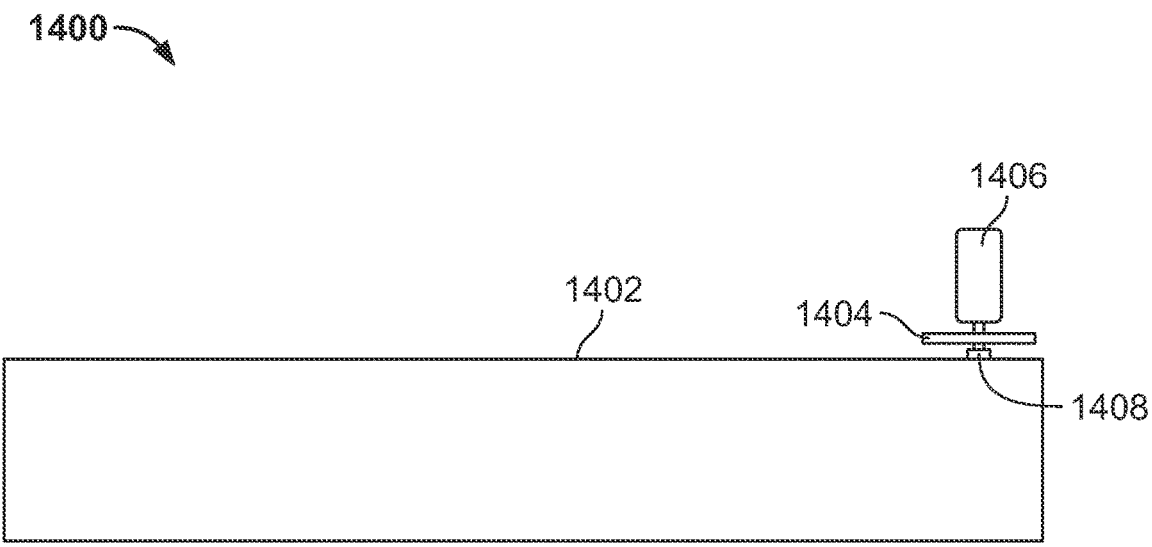
Figure 14D:
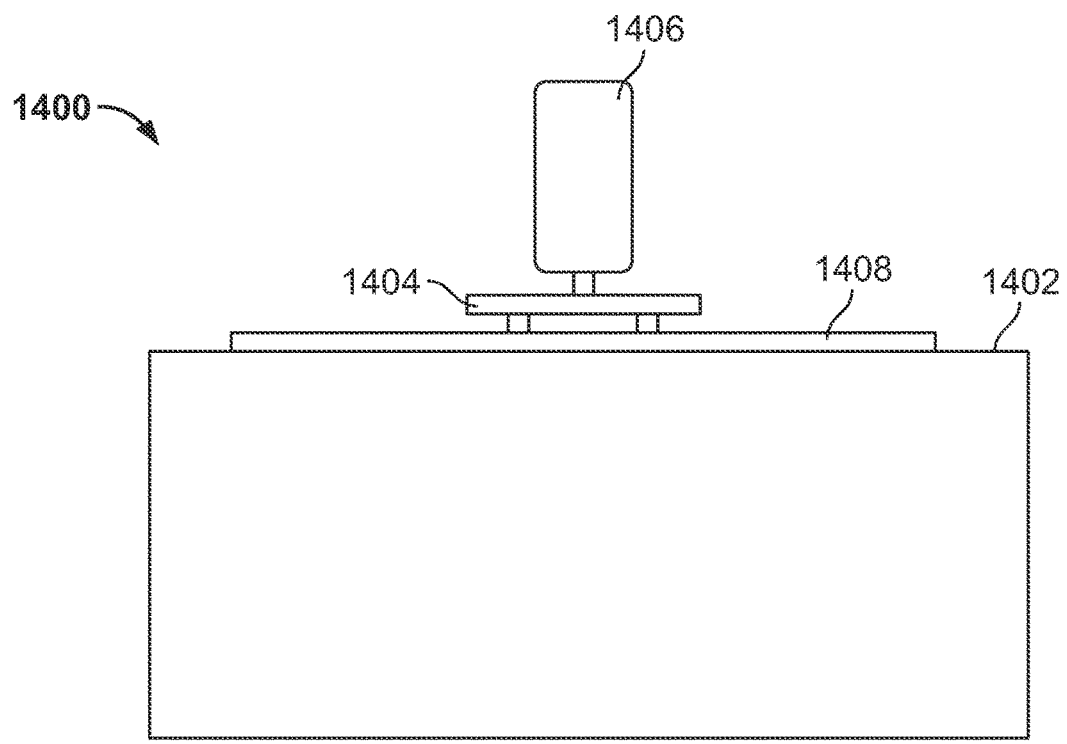
Figure 14E:
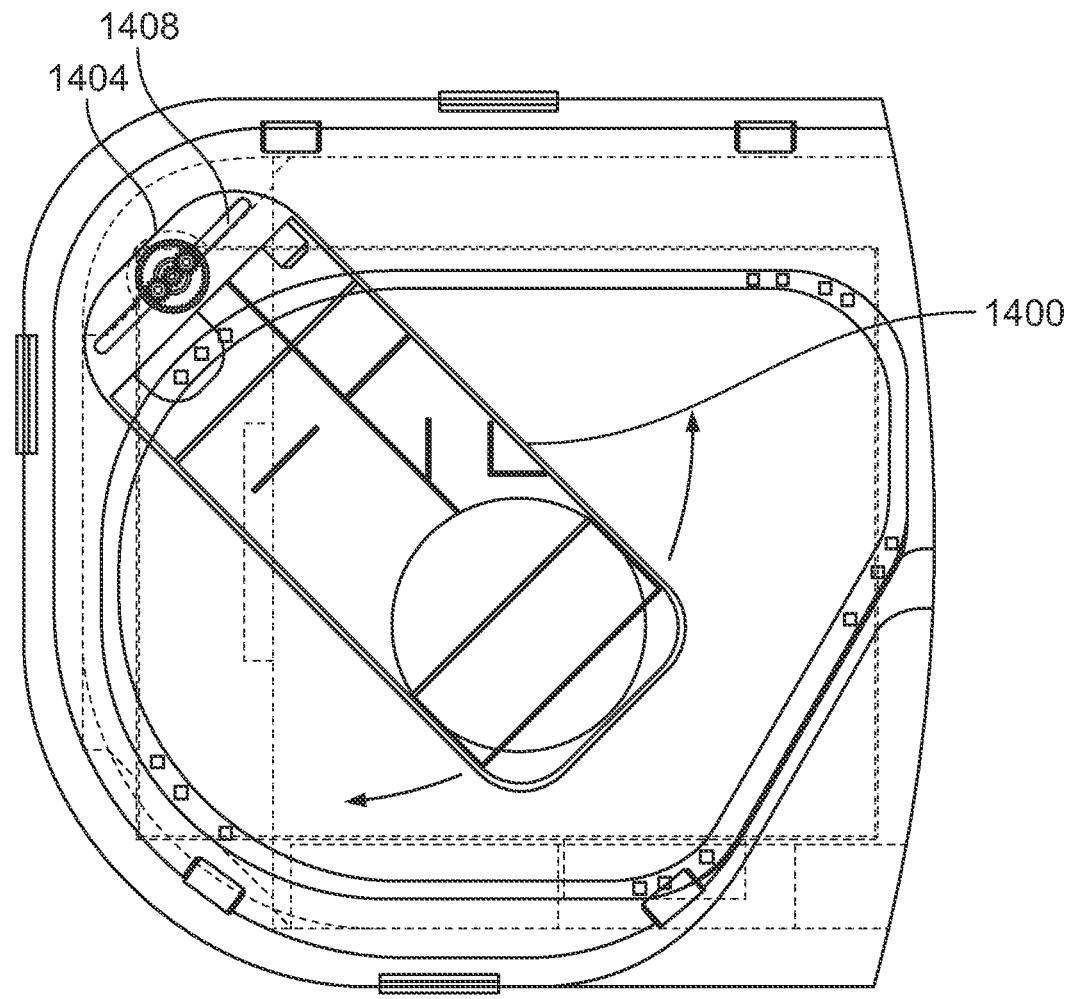
FIG. 14E shows the fundus camera of FIG. 14A mounted in a headset.

FIGS. 14B and 14C show a particular embodiment in which a differential gear mechanism is used to allow the fundus camera to be rotated about a pivot. FIG. 14B is an illustration of a fundus camera with geared mounting assembly 1404 connected to a rear wall 1402 of fundus camera housing at a support plate 1408. The gears can be driven by a motor 1406. FIGS. 14C and 14D are side and end views, respectively, of the embodiment of FIG. 14B. FIG. 14E is an x-ray view showing part of a headset with a fundus camera of FIG. 14B. The mounting assembly 1404 allows the fundus camera 1402 to be rotated about a pivot aligned with the axis of the motor shaft. Various motors can be used. In one embodiment the motor 1406 is an electric coreless vibration DC motor. The motor can be driven by other circuitry in the headset to permit the location of the fundus camera to be automatically adjusted or adjusted manually by a doctor using a suitable software interface The motor 1406 can be mechanically connected to an inner structure of the headset, such as mounting it within an aperture in the frame assembly 1010 of the headset assembly shown in FIG. 10C. The mounting location of the rotatable bracket assembly on the fundus camera and within the headset can vary. In the illustrated embodiment the fundus cameras are mounted at the upper outside corners. The fundus cameras can be mounted in a variety of other positions as well. For example, the fundus cameras could be mounted on the outer sides between the top and bottom, from the lower outside corner, or any other location from which permits the fundus camera to be moved so the objective is in front of a user's eye.

Figure 15A:
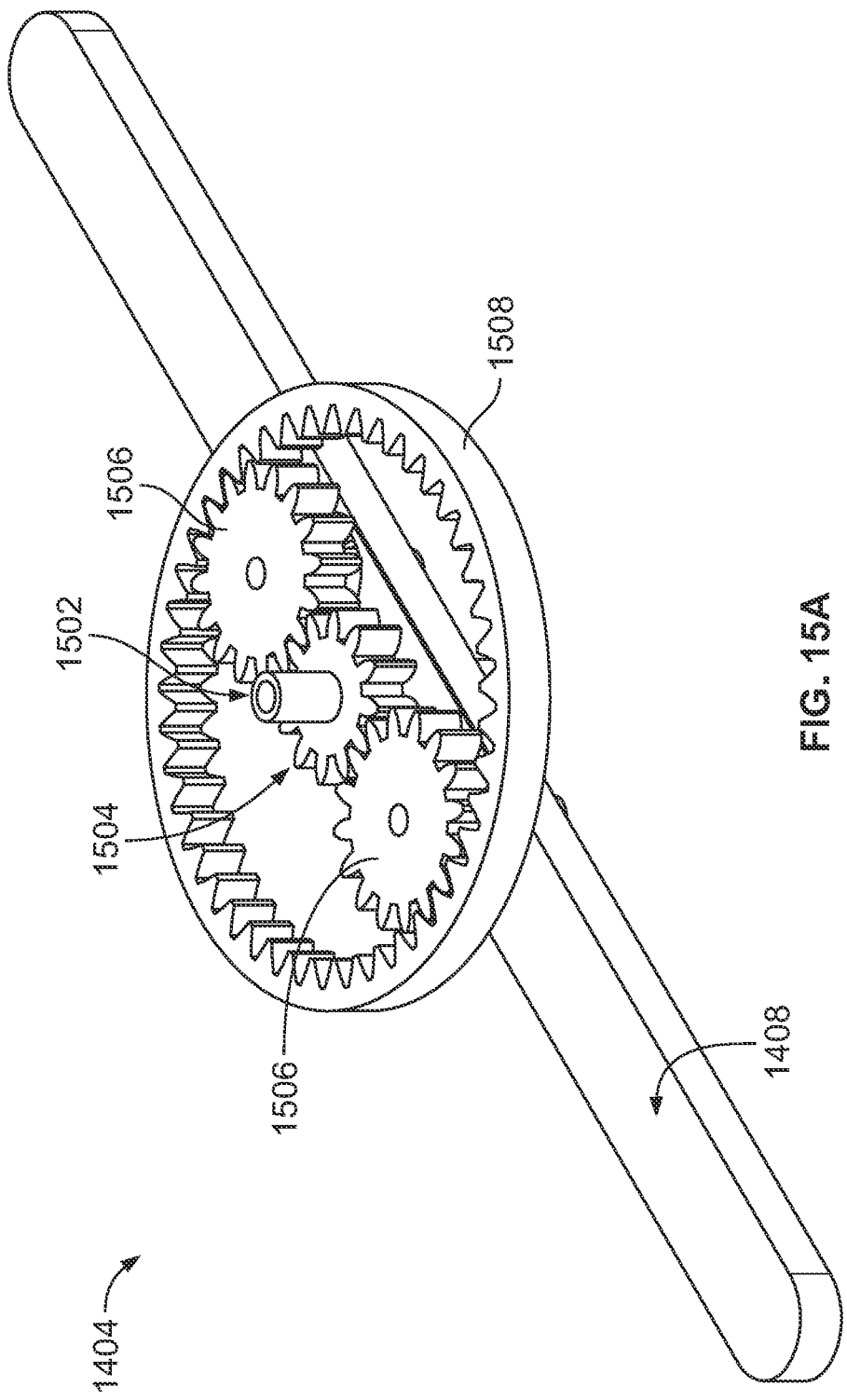

FIGS. 15A and 15B show top and bottom views, respectively, of an embodiment of the geared mounting assembly 1404. The geared mounting assembly comprises a main motor gear 1504 with a motor spoke 1502 allowing attachment of the gear 1504 to a motor. The main motor gear 1504 drives two inner gears 1506 which ride inside an outer ring gear 1508 that is connected to the support plate 1408. Inner surface 1514 of the support plate 1408 is affixed to the rear surface 1402 of the fundus camera housing. Appropriate apertures in the housing surface 1402 allow the axes 1516 of the inner gears and a mounting pin 1512 to pass through. Rotating the main motor gear 1504 causes the ring gear 1508, and thus the fundus camera, to rotate so that, with reference to FIGS. 11A and 11B, the imaging objective 1109 can be positioned at any desired position along an arc centered on the pivot point. While a separate support plate 1408 is shown, the support plate 1408 can be integrally formed in the camera housing or omitted entirely and the ring gear 1508 affixed to or integrally formed in the wall of the headset housing.

Alternative mechanisms to rotatable mount the fundus camera can also be used. In one configuration, instead of a motor, a rotation knob is positioned on the outside of the headset and is mechanically coupled to the fundus camera. A doctor can manually adjust the position of the fundus camera by rotating the knob, e.g., while they us a live video feed from the camera as feedback for positioning.

Rotatably mounting the fundus camera to position the objective along an arc may still not allow optimal positioning. In a further embodiment, and with reference to FIGS. 16A-16E, the mounting assembly portion 1460 that mounts to the headset is not mounted at a fixed location. Instead, portion 1460 of mounting assembly (which could be the motor 1406, the motor shaft if the motor body is mounted on the fundus camera housing, or other element depending on the mounting assembly design) itself is further movably mounted within a track that allows the pivot axis of the rotatable mounting assembly to be moved laterally. By adding an additional degree of freedom to the positioning of the fundus camera, the objective portion of the camera can be positioned in a wider range of locations than possible with a fundus camera that can only move rotationally.

Figure 16B:
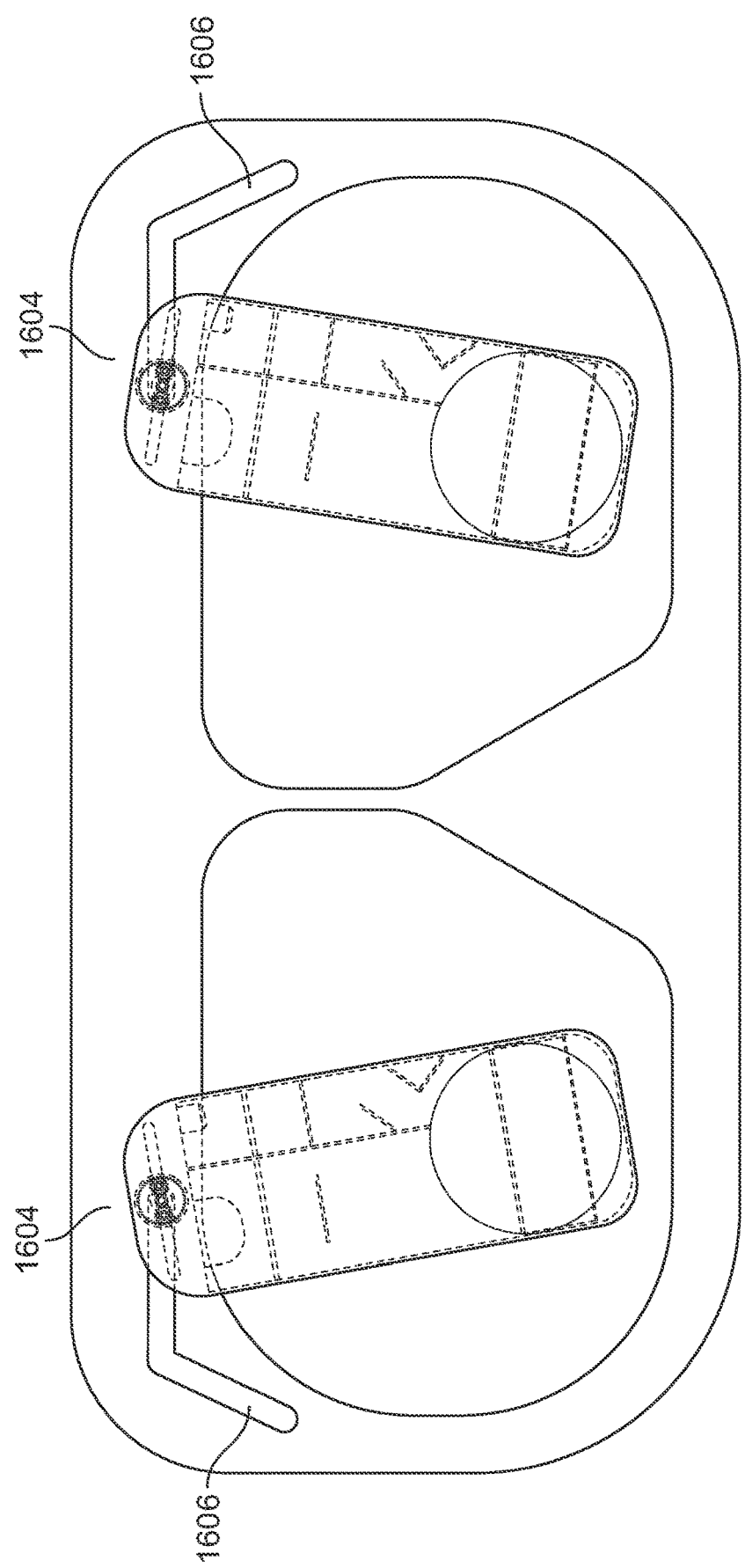
Figure 16C:
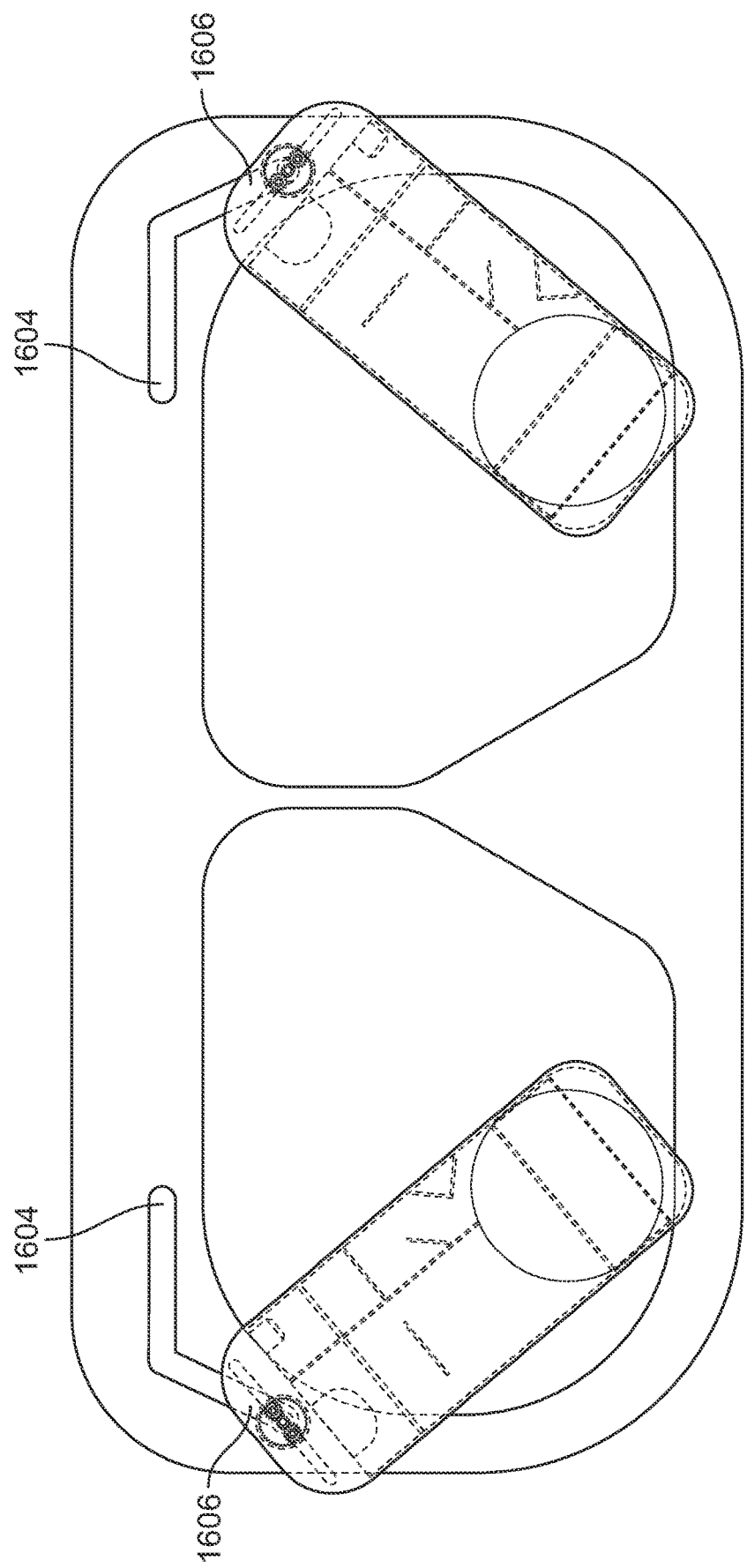
Figure 16D:
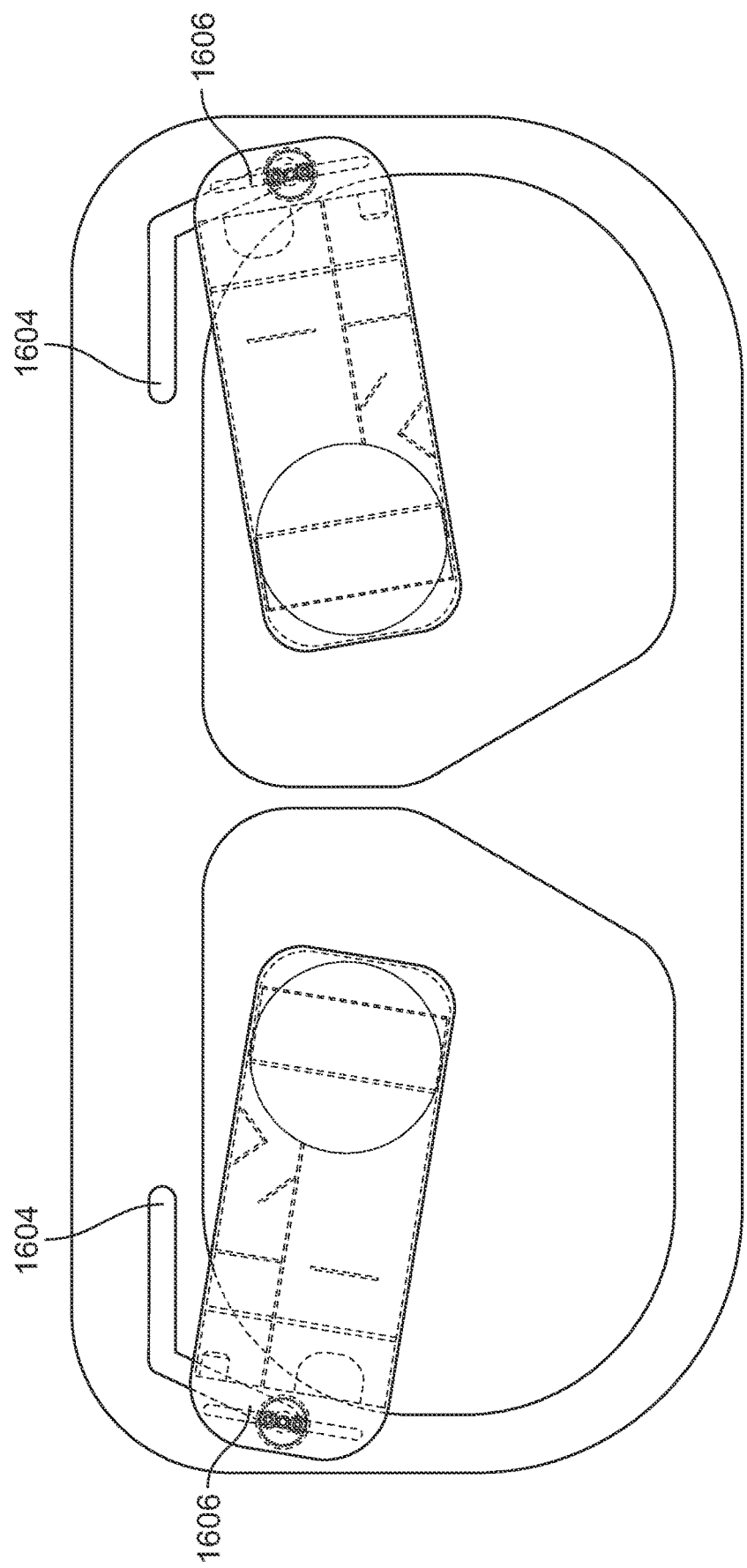

FIGS. 16A-16D show a dual camera assembly where each fundus camera 1400 has a respective mounting assembly 1610 that is used to rotationally couple the fundus camera to the headset so that fundus camera 1400 can be rotated relative to the headset. The mounting assembly 1610 is slidably mounted to the headset within a respective track 1602 having a first end 1604 and a second end 1606. The mounting assembly can be positioned at a plurality of locations along the respective the track 1602, such as at the first end 1604 and the second end 1606 of the track 1602 or various positions in between. At various locations in the track 1602, the fundus camera 1400 can be rotated to adjust its position. FIGS. 16A and 16B show fundus cameras 1400 positioned at the first position 1604 in the respective tracks 1602 and at two different rotational positions. FIGS. 16C and 16D show fundus cameras 1402 positioned at the second positions 1604 in the respective tracks 1602 and at two different rotational positions.

Various mechanical drive systems known to those of skill in the art can be used to move the slidably mounted portion of mounting assembly 1610 to different locations along the track 1604. In one configuration, a movable belt driven by a separate motor can be used. In another configuration, the slot position can be changed using a linear actuator. Likewise, a worm gear or other system can be used to slide the slot mounted portion of the mounting assembly 1610 back and forth. Other movement mechanisms could also be used. The system can be configured to position the pivot point of the camera at predefined fixed locations, such as the ends 1604, 1606 of the slot 1602 or permit the pivot to be freely positioned at variable locations along the track 1602.

Figure 16E:
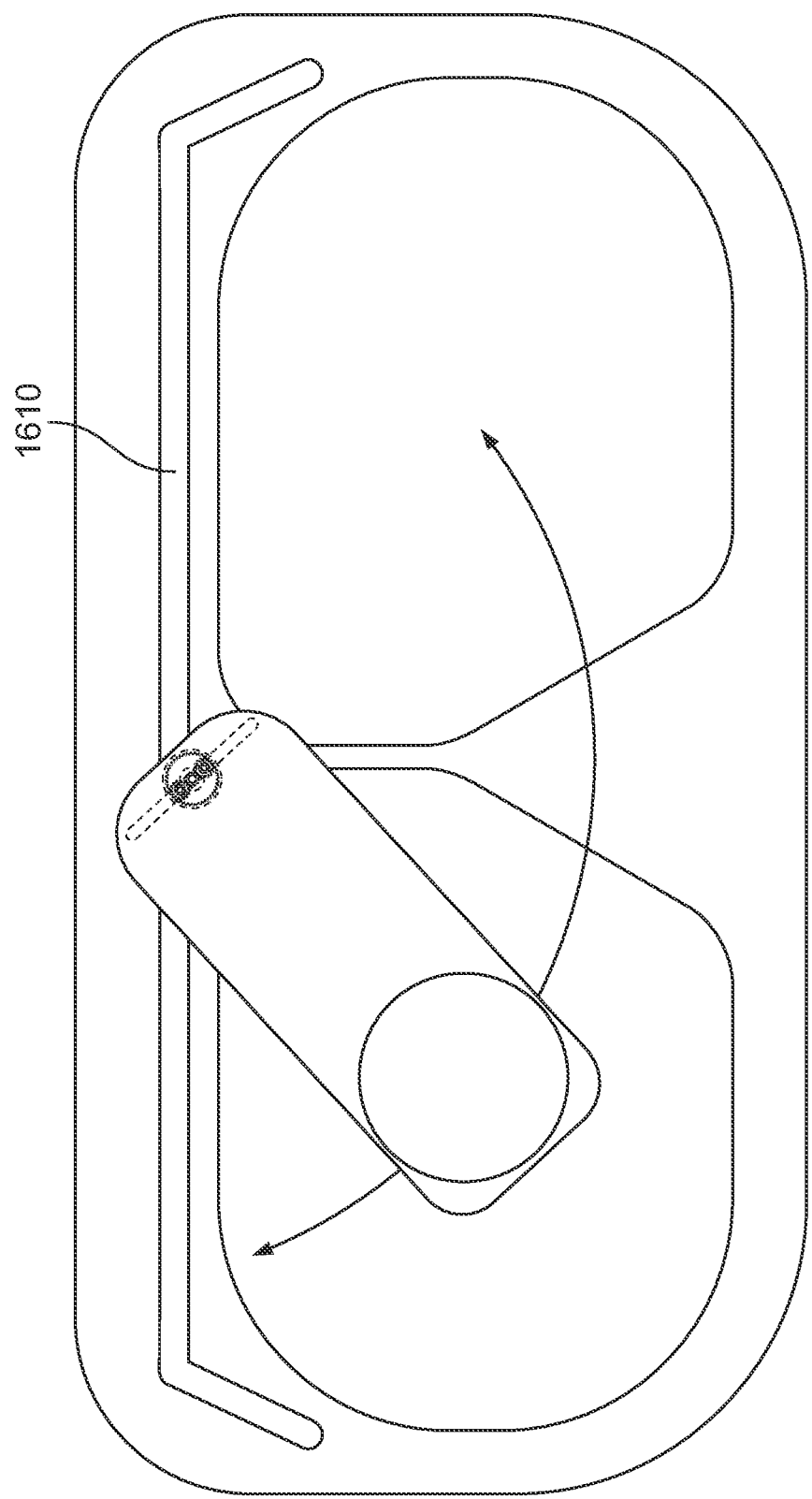

In a further configuration shown in FIG. 16E, rather than dual fundus cameras only a single fundus camera 1402 is used. The pivot axis can be centrally positioned, such as along the top center of the headset so that the fundus camera 1402 can be rotated in front of either eye. To provide an additional degree of freedom in positioning the camera, a track 1610 can be provided to allow the fundus camera to be moved left and right so that it can be positioned at a variety of additional locations on the left and on the right side of the headset, analogous to the dual camera/dual-track system shown in FIGS. 16D-16D.

In an alternative embodiment, instead of rotationally mounting the fundus camera, the mounting assembly can be slidably attached within a slot or track formed on the fundus camera to thereby allow the fundus camera position relative to the mounting assembly to be adjusted along a first axis, such as vertically. The portion of the mounting assembly coupled to the housing could also be slidably mounted allowing motion along a second axis, such as horizontally.

Figure 17:
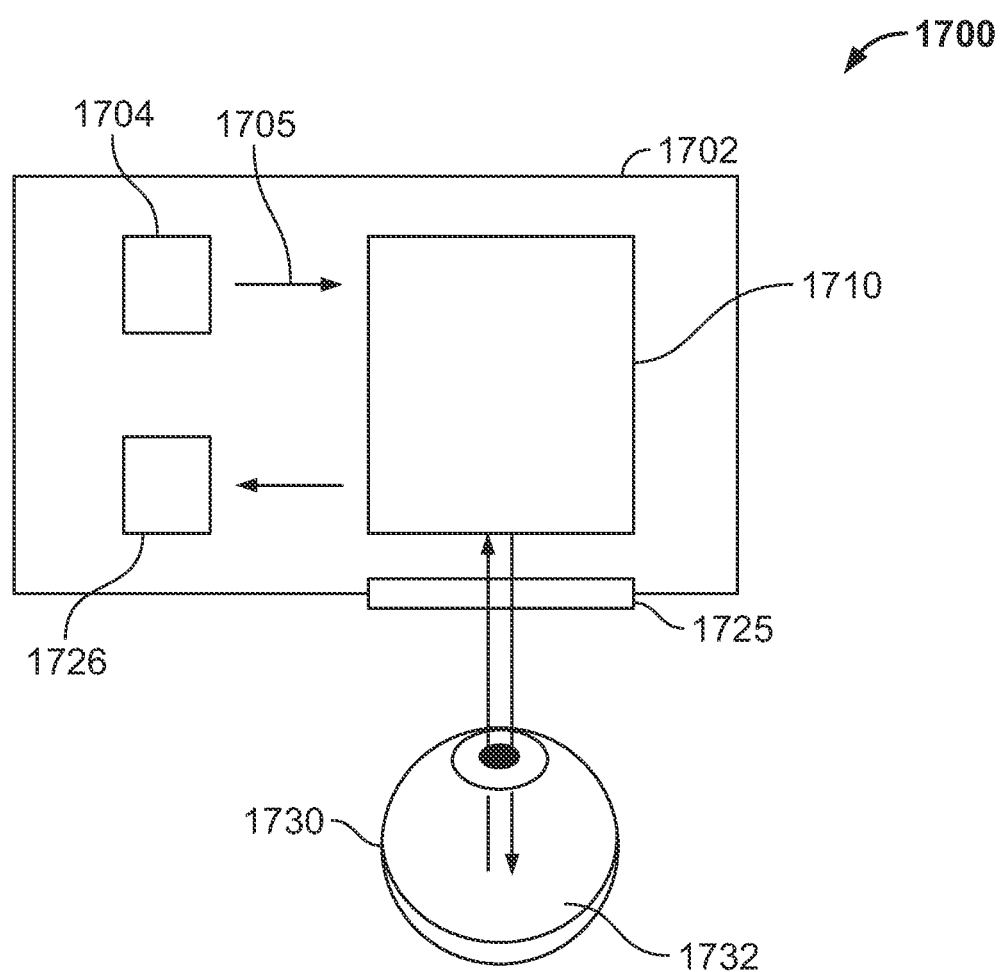
FIG. 17 is a high level schematic diagram of a particular configuration of a fundus camera that can be miniaturized and used in a headset assembly.

FIG. 17 is a high-level schematic diagram of a fundus camera 1700 that can be miniaturized and used in a headset assembly as discussed herein and can also be used in other configurations, such as a hand-held imager. Fundus camera 1700 has a housing 1702 containing a light source 1704 and an image capture camera 1726. Light source 1704 emits light 1705 directed into optical assembly 1710 that directs at least a portion of light 1705 out of the camera through portion 1725 and into the eye 1730 of a patient (when the camera is in use and aligned). The light illuminates the retina 1732. Light reflected by the retina (or other structures within the eye exits the eye and passes through objective portion 1725 and into the optical assembly 1720 which directs at least a portion of that light to into the camera which captures the image.

Figure 18A:
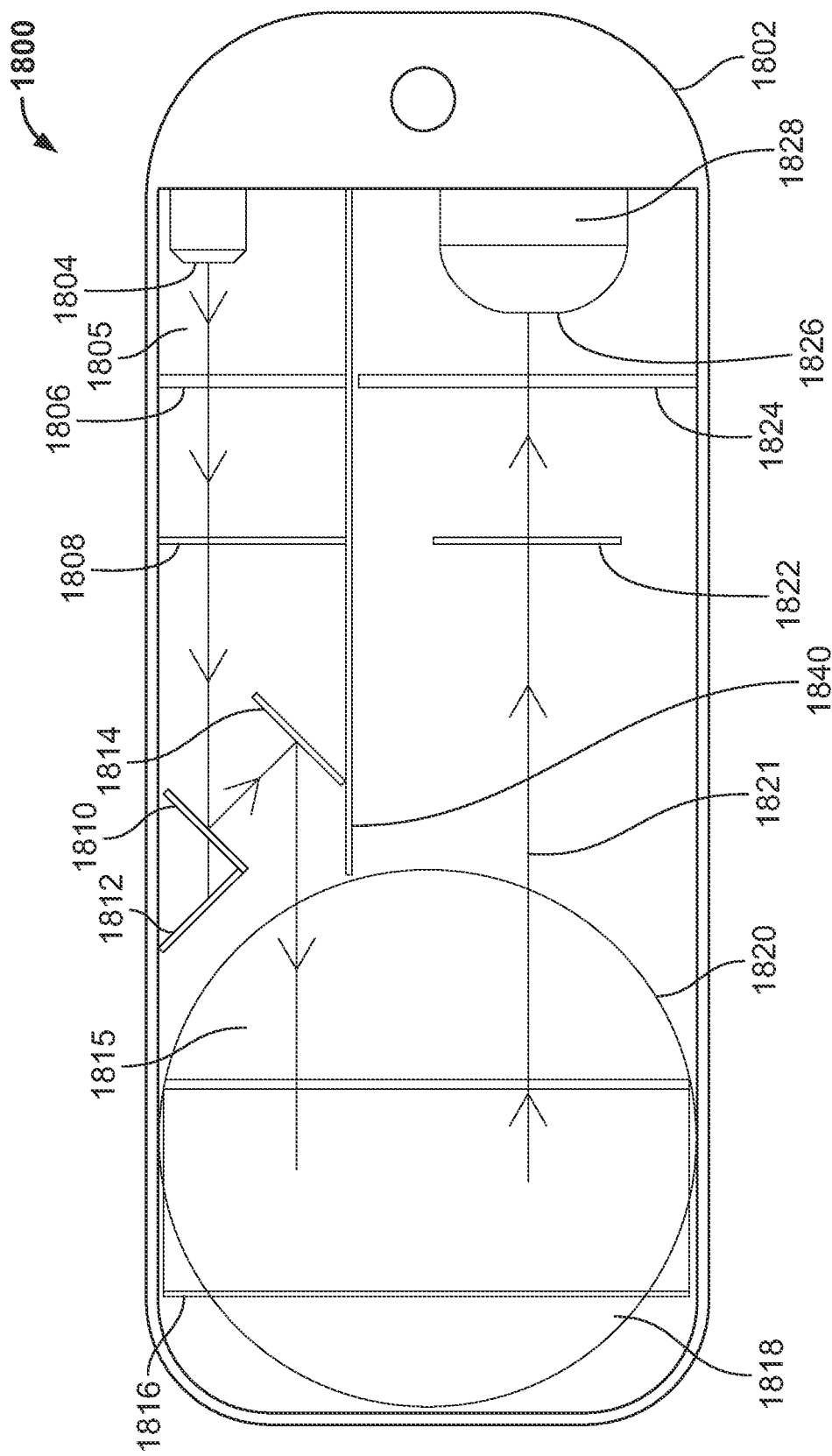
Figure 18B:
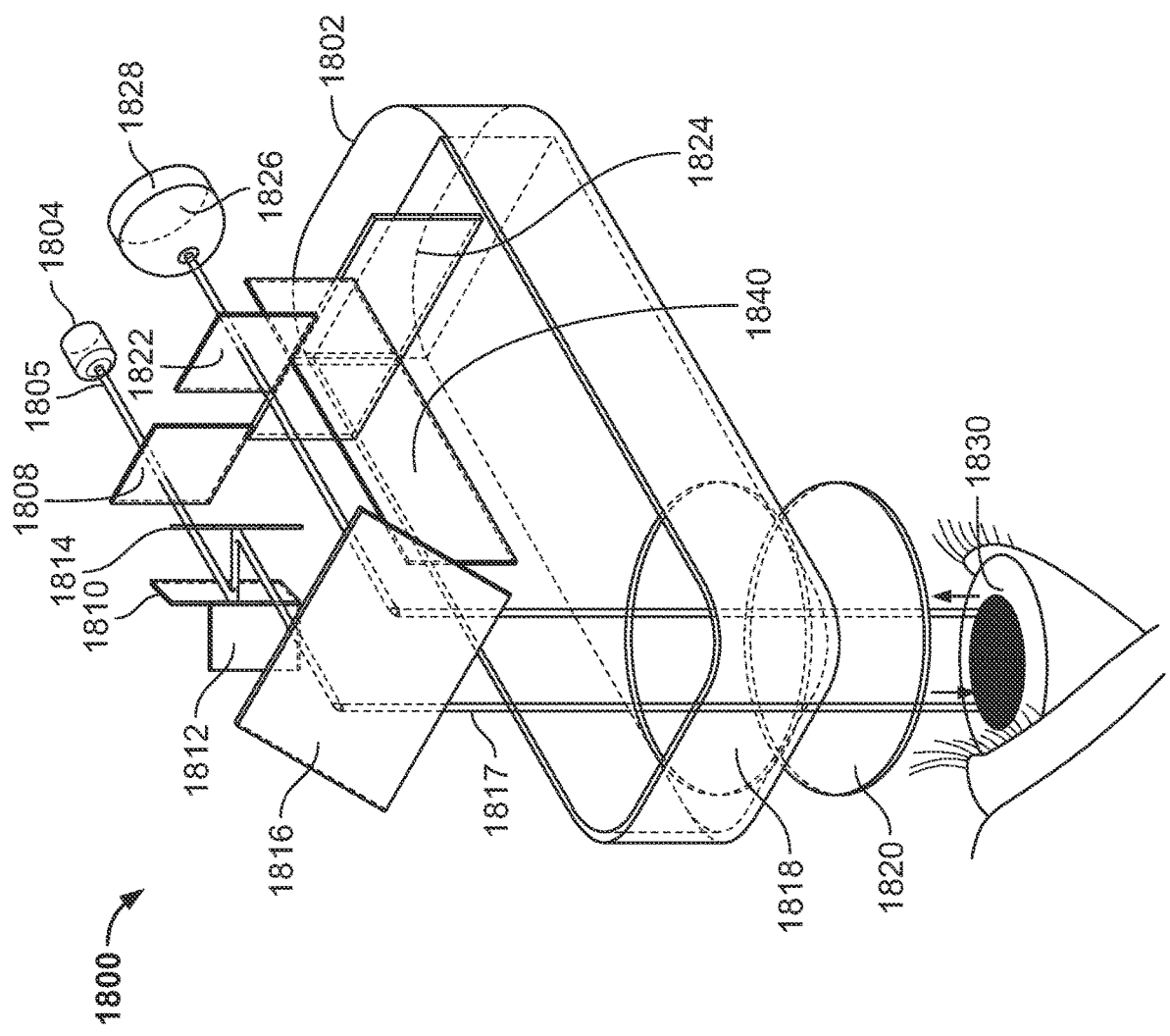
Figure 18C:
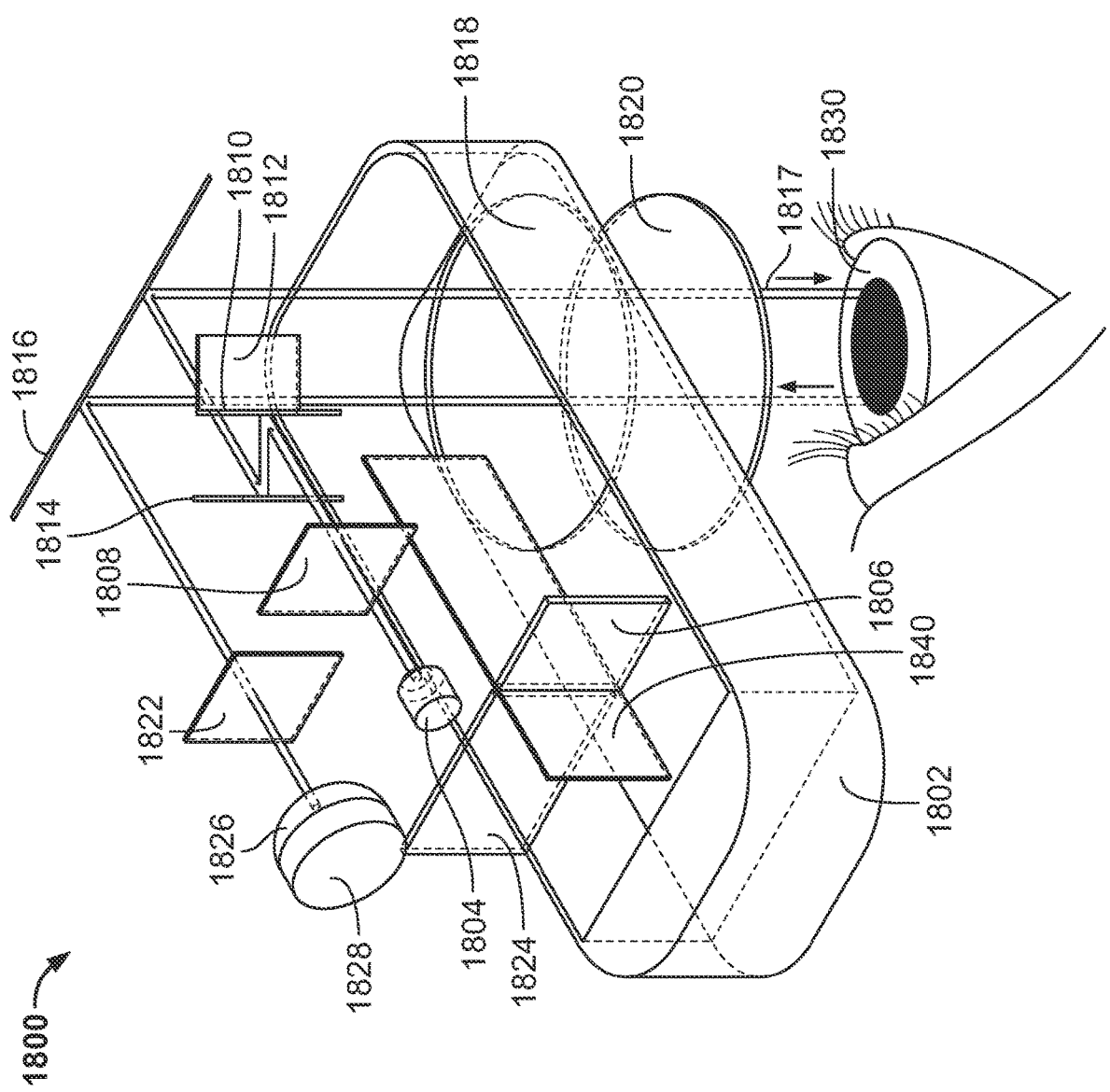

FIG. 18A is a top view of the design of a fundus camera 1800 that can be made small enough, such as only a few centimeters in length, to be mounted in a headset as discussed above, either in a fixed or movable mount. The fundus camera 1800 may also be useful in other systems outside of the VR headset type configuration discussed herein. FIGS. 18B and 18C are perspective exploded views of the design of FIG. 18A.

With reference to FIGS. 18A-18C fundus camera 1800 components are mounted in a housing 1802 and comprise light source 1804 that produces light beam 1805. A flat plate glass 1806 and/or polarizer 1808 can be positioned along the path of beam 1805 to reduce glare. A beam splitter 1810 is positioned along the path of beam 1805 and redirects the light beam 1805 and helps control light dispersion and flare. A light absorbing surface 1812 can also be provided to remove glare and reflections from the light emerging from beam splitter that is not intended to be output from the camera. The beam splitter operates to both redirect the light and to reduce the intensity of the reflected light. This can allow the use of bright LEDs as light source 1804 which may be less expensive and easier to use than low intensity LEDs of equal optical quality. A partially reflective mirror or prism could be used as an alternative to the beam splitter.

In a particular embodiment, the light source 1804 comprises at least one LED that emits light in a wavelength that will excite blood vessels from the group of the blue region 450 nm-500 nm, the violet region 400 nm-450 nm, and the ultraviolet (UV) region 200 nm-400 nm. Multiple LEDs can be provided, and controls may be provided to activate them discretely and in combination. The light source 1804 can include internal lenses or other optical components operative to focus or redirect generated light to produce the light beam exiting the light source.

The light beam 1805 reflected from the beam splitter 1810 can be redirected by one or more mirrors, such as mirrors 1814 and 1816. The final mirror, such as mirror 1816 is positioned to direct the light beam 1805 90 degrees or other suitable angle so light beam 1805 exits the housing 1802. Light 1817 reflected from the mirror 1816 can be passed through a lens 1818, such as a spherical lens that helps compensate for the focal length of the eyes and provides a wide field of view for image capture. A negative lens to correct aberrations can also be provided. An external plate glass 1820 can be provided to protect the system from external contaminants. If the camera assembly 1800 is positioned properly, the light will enter the eye of a user 1830 and illuminate at least part of the retina.

In the illustrated embodiment, light emitted from the light source is passed through a flat plate glass 1806 and/or polarizer 1808, then the beam splitter 1810 which reduces the light intensity, and the beam is then redirected by one or more mirrors 1814 and 1816. These elements can be positioned in the light beam in other orders. For example, the beam splitter could be positioned before the class 1806 and/or polarizer 1808.

At least one of the light directing mirrors, such as mirror 1814, can be rotatably mounted along at least one axis to allow the direction of the light beam 1815 leaving the mirror 1814, and thereby the direction of the light beam output from the camera, to be redirected. Redirecting the light beam by moving mirror 1814 allows the system to illuminate different areas of the retina in the eye during image processing. This redirection also shifts the center of the camera's field of view allowing variation in the area of image capture within the eye. Providing two movable mirrors that can pivot along different axes can allow the direction of the light beam to be redirected in two dimensions. The mirror position can be automatically adjusted under control of the system software. Multiple images can be taken with the eye and camera in a fixed location while the mirror is moved to sweep the illumination across the retina portion visible to the camera and adjust the imaging direction of the camera to better capture images of those portions. The mirror position can also be adjusted in response to changes in the position and/or gaze direction of the eye. Combining the images can provide a higher quality image with a more even illumination.

Light 1821 reflected by the retina or other structures in the eye exits the eye and passes through the plate 1820, lens 1818, and is redirected by mirror 1816. A polarizing filter 1822 and glass plate 1824 can be provided on the return optical path for further glare reduction. A lens 1826 focuses the light onto imaging camera 1826. Imaging camera 1828 can include internal lenses that operate to focus incoming light onto a sensor element. A diaphragm or wall 1840 can be provided between the outgoing and incoming optical paths to avoid stray light from the light source 1804 from impacting the image.

For at least a portion of the optical path within the camera, the outgoing light beam to illuminate the eye and the reflected light directed towards the imaging camera travel along a parallel path. On the illustrated embodiment, the axis of light beam 1805 emitted from the light source 1804 remains parallel to the beam axis of returned light for the majority of the beam path, the exception being the path between the beam splitter 1810 and fold mirror 1814.

The imaging camera 1820 can comprise a conventional high-resolution digital camera, such as a 20 MP resolution at pixel size 2.4 um×2.4 um and a frame rate of 24 fps. While ag global shutter imaging system can be used, a rolling shutter features advantageously allows for image capture not at a single instant in time but rather by continuously scanning across the eyes rapidly, both vertically and horizontally. A high-speed data port, such as USB 3.0, allows for rapid transfer of data from the camera to other components in a optics module 110 or external devices. The camera can be configured to be run freely continuously or under the control of hardware and/or software triggers. Software exposure control can be provided through an appropriate API with the camera's internal control circuitry. Appropriate lens assemblies will be known to those of skill in the art to provide a focused image of the retina on the imaging chip. Mechanical and/or liquid lens focusing systems can be used to compensate for variations in distance to the user's eye. Still angle images of 45 degrees or more can be captured with the camera system and those images combined to produce a retinal image of up to 120 degrees.

Fundus images captured using a system as disclosed herein can be transferred to a image processing system in real time and processed, such as disclosed herein, to generate a full 120-degree image of the eyes.

While particular designs for swappable optics modules are disclosed herein, the system can alternatively be mounted directly within the outer frame of the head mount as part of a dedicated headset system. In such a case, the outer frame of the module would not be necessary, and the components could instead be mounted directly into the outer frame of the headset. In another configuration, modular optical modules are provided but are fixed mounted within a head mount as part of a manufacturing process. In this manner, customized VR headset systems with different functionality may more easily be manufactured on demand. Custom headsets with integrated fundus cameras, OCT systems, and perimetry testing systems can also be provided.

Various aspects, embodiments, and examples of the invention have been disclosed and described herein. Modifications, additions, and alternations may be made by one skilled in the art without departing from the spirit and scope of the invention as defined in the appended claims.

The invention claimed is:

1. A headset for use in optical examination, the headset comprising:
 a headset body configured to be worn on a face of a user, the headset body having a front user-facing face side and a back side opposite the face side, a left side, a right side, a top and a bottom;
 the face side having a forward edge configured to rest on the user's face when the headset is worn and having a concavity therein extending back from the forward edge and defining an open region having a surface with a rear portion and a surrounding side, the open region being adjacent an eye of the user when the headset is worn;

a fundus camera comprising an imager and optics within a camera housing, the optics comprising a camera objective, the fundus camera having a field of view extending outwards from the objective, the optics configured to direct light entering the camera objective to the imager;

a mounting assembly rotatably coupling the camera housing to the headset body, the camera housing extending into the open region, the fundus camera positionable so that the camera field of view extends from the open region towards the eye of the user;

wherein rotation of the fundus camera moves the camera objective within the open region, said rotation allowing adjustment of a position of the camera objective relative to an eye of a user when the headset is worn by the user.

2. The headset of claim 1, the mounting assembly further comprising a motor which when activated causes rotation of the fundus camera housing relative to the headset body.

3. The headset of claim 1, the camera housing having first and second ends, a front side and a back side, the camera objective positioned in the front side adjacent the first end of the camera housing, the mounting assembly comprising first and second portions rotationally coupled to each other, the first portion of the mounting assembly connected to the camera housing adjacent the second end of the camera housing, the second portion of the mounting assembly connected to the surface of the open region headset body.

4. The headset of claim 3, wherein the second portion of the mounting assembly is slidably mounted in a track formed in the headset body and is movable between a first track position and a second track position, wherein motion of the second portion within the track provides translational motion of the fundus camera within the open region.

5. The headset of claim 3, wherein the second portion of the mounting assembly is connected to the headset body substantially midway between the left and right sides of the body, the fundus camera being rotatable from a first position suitable to image a left eye of the user when the user is wearing the headset to a second position suitable to image a right eye of the user when the user wearing the headset.

6. The headset of claim 1, the fundus camera comprising a left fundus camera rotationally mounted toward a left side of the open region and a right fundus camera rotationally mounted toward a right side of the open region, the left and right fundus cameras configured to image the left and right eye respectively of the user when the headset is worn by the user.

7. The headset of claim 1, the fundus camera further comprising a light source internal to the camera housing, the light source configured to generate a light beam that exits the camera objective and can illuminate a retina of the user's eye when the light beam passes through a pupil of the eye.

8. The headset of claim 7, the fundus camera further comprising an exit mirror directing the light source through the camera objective, the exit mirror movable on at least one axis to change a direction of the light beam exiting the objective.

9. The headset of claim 1, further comprising a plurality of eye tracking cameras configured to capture images of the eye of the user when the user is wearing the headset, the eye remaining visible to at least one eye tracking camera as the fundus camera is moved within the open area.

10. The headset of claim 1, further comprising a display situated behind the fundus camera relative to the front side of the headset, the display configured to present images visible to the user of the headset when the headset is worn.

11. The headset of claim 10, the fundus camera is movable between an imaging position in which the fundus camera obscures a first portion of the visual display from the user and a storage position in which an amount of the visual display obscured from the user by the fundus camera is less than when the fundus camera is in the imaging position.

12. The headset of claim 1, wherein the fundus camera is removably mounted within the headset body.

13. The headset of claim 12, wherein the headset comprises an outer frame and an optics module removably mounted within the outer frame, the fundus camera mounted to the optics module.

14. A computer controlled method for fundus imaging of a retina of a patient's eye comprising the steps of:

mounting a headset on the head of a patent, the headset comprising a headset body having a face side having a forward edge configured to rest on the user's face when the headset is worn, a concavity extending back from the forward edge and defining an open region adjacent a user's eye, the headset further comprising a rotatably mounted fundus camera having a camera field of view extending from a camera objective towards the face of the user, wherein rotation of the fundus camera moves the camera objective within the open region and changes a position of the camera objective relative to the user's eye;

receiving a first image of the eye captured by the fundus camera;

adjusting the rotational position of the fundus camera based on the first image to change alignment of the camera objective with a pupil of the eye; and capturing a retinal image of the eye with the fundus camera after the rotational position of the fundus camera has been adjusted.

15. The method of claim 14, wherein the step of adjusting the rotational position of the fundus camera comprises the steps of displaying the first image on computer display of a computing device external to the headset and receiving in the headset from the computing device control signals operative to cause the fundus camera to rotate.

16. The method of claim 14, the step of capturing the retinal image of the eye after the rotational position of the fundus camera has been adjusted comprising capturing a plurality of retinal images, each retinal image being of a respective portion of the retina.

17. The method of claim 16 further comprising the step of mapping each of the plurality of retinal images captured by the fundus camera to a respective position in a retinal image map, the position of a respective retinal image in the retinal image map based on the respective portion of the retina imaged in the respective retinal image.

18. The method of claim 17, the headset further comprising an eye tracking camera, the method further comprising the steps of:

capturing using an eye tracking camera within the headset a plurality of images of the eye during the step of capturing the plurality of retinal images with the fundus camera;

analyzing images captured by the eye tracking camera to determine a gaze direction of the eye; and determining the respective portion of the retina imaged in that respective image based on the determined gaze direction and the position of the fundus camera objective relative to the pupil at the time a respective image was captured by the fundus camera;

the position of retinal images mapped to the retinal image map being a function of the determined portion of the retina imaged for each of the respective plurality of retinal images.

19. The method of claim 18, wherein the step of mapping further comprises matching image features in captured retinal images, the mapping of retinal images to the retinal image map being a further function of said feature mapping.

20. The method of claim 16, further comprising the step of determining based on predefined imaging criteria that a predefined minimum portion of the retina has been imaged, the step of capturing the plurality of retinal images with the fundus camera being terminated after such a determination.

21. The method of claim 20, further comprising the steps of automatically identifying a portion of the retina that has not been successfully imaged and automatically instructing the patient to alter a direction of gaze so as to bring the portion of the retina that has not been successfully imaged into the field of view of the fundus camera.

22. The method of claim 21, the step of automatically instructing the patient to alter the direction of gaze comprising illuminating a visible light source within the headset to indicate a desired gaze direction.

23. The method of claim 17, further comprising the step of stitching the mapped retinal images into a combined retinal image and storing the combined retinal image in a computer memory.

24. The method of claim 16, further comprising the step of instructing the patient to change a direction of gaze during the step of capturing the plurality of retinal images with the fundus camera.

25. The method of claim 24, wherein the headset further comprises a plurality of visible light sources arranged around an internal periphery of the open region; the step of instructing the patient to change the direction of gaze comprising illuminating at least one of the plurality of visible light sources to indicate a desired gaze direction.

26. A computer controlled method for fundus imaging of the respective retina of a user's first and second eye comprising the steps of:
mounting a headset on the head of a patent, the headset comprising a headset body having a face side having a forward edge configured to rest on the user's face when the headset is worn, a concavity extending back from the forward edge and defining an open region adjacent the first and second eyes, the headset further comprising first and second rotatably mounted fundus cameras in the open region, the first fundus camera adjacent to the first eye and the second fundus camera adjacent to the second eye;
adjusting a rotational position of the first and second fundus cameras based on an interpupillary distance between a pupil center of the first eye and a pupil center of the second eye; and
capturing a plurality of retinal images with the first and second fundus cameras, each retinal image being of a respective portion of the retina of the respective eye.

27. The method of claim 26, wherein the step of adjusting the rotational position is performed automatically.

28. The method of claim 27, wherein the step of adjusting the rotational position comprises the steps of:
receiving images of the first and second eyes; and
adjusting the rotational position of each respective fundus camera based on the received images of the respective eye.

* * * * *